(12) United States Patent
Kashyap et al.

(10) Patent No.: US 11,865,146 B2
(45) Date of Patent: Jan. 9, 2024

(54) METHODS AND MATERIALS FOR USING BIOMARKERS WHICH PREDICT SUSCEPTIBILITY TO CLOSTRIDIUM DIFFICILE INFECTION

(71) Applicant: Mayo Foundation for Medical Education and Research, Rochester, MN (US)

(72) Inventors: Purna C. Kashyap, Rochester, MN (US); Eric J. Battaglioli, Rochester, MN (US); Vanessa L. Hale, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 405 days.

(21) Appl. No.: 17/093,154

(22) Filed: Nov. 9, 2020

(65) Prior Publication Data
US 2021/0128644 A1   May 6, 2021

Related U.S. Application Data

(63) Continuation of application No. 15/762,203, filed as application No. PCT/US2016/053073 on Sep. 22, 2016, now abandoned.

(60) Provisional application No. 62/222,034, filed on Sep. 22, 2015.

(51) Int. Cl.
| | |
|---|---|
| *A61K 35/741* | (2015.01) |
| *A61K 35/745* | (2015.01) |
| *A61K 35/744* | (2015.01) |
| *A61K 35/742* | (2015.01) |
| *A61K 35/00* | (2006.01) |
| *G01N 33/68* | (2006.01) |
| *G01N 33/569* | (2006.01) |
| *C12Q 1/04* | (2006.01) |
| *A61P 31/04* | (2006.01) |

(52) U.S. Cl.
CPC .......... *A61K 35/741* (2013.01); *A61K 35/742* (2013.01); *A61K 35/744* (2013.01); *A61K 35/745* (2013.01); *A61P 31/04* (2018.01); *C12Q 1/04* (2013.01); *G01N 33/56911* (2013.01); *G01N 33/68* (2013.01); *A61K 2035/115* (2013.01); *G01N 2800/06* (2013.01); *G01N 2800/26* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2008/0241226 A1 | 10/2008 | Abeln et al. | |
| 2014/0095241 A1 | 10/2014 | Loring et al. | |
| 2014/0296134 A1* | 10/2014 | Savidge | C12Q 1/04 514/254.11 |
| 2014/0363397 A1 | 12/2014 | Allen-Vercoe et al. | |
| 2019/0216861 A1 | 7/2019 | Kashyap et al. | |

FOREIGN PATENT DOCUMENTS

| | | | |
|---|---|---|---|
| WO | WO 2013/037067 | 3/2013 | |
| WO | WO 2014/110493 | 7/2014 | |
| WO | WO-2014110493 A1 * | 7/2014 | ........... A61K 35/742 |
| WO | WO 2014/121304 | 8/2014 | |
| WO | WO-2014121301 A1 * | 8/2014 | ............. A61K 35/37 |
| WO | WO-2014121304 A1 * | 8/2014 | ........... A61K 35/741 |
| WO | WO 2014/150094 | 9/2014 | |
| WO | WO 2015/095241 | 6/2015 | |

OTHER PUBLICATIONS

Antharam et al., "Intestinal dysbiosis and depletion of butyrogenic bacteria in Clostridium difficile infection and nosocomial diarrhea," J. Clin. Microbiology, Sep. 2013, 51(9):2884-2892.
Camilleri, "Chronic diarrhea: a review on pathophysiology and management for the clinical gastroenterologist," Clin. Gastroenterol. Hepatology, Mar. 2004, 2(3):198-206.
Cleary, "Clostridium difficile-associated diarrhea and colitis: clinical manifestations, diagnosis, and treatment," Dis. Colon Rectum, Nov. 1998, 41(11):1435-1449.
Juckett et al., "Evaluation of chronic diarrhea," Am. Fam. Physician, Nov. 15, 2011, 84(10):1119-1126.
Kelly et al., "Update on Fecal Microbiota Transplantation 2015: Indications, Methodologies, Mechanisms, and Outlook," Gastroenterology, Jul. 2015, 149(1):223-237.
Leekha et al., "Asymptomatic Clostridium difficile colonization in a tertiary care hospital: admission prevalence and risk factors," Am. J. Infect. Control, May 2013, 41(5):390-393.
Riggs et al., "Asymptomatic carriers are a potential source for transmission of epidemic and nonepidemic Clostridium difficile strains among long-term care facility residents," Clin. Infect. Diseases, Oct. 15, 2007, 45(8):992-998.
Abubucker et al., "Metabolic reconstruction for metagenomic data and its application to the human microbiome," PLOS Comput Biol, Jun. 2012, 8:e1002358.
Aspinall et al., "New selective medium for isolating Clostridium difficile from faeces," J Clin Pathol, Sep. 1992, 45:812-814.
Backhed et al., "Mechanisms underlying the resistance to diet-induced obesity in germ-free mice," Proc Natl Acad Sci U S A, Jan. 2007, 104:979-984.

(Continued)

*Primary Examiner* — Michael Barker
*Assistant Examiner* — Sharon M. Papciak
(74) *Attorney, Agent, or Firm* — Fish & Richardson P.C.

(57) ABSTRACT

This document provides biomarkers of gut microbiota dysbiosis. Bacteria that are increased or decreased in gut microbiota dysbiosis can be used as biomarkers to predict dysbiosis in patients with diarrhea and/or to predict susceptibility to *Clostridium difficile* infection (CDI). In addition, provided herein are compositions including at least three bacteria that are decreased in gut microbiota dysbiosis which can be used, for example, to restore heathy gut microbiota (e.g., by probiotic or by fecal microbiota transplant) to treat CDI.

18 Claims, 36 Drawing Sheets

(56) References Cited

OTHER PUBLICATIONS

Bolger et al., "Trimmomatic: a flexible trimmer for Illumina sequence data," Bioinformatics, Aug. 2014, 30:2114-2120.
Bouillant et al., "Integration of metabolism and virulence in Clostridium difficile," Res Microbiol., May 2015, 166:375-383.
Bouillaut et al., "Proline-dependent regulation of Clostridium difficile Stickland metabolism," J Bacteriol., Feb. 2013, 195:844-854.
Buffie et al., "Precision microbiome reconstitution restores bile acid mediated resistance to Clostridium difficile," Nature, Jan. 2015, 517:205-208.
Chen et al., "Impact of demographics on human gut microbial diversity in a US Midwest population," PeerJ, Jan. 2016, e1514.
Dubberke et al., "Development and validation of Clostridium difficile infection risk prediction model," Infection Contol and Hospital Epidemiology, Apr. 2011, 32(4): 360-366.
Efron et al., "Improvements on cross-validation: the 632+ bootstrap method," J Am Stat Assoc, Jun. 1997, 92:548-560.
Ferreyra et al., "Gut microbiota-produced succinate promotes C. difficile infection after antibiotic treatment or motility disturbance," Cell Host Microbe, Dec. 2014, 16:770-777.
Humbert et al., "Bile acid profiling in human biological samples: comparison of extraction procedures and application to normal and cholestatic patients," J Chromatogr B Analyt Technol Biomed Life Sci, Jun. 2012, 899:135-145.
Jackson et al., "Analysis of proline reduction in the nosocomial pathogen Clostridium difficile," J Bacteriol., Dec. 2006, 188:8487-8495.
Karasawa et al., "A defined growth medium for Clostridium difficile," Microbiology, Feb. 1995, 141:371-375.
Kursa et al., "Feature selection with the Boruta package," J Stat Softw, Sep. 2010, 36:1-13.
Lawley et al., "Targeted restoration of the intestinal microbiota with a simple, defined bacteriotherapy resolves relapsing Clostridium difficile disease in mice," PLoS Pathog., Oct. 2012, 8(10): e1002995.
Lessa et al., "Burden of Clostridium difficile infection in the United States," N Engl J Med, Feb. 2015, 372:825-834.
Love et al., "Moderated estimation of fold change and dispersion for RNA-seq data with DESeq2," Genome Biol, 2014, 15:550.
Marcobal et al., "A metabolomic view of how the human gut microbiota impacts the host metabolome using humanized and gnotobiotic mice," ISME J., Oct. 2013, 7:1933-1943.
PCT International Preliminary Report on Patentability in International Appln. No. PCT/US2016/053073, dated Mar. 27, 2018, 11 pages.
PCT International Search Report and Written Opinion in International Appln. No. PCT/US2016/053073, dated Dec. 15, 2016, 16 pages.
Reigstad et al., "Gut microbes promote colonic serotonin production through an effect of short-chain fatty acids on enterochromaffin cells," Faseb J., Apr. 2015, 29:1395-1403.
Ridaura et al.,"Gut microbiota from twins discordant for obesity modulate metabolism in mice," Science, Sep. 2013, 341:1241214.
Ridlon et al., "The human gut sterolbiome: bile acid-microbiome endocrine aspects and therapeutics," Acta Pharmaceutica Sinica B, Feb. 2015, 5(2): 99-105.
Rousseeuw et al., "Silhouettes: a graphical aid to the interpretation and validation of cluster analysis," J Comput Appl Math, Nov. 1987, 20:53-65.
Rupnik et al., "Clostridium difficile infection: new developments in epidemiology and pathogenesis," Nat Rev Microbiol., Jul. 2009, 7:526-36.
Saric et al., "Metabolic profiling of an Echinostoma caproni infection in the mouse for biomarker discovery;" PLoS Negl Trop Dis., Jul. 2008, 2:e254.
Segata et al.,"Metagenomic biomarker discovery and explanation," Genome Biol, Jun. 2011, 12:R60-R60.
Sloan et al., "Comparison of real-time PCR for detection of the tedC gene with four toxin immunoassays and culture in diagnosis of Clostridium difficile infection," J Clin Microbiol, Jun. 2008, 46:1996-2001.
Smith et al., "XCMS: processing mass spectrometry data for metabolite profiling using nonlinear peak alignment, matching, and identification," Anal Chem, Feb. 2006, 78:779-787.
Sorg et al., "Bile salts and glycine as cogerminants for Clostridium difficile spores," J Bacteriol., Apr. 2008, 190: 2505-2512.
Sorg et al., "Chenodeoxycholate is an inhibitor of Clostridium difficile spore germination," J Bacteriol., Feb. 2009, 191:1115-1117.
Sorg et al., "Inhibiting the initiation of Clostridium difficile spore germination using analogs of chenodeoxycholic acid, a bile acid," J Bacteriol.,Oct. 2010, 192:4983-4990.
Theriot et al., "Antibiotic-induced shifts in the mouse gut microbiome and metabolome increase susceptibility to Clostridium difficile infection," Nat Commun, 2014, 5:3114-3114.
Tibshirani et al., "Estimating the number of clusters in a data set via the gap statistic," J Roy Stat Soc B, 2001, 63:411-423.
Turnbaugh et al., "The effect of diet on the human gut microbiome: a metagenomic analysis in humanized gnotobiotic mice," Sci Transl Med., Nov. 2009, 1:6ra14.
van Nood et al., "Duodenal infusion of donor feces for recurrent Clostridium difficile," N Engl J Med, Jan. 2013, 368:407-415.
Weingarden et al., "Microbiota transplantation restores normal fecal bile acid composition in recurrent Clostridium difficile infection, " Am J Physiol Gastrointest Liver Physiol., Feb. 2014, 306:G310-319.
Wu et al., "An optimised sample preparation method for NMR-based faecal metabonomic analysis," Analyst, May 2010, 135:1023-1030.
Zhao et al., "Gut microbiota composition modifies fecal metabolic profiles in mice," J Proteome Res., Jun. 2013, 12:2987-2999.

\* cited by examiner

FIG. 12

| Taxa Present in Humans | Transferred to Mice at a Family Level? |
|---|---|
| Bacteria; Proteobacteria; Betaproteobacteria; Neisseriales; Neisseriaceae | N |
| Bacteria; Proteobacteria; Gammaproteobacteria; Enterobacteriales; Enterobacteriaceae | Y |
| Bacteria; Firmicutes; Clostridia; Clostridiales; Veillonellaceae | Y |
| Bacteria; Fusobacteria; Fusobacteriia; Fusobacteriales; Fusobacteriaceae | N |
| Bacteria; Proteobacteria; Betaproteobacteria; Burkholderiales; | Y |
| Bacteria; Firmicutes; Bacilli; Lactobacillales; Lactobacillaceae | Y |
| Bacteria; Proteobacteria; Deltaproteobacteria; Desulfovibrionales; Desulfovibrionaceae | Y |
| Bacteria; Proteobacteria; Epsilonproteobacteria; Campylobacterales; Campylobacteraceae | N |
| Bacteria; Bacteroidetes; Bacteroidia; Bacteroidales; S24-7 | Y |
| Bacteria; Bacteroidetes; Bacteroidia; Bacteroidales; Bacteroidaceae | Y |
| Bacteria; Bacteroidetes; Bacteroidia; Bacteroidales; Prevotellaceae | Y |
| Bacteria; Firmicutes; Bacilli; Lactobacillales; Streptococcaceae | Y |
| Bacteria; Actinobacteria; Actinobacteria; Actinomycetales; Micrococcaceae | Y |
| Bacteria; Bacteroidetes; Bacteroidia; Bacteroidales; [Barnesiellaceae] | Y |
| Bacteria; Firmicutes; Clostridia; Clostridiales | Y |
| Bacteria; Firmicutes; Clostridia; Clostridiales; Lachnospiraceae | Y |
| Bacteria; Firmicutes; Clostridia; Clostridiales; Ruminococcaceae | Y |
| Bacteria; Proteobacteria; Betaproteobacteria | Y |
| Bacteria; Proteobacteria; Gammaproteobacteria; Aeromonadales; Aeromonadaceae | Y |
| Bacteria; Verrucomicrobia; Verrucomicrobiae; Verrucomicrobiales; Verrucomicrobiaceae | Y |
| Bacteria; Actinobacteria; Actinobacteria; Bifidobacteriales; Bifidobacteriaceae | Y |
| Bacteria; Actinobacteria; Coriobacteriia; Coriobacteriales; Coriobacteriaceae | Y |
| Bacteria; Firmicutes; Bacilli; Lactobacillales; Enterococcaceae | Y |
| Bacteria; Firmicutes; Bacilli; Lactobacillales; Carnobacteriaceae | Y |
| Bacteria; Bacteroidetes; Bacteroidia; Bacteroidales; Porphyromonadaceae | Y |
| Bacteria; Actinobacteria; Actinobacteria; Actinomycetales; Corynebacteriaceae | Y |
| Bacteria; Firmicutes; Bacilli; Bacillales; Planococcaceae | N |
| Bacteria; Firmicutes; Erysipelotrichi; Erysipelotrichales; Erysipelotrichaceae | Y |
| Bacteria; Proteobacteria; Gammaproteobacteria; Pseudomonadales; Moraxellaceae | Y |

FIG. 13

| Mouse ID | Risk | Donor ID | Inflammation in the Lamina Propria | Maximum PMN/HPF | Depth of Inflammation | TOTAL |
|---|---|---|---|---|---|---|
| 1A | dysbiotic | A | 3 | 4 | 3 | 10 |
| 1B | dysbiotic | A | 2 | 1 | 2 | 5 |
| 1C | dysbiotic | A | 1 | 1 | 3 | 5 |
| 1D | dysbiotic | A | 2 | 3 | 2 | 7 |
| 2A | dysbiotic | B | 2 | 4 | 2 | 8 |
| 2B | dysbiotic | B | 3 | 3 | 2 | 8 |
| 2C | dysbiotic | B | 3 | 4 | 2 | 9 |
| 2D | dysbiotic | B | 3 | 4 | 2 | 9 |
| 2E | dysbiotic | B | 3 | 4 | 3 | 10 |
| 2F | dysbiotic | B | 3 | 4 | 2 | 9 |
| 3A | healthy-like | C | 0 | 0 | 0 | 0 |
| 3B | healthy-like | C | 1 | 2 | 2 | 5 |
| 3C | healthy-like | C | 1 | 1 | 0 | 2 |
| 3D | healthy-like | C | 1 | 1 | 0 | 2 |
| 3E | healthy-like | C | 1 | 1 | 0 | 2 |
| 4A | healthy-like | D | 0 | 0 | 0 | 0 |
| 4B | healthy-like | D | 0 | 0 | 0 | 0 |
| 4C | healthy-like | D | 0 | 0 | 0 | 0 |
| 4D | healthy-like | D | 0 | 0 | 0 | 0 |
| 4E | healthy-like | D | 0 | 0 | 0 | 0 |
| 4F | healthy-like | D | 0 | 0 | 0 | 0 |

FIG. 14A

| Pathway | baseMean | log2FoldChange | padj |
|---|---|---|---|
| PWY_7254_TCA_cycle_VII_acetate_producers_ | 9736.88 | 6.73 | 5.69E-38 |
| PWY_922_mevalonate_pathway_I | 89.23 | 3.74 | 2.32E-09 |
| PWY_5910_superpathway_of_geranylgeranyldiphosphate_biosynthesis_I_via_mevalonate_ | 121.10 | 3.63 | 1.32E-09 |
| PWY_7391_isoprene_biosynthesis_II_engineered_ | 57.77 | 3.62 | 1.09E-05 |
| PWY_5109_2_methylbutanoate_biosynthesis | 241.55 | 3.06 | 2.61E-16 |
| PWY_5173_superpathway_of_acetyl_CoA_biosynthesis | 2757.97 | 2.99 | 1.66E-07 |
| PWY_7117_C4_photosynthetic_carbon_assimilation_cycle_PEPCK_type | 5508.76 | 2.95 | 5.82E-16 |
| PWY_5677_succinate_fermentation_to_butanoate | 45.46 | 2.91 | 1.82E-06 |
| LACTOSECAT_PWY_lactose_and_galactose_degradation_I | 5229.57 | 2.86 | 7.53E-32 |
| PWY_1861_formaldehyde_assimilation_II_RuMP_Cycle_ | 1772.47 | 2.80 | 2.41E-09 |
| PWY_5791_1_4_dihydroxy_2_naphthoate_biosynthesis_II_plants_ | 372.80 | 2.76 | 2.04E-04 |
| PWY_5837_1_4_dihydroxy_2_naphthoate_biosynthesis_I | 372.80 | 2.76 | 2.04E-04 |
| P163_PWY_L_lysine_fermentation_to_acetate_and_butanoate | 4640.04 | 2.72 | 3.09E-21 |
| PWY_241_C4_photosynthetic_carbon_assimilation_cycle_NADP_ME_type | 3928.84 | 2.70 | 7.86E-17 |
| PWY_5863_superpathway_of_phylloquinol_biosynthesis | 390.46 | 2.65 | 3.21E-04 |
| PWY_6549_L_glutamine_biosynthesis_III | 5509.91 | 2.51 | 6.92E-36 |
| PWY_7456_mannan_degradation | 5576.37 | 2.47 | 1.90E-12 |
| PWY_5754_4_hydroxybenzoate_biosynthesis_I_eukaryotes_ | 1276.29 | 2.38 | 1.52E-09 |
| PWY_6572_chondroitin_sulfate_degradation_I_bacterial_ | 24.32 | 2.36 | 5.63E-08 |
| PWY_7288_fatty_acid_beta_oxidation_peroxisome_yeast_ | 407.27 | 2.27 | 1.91E-10 |
| PWY_5676_acetyl_CoA_fermentation_to_butanoate_II | 6362.87 | 2.24 | 3.52E-70 |
| HEXITOLDEGSUPER_PWY_superpathway_of_hexitol_degradation_bacteria_ | 513.82 | 2.21 | 3.90E-06 |
| PWY_6478_GDP_D_glycero_alpha_D_manno_heptose_biosynthesis | 31.70 | 2.19 | 1.16E-07 |
| P562_PWY_myo_inositol_degradation_I | 690.83 | 2.18 | 2.31E-09 |
| PWY_4041_gamma_glutamyl_cycle | 486.87 | 2.14 | 5.93E-06 |
| PWY66_391_fatty_acid_beta_oxidation_VI_peroxisome_ | 715.88 | 2.09 | 2.30E-10 |
| PWY_7220_adenosine_deoxyribonucleotides_de_novo_biosynthesis_II | 12237.44 | 2.06 | 2.02E-22 |
| PWY_7222_guanosine_deoxyribonucleotides_de_novo_biosynthesis_II | 12237.44 | 2.06 | 2.02E-22 |
| GLUCARDEG_PWY_D_glucarate_degradation_I | 311.09 | 2.05 | 1.06E-12 |
| PWY_6588_pyruvate_fermentation_to_acetone | 3075.60 | 2.00 | 3.42E-12 |
| RUMP_PWY_formaldehyde_oxidation_I | 769.95 | 1.97 | 1.58E-06 |
| PWY_4984_urea_cycle | 3246.49 | 1.97 | 4.56E-15 |
| P461_PWY_hexitol_fermentation_to_lactate_formate_ethanol_and_acetate | 439.90 | 1.93 | 1.02E-03 |
| PWY_621_sucrose_degradation_III_sucrose_invertase_ | 1296.11 | 1.91 | 6.97E-05 |
| P124_PWY_Bifidobacterium_shunt | 12605.25 | 1.84 | 1.15E-14 |
| P122_PWY_heterolactic_fermentation | 11318.71 | 1.84 | 1.09E-13 |
| PWY_5138_unsaturated_even_numbered_fatty_acid_beta_oxidation | 667.02 | 1.84 | 1.92E-08 |
| PWY_7413_dTDP_6_deoxy_alpha_D_allose_biosynthesis | 15.33 | 1.82 | 1.33E-02 |
| ASPASN_PWY_superpathway_of_L_aspartate_and_L_asparagine_biosynthesis | 16386.35 | 1.75 | 2.44E-14 |
| P108_PWY_pyruvate_fermentation_to_propanoate_I | 19222.52 | 1.75 | 3.15E-25 |
| PWY_7234_inosine_5_phosphate_biosynthesis_III | 1096.41 | 1.72 | 7.33E-06 |
| PWY_5861_superpathway_of_demethylmenaquinol_8_biosynthesis | 407.81 | 1.71 | 1.33E-02 |
| PWY_5897_superpathway_of_menaquinol_11_biosynthesis | 530.87 | 1.71 | 1.08E-02 |
| PWY_5898_superpathway_of_menaquinol_12_biosynthesis | 530.87 | 1.71 | 1.08E-02 |
| PWY_5899_superpathway_of_menaquinol_13_biosynthesis | 530.87 | 1.71 | 1.08E-02 |
| COBALSYN_PWY_adenosylcobalamin_salvage_from_cobinamide_I | 1525.05 | 1.70 | 7.15E-22 |
| P42_PWY_incomplete_reductive_TCA_cycle | 15645.05 | 1.67 | 4.58E-13 |
| PWY_5840_superpathway_of_menaquinol_7_biosynthesis | 559.27 | 1.62 | 1.47E-02 |
| CITRULBIO_PWY_L_citrulline_biosynthesis | 3764.76 | 1.61 | 1.47E-20 |

FIG. 14B

| Pathway | baseMean | log2FoldChange | padj |
|---|---|---|---|
| PWY_6305_putrescine_biosynthesis_IV | 2640.56 | 1.60 | 4.30E-24 |
| FERMENTATION_PWY_mixed_acid_fermentation | 7531.52 | 1.59 | 1.35E-09 |
| PWY_6883_pyruvate_fermentation_to_butanol_II | 1175.63 | 1.59 | 1.35E-09 |
| PWY_5690_TCA_cycle_II_plants_and_fungi_ | 12806.45 | 1.56 | 4.06E-12 |
| PWY_6901_superpathway_of_glucose_and_xylose_degradation | 24465.06 | 1.56 | 1.13E-22 |
| TCA_TCA_cycle_I_prokaryotic_ | 17101.59 | 1.55 | 6.37E-21 |
| PWY_5913_TCA_cycle_VI_obligate_autotrophs_ | 4733.90 | 1.55 | 2.19E-07 |
| PWY_5838_superpathway_of_menaquinol_8_biosynthesis_I | 522.35 | 1.54 | 2.00E-02 |
| GALACTARDEG_PWY_D_galactarate_degradation_I | 534.41 | 1.45 | 1.90E-05 |
| GLUCARGALACTSUPER_PWY_superpathway_of_D_glucarate_and_D_galactarate_degradation | 534.41 | 1.45 | 1.90E-05 |
| PWY_6269_adenosylcobalamin_salvage_from_cobinamide_II | 1013.38 | 1.42 | 1.17E-13 |
| P125_PWY_superpathway_of_R_R_butanediol_biosynthesis | 471.95 | 1.41 | 3.03E-03 |
| PWY_7431_aromatic_biogenic_amine_degradation_bacteria_ | 742.45 | 1.40 | 3.30E-02 |
| PWY_6595_superpathway_of_guanosine_nucleotides_degradation_plants_ | 3715.65 | 1.40 | 3.37E-04 |
| PENTOSE_P_PWY_pentose_phosphate_pathway | 22328.25 | 1.37 | 2.68E-10 |
| THISYNARA_PWY_superpathway_of_thiamin_diphosphate_biosynthesis_III_eukaryotes_ | 2940.14 | 1.34 | 1.74E-04 |
| PWY_2221_Entner_Doudoroff_pathway_III_semi_phosphorylative_ | 215.54 | 1.33 | 4.20E-04 |
| PWY_6612_superpathway_of_tetrahydrofolate_biosynthesis | 749.32 | 1.31 | 8.35E-04 |
| PWY0_1479_tRNA_processing | 5211.65 | 1.31 | 3.82E-15 |
| PWY_6396_superpathway_of_2_3_butanediol_biosynthesis | 729.96 | 1.29 | 1.74E-04 |
| PWY_7384_anaerobic_energy_metabolism_invertebrates_mitochondrial_ | 5342.10 | 1.28 | 1.81E-12 |
| FOLSYN_PWY_superpathway_of_tetrahydrofolate_biosynthesis_and_salvage | 1073.69 | 1.27 | 8.62E-04 |
| PWY_6125_superpathway_of_guanosine_nucleotides_de_novo_biosynthesis_II | 10383.98 | 1.25 | 1.84E-16 |
| GLUCONEO_PWY_gluconeogenesis_I | 44782.81 | 1.24 | 2.72E-31 |
| PWY_6969_TCA_cycle_V_2_oxoglutarate_ferredoxin_oxidoreductase_ | 20147.65 | 1.22 | 9.23E-32 |
| CENTFERM_PWY_pyruvate_fermentation_to_butanoate | 2509.33 | 1.20 | 2.11E-06 |
| PRPP_PWY_superpathway_of_histidine_purine_and_pyrimidine_biosynthesis | 3217.58 | 1.20 | 2.63E-06 |
| PWY_5509_adenosylcobalamin_biosynthesis_from_cobyrinate_a_c_diamide_I | 883.92 | 1.17 | 2.32E-09 |
| PWY_6692_Fe_II_oxidation | 8929.64 | 1.15 | 1.82E-04 |
| PWY_6471_peptidoglycan_biosynthesis_IV_Enterococcus_faecium_ | 1507.54 | 1.11 | 5.56E-05 |
| PWY4LZ_257_superpathway_of_fermentation_Chlamydomonas_reinhardtii_ | 18337.72 | 1.11 | 3.11E-09 |
| PWY_6590_superpathway_of_Clostridium_acetobutylicum_acidogenic_fermentation | 3000.89 | 1.09 | 8.01E-06 |
| PWY_7279_aerobic_respiration_II_cytochrome_c_yeast_ | 8242.64 | 1.09 | 1.41E-04 |
| PWY_7228_superpathway_of_guanosine_nucleotides_de_novo_biosynthesis_I | 10779.53 | 1.07 | 1.25E-17 |
| PWY_7237_myo_chiro_and_scillo_inositol_degradation | 8853.64 | 1.04 | 1.15E-05 |
| PWY_7282_4_amino_2_methyl_5_phosphomethylpyrimidine_biosynthesis_yeast_ | 4376.34 | 1.03 | 2.53E-04 |
| PWY0_1298_superpathway_of_pyrimidine_deoxyribonucleosides_degradation | 3361.11 | 1.02 | 7.74E-07 |
| PWY_7209_superpathway_of_pyrimidine_ribonucleosides_degradation | 1636.61 | 1.00 | 1.53E-07 |

FIG. 15A

| Pathway | baseMean | log2FoldChange | padj |
|---|---|---|---|
| PWY_6891_thiazole_biosynthesis_II_Bacillus_ | 1038.04 | 12.90 | 3.86E-30 |
| PWY_6895_superpathway_of_thiamin_diphosphate_biosynthesis_II | 2298.58 | 12.48 | 7.68E-67 |
| PWY_6731_starch_degradation_III | 530.72 | 12.07 | 1.76E-25 |
| PWY_7315_dTDP_N_acetylthomosamine_biosynthesis | 417.04 | 11.80 | 3.81E-24 |
| PWY_5088_L_glutamate_degradation_VIII_to_propanoate_ | 1268.20 | 11.39 | 9.67E-68 |
| PWY_6318_L_phenylalanine_degradation_IV_mammalian_via_side_chain_ | 1505.51 | 11.36 | 5.23E-73 |
| GLUDEG_II_PWY_L_glutamate_degradation_VII_to_butanoate_ | 562.52 | 10.94 | 6.15E-42 |
| METH_ACETATE_PWY_methanogenesis_from_acetate | 2036.93 | 10.36 | 3.24E-125 |
| PWY_1622_formaldehyde_assimilation_I_serine_pathway_ | 124.61 | 10.19 | 3.42E-16 |
| PWY_4702_phytate_degradation_I | 116.01 | 10.08 | 1.15E-15 |
| PWY_6165_chorismate_biosynthesis_II_archaea_ | 97.88 | 9.93 | 2.13E-15 |
| PWY_6803_phosphatidylcholine_acyl_editing | 3352.12 | 9.89 | 4.66E-114 |
| P162_PWY_L_glutamate_degradation_V_via_hydroxyglutarate_ | 1800.47 | 9.78 | 4.52E-153 |
| PWY0_1261_anhydromuropeptides_recycling | 389.09 | 9.71 | 2.24E-43 |
| GLYOXYLATE_BYPASS_glyoxylate_cycle | 579.41 | 9.70 | 5.72E-17 |
| PWY_5508_adenosylcobalamin_biosynthesis_from_cobyrinate_a_c_diamide_II | 102.84 | 9.45 | 5.20E-12 |
| 7ALPHADEHYDROX_PWY_cholate_degradation_bacteria_anaerobic_ | 66.30 | 9.28 | 1.93E-12 |
| PWY_7295_L_arabinose_degradation_IV | 53.34 | 8.99 | 1.70E-11 |
| CODH_PWY_reductive_acetyl_coenzyme_A_pathway | 54.51 | 8.89 | 6.98E-11 |
| PWY_181_photorespiration | 240.78 | 8.80 | 7.87E-42 |
| TYRFUMCAT_PWY_L_tyrosine_degradation_I | 96.91 | 8.75 | 2.25E-14 |
| NAGLIPASYN_PWY_lipid_IVA_biosynthesis | 129.27 | 8.65 | 6.11E-18 |
| PWY_622_starch_biosynthesis | 51.22 | 8.53 | 2.22E-09 |
| TCA_GLYOX_BYPASS_superpathway_of_glyoxylate_bypass_and_TCA | 484.42 | 8.47 | 4.17E-13 |
| PWY_6728_methylaspartate_cycle | 34.49 | 8.47 | 5.27E-10 |
| PWY_561_superpathway_of_glyoxylate_cycle_and_fatty_acid_degradation | 610.91 | 8.29 | 2.71E-12 |
| P105_PWY_TCA_cycle_IV_2_oxoglutarate_decarboxylase_ | 900.53 | 8.22 | 7.24E-21 |
| PWY_6863_pyruvate_fermentation_to_hexanol | 25.72 | 8.22 | 1.43E-09 |
| GLYCOLYSIS_TCA_GLYOX_BYPASS_superpathway_of_glycolysis_pyruvate_dehydrogenase_TCA_and_glyoxylate_bypass | 847.34 | 8.08 | 7.38E-11 |
| PWY_5273_p_cumate_degradation | 25.91 | 7.98 | 1.79E-08 |
| PWY_6518_glycocholate_metabolism_bacteria_ | 526.44 | 7.97 | 2.96E-45 |
| PWY490_3_nitrate_reduction_VI_assimilatory_ | 349.72 | 7.93 | 1.41E-40 |
| PWY_6708_ubiquinol_8_biosynthesis_prokaryotic_ | 24.64 | 7.89 | 3.21E-08 |
| ALL_CHORISMATE_PWY_superpathway_of_chorismate_metabolism | 21.99 | 7.84 | 3.12E-08 |
| PWY0_1277_3_phenylpropanoate_and_3_3_hydroxyphenyl_propanoate_degradation | 22.00 | 7.71 | 9.34E-08 |
| PWY_7165_L_ascorbate_biosynthesis_VI_engineered_pathway_ | 20.39 | 7.67 | 9.36E-08 |
| PWY_5055_nicotinate_degradation_III | 16.10 | 7.66 | 3.56E-08 |
| PWY_6415_L_ascorbate_biosynthesis_V | 30.38 | 7.45 | 1.52E-06 |
| PWY3O_1109_superpathway_of_4_hydroxybenzoate_biosynthesis_yeast_ | 18.28 | 7.45 | 3.86E-07 |
| UBISYN_PWY_superpathway_of_ubiquinol_8_biosynthesis_prokaryotic_ | 15.71 | 7.39 | 3.52E-07 |
| PWY_7007_methyl_ketone_biosynthesis | 2240.10 | 7.38 | 2.04E-98 |
| PWY_6596_adenosine_nucleotides_degradation_I | 48.96 | 7.36 | 1.06E-12 |

FIG. 15B

| Pathway | baseMean | log2FoldChange | padj |
|---|---|---|---|
| DHGLUCONATE_PYR_CAT_PWY_glucose_degradation_oxidative_ | 14.54 | 7.31 | 5.27E-07 |
| P261_PWY_coenzyme_M_biosynthesis_I | 12.03 | 7.17 | 7.44E-07 |
| KDO_NAGLIPASYN_PWY_superpathway_of_Kdo_2_lipid_A_biosynthesis | 13.44 | 7.09 | 2.07E-06 |
| PWY_2723_trehalose_degradation_V | 21.13 | 7.04 | 7.54E-06 |
| PWY_5507_adenosylcobalamin_biosynthesis_I_early_cobalt_insertion_ | 10.91 | 7.00 | 1.99E-06 |
| URSIN_PWY_ureide_biosynthesis | 9.68 | 6.97 | 1.63E-06 |
| HCAMHPDEG_PWY_3_phenylpropanoate_and_3_3_hydroxyphenyl_propanoate_degradation_to_2_oxopent_4_enoate | 13.04 | 6.92 | 5.61E-06 |
| PWY_6690_cinnamate_and_3_hydroxycinnamate_degradation_to_2_oxopent_4_enoate | 13.04 | 6.92 | 5.61E-06 |
| PWY_5044_purine_nucleotides_degradation_I_plants_ | 93.08 | 6.89 | 6.11E-18 |
| PWY_5181_toluene_degradation_III_aerobic_via_p_cresol_ | 13.57 | 6.82 | 1.08E-05 |
| PWY_5420_catechol_degradation_II_meta_cleavage_pathway_ | 9.02 | 6.69 | 9.42E-06 |
| PWY_7317_superpathway_of_dTDP_glucose_derived_O_antigen_building_blocks_biosynthesis | 8.82 | 6.63 | 1.25E-05 |
| PWY_6906_chitin_derivatives_degradation | 153.00 | 6.55 | 3.02E-37 |
| P165_PWY_superpathway_of_purines_degradation_in_plants_ | 6.76 | 6.53 | 1.13E-05 |
| PWY_7371_1_4_dihydroxy_6_naphthoate_biosynthesis_II | 6.75 | 6.53 | 1.19E-05 |
| PWY_5415_catechol_degradation_I_meta_cleavage_pathway_ | 17.14 | 6.46 | 1.66E-07 |
| PWY_6060_malonate_degradation_II_biotin_dependent_ | 6.49 | 6.46 | 1.66E-05 |
| PWY_5742_L_arginine_degradation_IX_arginine_pyruvate_transaminase_pathway_ | 5.94 | 6.39 | 1.94E-05 |
| ECASYN_PWY_enterobacterial_common_antigen_biosynthesis | 8.45 | 6.38 | 4.69E-05 |
| PWY_5265_peptidoglycan_biosynthesis_II_staphylococci_ | 7.37 | 6.35 | 4.32E-05 |
| PWY_6565_superpathway_of_polyamine_biosynthesis_III | 82.63 | 6.28 | 1.43E-31 |
| PWY_5532_adenosine_nucleotides_degradation_IV | 13.14 | 6.26 | 8.03E-08 |
| PWY_6769_rhamnogalacturonan_type_I_degradation_I_fungi_ | 5.50 | 6.20 | 5.10E-05 |
| PWY_5178_toluene_degradation_IV_aerobic_via_catechol_ | 6.33 | 6.16 | 8.69E-05 |
| PWY_5419_catechol_degradation_to_2_oxopent_4_enoate_II | 5.79 | 6.15 | 7.71E-05 |
| PWY_7374_1_4_dihydroxy_6_naphthoate_biosynthesis_I | 4.85 | 6.12 | 6.12E-05 |
| PWY_6953_dTDP_3_acetamido_3_6_dideoxy_alpha_D_galactose_biosynthesis | 30.20 | 6.09 | 3.69E-14 |
| PWY_6981_chitin_biosynthesis | 7.16 | 6.06 | 1.63E-04 |
| PWY0_1241_ADP_L_glycero_beta_D_manno_heptose_biosynthesis | 53.82 | 5.95 | 1.93E-27 |
| P23_PWY_reductive_TCA_cycle_I | 890.92 | 5.94 | 7.56E-40 |
| GLYCOL_GLYOXDEG_PWY_superpathway_of_glycol_metabolism_and_degradation | 346.54 | 5.90 | 8.60E-46 |
| REDCITCYC_TCA_cycle_VIII_helicobacter_ | 838.70 | 5.90 | 9.72E-30 |
| PWY_6107_chlorosalicylate_degradation | 7.23 | 5.89 | 3.41E-04 |
| LPSSYN_PWY_superpathway_of_lipopolysaccharide_biosynthesis | 8.22 | 5.80 | 5.43E-04 |
| PWY_5747_2_methylcitrate_cycle_II | 13.78 | 5.78 | 3.86E-05 |
| PWY_5417_catechol_degradation_III_ortho_cleavage_pathway_ | 7.70 | 5.76 | 5.98E-04 |
| PWY_5431_aromatic_compounds_degradation_via_beta_ketoadipate | 7.70 | 5.76 | 5.98E-04 |
| PWY_7373_superpathway_of_demethylmenaquinol_6_biosynthesis_II | 3.63 | 5.76 | 2.26E-04 |
| PWY0_1338_polymyxin_resistance | 10.16 | 5.67 | 1.67E-05 |
| PWY_7414_dTDP_alpha_D_mycaminose_biosynthesis | 4.37 | 5.66 | 4.72E-04 |

FIG. 15C

| Pathway | baseMean | log2FoldChange | padj |
|---|---|---|---|
| PWY_6562_norspermidine_biosynthesis | 54.18 | 5.66 | 1.74E-23 |
| PWY_6823_molybdenum_cofactor_biosynthesis | 83.08 | 5.64 | 4.99E-21 |
| PWY_5183_superpathway_of_aerobic_toluene_degradation | 5.58 | 5.58 | 8.67E-04 |
| PWY5F9_12_biphenyl_degradation | 11.85 | 5.55 | 1.48E-03 |
| UDPNACETYLGALSYN_PWY_UDP_N_acetyl_D_glucosamine_biosynthesis_II | 70.14 | 5.55 | 1.05E-21 |
| PWY0_42_2_methylcitrate_cycle_I | 14.87 | 5.51 | 6.59E-06 |
| PWY_6215_4_chlorobenzoate_degradation | 8.36 | 5.47 | 1.57E-03 |
| PWY_5531_chlorophyllide_a_biosynthesis_II_anaerobic_ | 5.31 | 5.41 | 1.43E-03 |
| PWY_7159_chlorophyllide_a_biosynthesis_III_aerobic_light_independent_ | 5.31 | 5.41 | 1.43E-03 |
| CATECHOL_ORTHO_CLEAVAGE_PWY_catechol_degradation_to_beta_ketoadipate | 5.53 | 5.40 | 1.54E-03 |
| PWY_5514_UDP_N_acetyl_D_galactosamine_biosynthesis_II | 105.48 | 5.38 | 1.74E-26 |
| PWY_7318_dTDP_3_acetamido_3_6_dideoxy_alpha_D_glucose_biosynthesis | 34.99 | 5.36 | 6.63E-12 |
| NPGLUCAT_PWY_Entner_Doudoroff_pathway_II_non_phosphorylative_ | 10.19 | 5.35 | 6.32E-08 |
| PWY_7316_dTDP_N_acetylviosamine_biosynthesis | 435.21 | 5.35 | 4.30E-77 |
| CHLOROPHYLL_SYN_chlorophyllide_a_biosynthesis_I_aerobic_light_dependent_ | 4.79 | 5.31 | 1.83E-03 |
| PWY_5430_meta_cleavage_pathway_of_aromatic_compounds | 2.93 | 5.27 | 1.38E-03 |
| DENITRIFICATION_PWY_nitrate_reduction_I_denitrification_ | 3.17 | 5.21 | 1.83E-03 |
| PWY_6182_superpathway_of_salicylate_degradation | 6.59 | 5.20 | 3.03E-03 |
| PWY_5529_superpathway_of_bacteriochlorophyll_a_biosynthesis | 3.62 | 5.08 | 3.11E-03 |
| PWY_6886_1_butanol_autotrophic_biosynthesis | 2.24 | 5.00 | 2.64E-03 |
| PWY_5005_biotin_biosynthesis_II | 37.37 | 4.95 | 7.02E-09 |
| PWY_5855_ubiquinol_7_biosynthesis_prokaryotic_ | 25.24 | 4.89 | 2.05E-06 |
| PWY_5857_ubiquinol_10_biosynthesis_prokaryotic_ | 25.24 | 4.89 | 2.05E-06 |
| GLYCOCAT_PWY_glycogen_degradation_I_bacterial_ | 43.47 | 4.89 | 1.64E-17 |
| 3_HYDROXYPHENYLACETATE_DEGRADATION_PWY_4_hydroxyphenylacetate_degradation | 20.60 | 4.84 | 9.24E-08 |
| ARGDEG_IV_PWY_L_arginine_degradation_VIII_arginine_oxidase_pathway_ | 1.67 | 4.78 | 4.11E-03 |
| P281_PWY_3_phenylpropanoate_degradation | 2.56 | 4.69 | 7.52E-03 |
| PWY_5656_mannosylglycerate_biosynthesis_I | 2.56 | 4.68 | 7.90E-03 |
| PWY_1361_benzoyl_CoA_degradation_I_aerobic_ | 2.73 | 4.63 | 8.99E-03 |
| PWY_6467_Kdo_transfer_to_lipid_IVA_III_Chlamydia_ | 3.78 | 4.52 | 1.28E-02 |
| PWY_7204_pyridoxal_5_phosphate_salvage_II_plants_ | 54.71 | 4.49 | 1.30E-10 |
| PWY_5870_ubiquinol_8_biosynthesis_eukaryotic_ | 2.30 | 4.47 | 1.22E-02 |
| PWY_4202_arsenate_detoxification_I_glutaredoxin_ | 1.35 | 4.45 | 9.34E-03 |
| PWY_7528_L_methionine_salvage_cycle_I_bacteria_and_plants_ | 2.04 | 4.26 | 1.86E-02 |
| P164_PWY_purine_nucleobases_degradation_I_anaerobic_ | 9907.48 | 4.21 | 1.09E-18 |
| LYSINE_DEG1_PWY_L_lysine_degradation_XI_mammalian_ | 1.37 | 4.19 | 1.87E-02 |
| PWY_7270_L_methionine_salvage_cycle_II_plants_ | 1.84 | 4.16 | 2.23E-02 |
| PWY_7527_L_methionine_salvage_cycle_III | 1.84 | 4.16 | 2.23E-02 |
| PWY_5179_toluene_degradation_V_aerobic_via_toluene_cis_diol_ | 1.73 | 4.11 | 2.41E-02 |
| PWY3O_19_ubiquinol_6_biosynthesis_from_4_hydroxybenzoate_eukaryotic_ | 2.55 | 4.09 | 2.71E-02 |
| THREOCAT_PWY_superpathway_of_L_threonine_metabolism | 14.20 | 4.07 | 5.70E-07 |
| PWY_3941_beta_alanine_biosynthesis_II | 3.74 | 3.99 | 1.31E-02 |
| PWY_7118_chitin_degradation_to_ethanol | 24.96 | 3.98 | 3.74E-11 |

FIG. 15D

| Pathway | baseMean | log2FoldChange | padj |
|---|---|---|---|
| LYSINE_AMINOAD_PWY_L_lysine_biosynthesis_IV | 15.62 | 3.90 | 1.60E-08 |
| 4_HYDROXYMANDELATE_DEGRADATION_PWY_4_hydroxymandelate_degradation | 4.35 | 3.89 | 3.42E-03 |
| PWY_6263_superpathway_of_menaquinol_8_biosynthesis_II | 14.70 | 3.87 | 2.75E-09 |
| PWY0_321_phenylacetate_degradation_I_aerobic_ | 2.02 | 3.83 | 4.14E-02 |
| AST_PWY_L_arginine_degradation_II_AST_pathway_ | 1.93 | 3.81 | 4.28E-02 |
| PWY_822_fructan_biosynthesis | 2.19 | 3.61 | 1.60E-02 |
| PWY_5860_superpathway_of_demethylmenaquinol_6_biosynthesis_I | 46.06 | 3.53 | 3.52E-06 |
| PWY_5392_reductive_TCA_cycle_II | 146.95 | 3.49 | 6.31E-11 |
| PWY_5850_superpathway_of_menaquinol_6_biosynthesis_I | 66.66 | 3.47 | 1.68E-06 |
| PWY_4221_pantothenate_and_coenzyme_A_biosynthesis_II_plants_ | 10.68 | 3.36 | 1.07E-03 |
| PWY_5743_3_hydroxypropanoate_cycle | 5.65 | 3.35 | 4.91E-04 |
| PWY_6992_1_5_anhydrofructose_degradation | 374.80 | 3.29 | 3.86E-07 |
| PWY_5367_petroselinate_biosynthesis | 1217.18 | 3.23 | 2.04E-18 |
| PWY_5856_ubiquinol_9_biosynthesis_prokaryotic_ | 8.22 | 3.15 | 2.43E-03 |
| PWY_7218_photosynthetic_3_hydroxybutanoate_biosynthesis_engineered_ | 1.46 | 3.11 | 4.22E-02 |
| PWY_5724_superpathway_of_atrazine_degradation | 1.51 | 3.10 | 4.98E-02 |
| PWY_7090_UDP_2_3_diacetamido_2_3_dideoxy_alpha_D_mannuronate_biosynthesis | 18.52 | 2.86 | 9.84E-06 |
| PWY_6284_superpathway_of_unsaturated_fatty_acids_biosynthesis_E._coli_ | 2977.95 | 2.85 | 7.94E-19 |
| PWY_6383_mono_trans_poly_cis_decaprenyl_phosphate_biosynthesis | 41.80 | 2.61 | 1.94E-14 |
| CRNFORCAT_PWY_creatinine_degradation_I | 865.41 | 2.58 | 1.19E-32 |
| FUCCAT_PWY_fucose_degradation | 691.26 | 2.54 | 2.28E-10 |
| PWY_7377_cob_II_yrinate_a_c_diamide_biosynthesis_I_early_cobalt_insertion_ | 17.61 | 2.52 | 3.35E-06 |
| PWY_6185_4_methylcatechol_degradation_ortho_cleavage_ | 74.40 | 2.43 | 3.59E-09 |
| PWY66_201_nicotine_degradation_IV | 8.29 | 2.34 | 8.49E-04 |
| PWY1F_823_leucopelargonidin_and_leucocyanidin_biosynthesis | 2.72 | 2.20 | 4.17E-02 |
| PWY_7332_superpathway_of_UDP_N_acetylglucosamine_derived_O_antigen_building_blocks_biosynthesis | 9.41 | 2.19 | 1.36E-04 |
| PWY_6749_CMP_legionaminate_biosynthesis_I | 97.74 | 2.19 | 4.55E-08 |
| PWY_6837_fatty_acid_beta_oxidation_V_unsaturated_odd_number_di_isomerase_dependent_ | 24.56 | 2.12 | 1.10E-06 |
| FUC_RHAMCAT_PWY_superpathway_of_fucose_and_rhamnose_degradation | 969.52 | 2.09 | 2.03E-10 |
| PWY_6113_superpathway_of_mycolate_biosynthesis | 7185.05 | 2.08 | 1.03E-17 |
| PWY_7357_thiamin_formation_from_pyrithiamine_and_oxythiamine_yeast_ | 2749.77 | 2.07 | 3.58E-09 |
| PWY_6531_mannitol_cycle | 108.87 | 2.01 | 9.46E-05 |
| PWY_6138_CMP_N_acetylneuraminate_biosynthesis_I_eukaryotes_ | 91.47 | 2.00 | 4.66E-05 |
| PWY_6897_thiamin_salvage_II | 3067.01 | 1.98 | 4.75E-15 |
| PWY_7268_NAD_NADP_NADH_NADPH_cytosolic_interconversion_yeast_ | 42.13 | 1.95 | 9.32E-05 |
| PWY_6470_peptidoglycan_biosynthesis_V_beta_lactam_resistance_ | 159.46 | 1.94 | 2.05E-04 |
| PWY_5101_L_isoleucine_biosynthesis_II | 5278.64 | 1.88 | 1.26E-11 |
| PWY_7345_superpathway_of_anaerobic_sucrose_degradation | 44.24 | 1.77 | 1.15E-03 |
| PWY_3801_sucrose_degradation_II_sucrose_synthase_ | 47.35 | 1.77 | 1.06E-03 |
| PWY_7385_1_3_propanediol_biosynthesis_engineered_ | 345.51 | 1.77 | 4.40E-13 |
| FASYN_INITIAL_PWY_superpathway_of_fatty_acid_biosynthesis_initiation_E._coli_ | 18360.00 | 1.71 | 1.93E-12 |

FIG. 15E

| Pathway | baseMean | log2FoldChange | padj |
|---|---|---|---|
| PROTOCATECHUATE_ORTHO_CLEAVAGE_PWY_protocatechuate_degradation_II_ortho_cleavage_pathway_ | 56.90 | 1.68 | 7.02E-09 |
| P241_PWY_coenzyme_B_biosynthesis | 73.31 | 1.62 | 3.74E-11 |
| KETOGLUCONMET_PWY_ketogluconate_metabolism | 444.30 | 1.62 | 7.20E-10 |
| GLUCUROCAT_PWY_superpathway_of_beta_D_glucuronide_and_D_glucuronate_degradation | 8514.09 | 1.60 | 1.55E-18 |
| ARGDEG_PWY_superpathway_of_L_arginine_putrescine_and_4_aminobutanoate_degradation | 32.25 | 1.60 | 1.91E-02 |
| ORNARGDEG_PWY_superpathway_of_L_arginine_and_L_ornithine_degradation | 32.25 | 1.60 | 1.91E-02 |
| PWY66_399_gluconeogenesis_III | 6850.44 | 1.58 | 3.54E-11 |
| RHAMCAT_PWY_L_rhamnose_degradation_I | 2993.39 | 1.57 | 1.56E-07 |
| PWY_6147_6_hydroxymethyl_dihydropterin_diphosphate_biosynthesis_I | 1635.25 | 1.51 | 1.14E-17 |
| PWY_7242_D_fructuronate_degradation | 10182.99 | 1.49 | 3.10E-19 |
| PWY_7654_8E_10E_dodeca_8_10_dienol_biosynthesis | 15.90 | 1.48 | 2.04E-04 |
| PHOSLIPSYN_PWY_superpathway_of_phospholipid_biosynthesis_I_bacteria_ | 2486.54 | 1.47 | 1.03E-11 |
| PWY_7539_6_hydroxymethyl_dihydropterin_diphosphate_biosynthesis_III_Chlamydia_ | 1516.63 | 1.47 | 6.13E-17 |
| PWY4FS_7_phosphatidylglycerol_biosynthesis_I_plastidic_ | 1691.28 | 1.44 | 1.43E-09 |
| PWY4FS_8_phosphatidylglycerol_biosynthesis_II_non_plastidic_ | 1691.28 | 1.44 | 1.43E-09 |
| POLYAMSYN_PWY_superpathway_of_polyamine_biosynthesis_I | 218.06 | 1.44 | 8.16E-11 |
| PWY_2201_folate_transformations_I | 489.38 | 1.43 | 3.63E-06 |
| ARG_POLYAMINE_SYN_superpathway_of_arginine_and_polyamine_biosynthesis | 422.81 | 1.42 | 1.03E-11 |
| PWY_7388_octanoyl_[acyl_carrier_protein]_biosynthesis_mitochondria_yeast_ | 13263.13 | 1.38 | 6.08E-08 |
| HISTSYN_PWY_L_histidine_biosynthesis | 3964.55 | 1.32 | 2.07E-17 |
| PWY_6700_queuosine_biosynthesis | 3616.11 | 1.31 | 4.59E-09 |
| PWY_6309_L_tryptophan_degradation_XI_mammalian_via_kynurenine_ | 54.39 | 1.29 | 9.21E-04 |
| PWY_5103_L_isoleucine_biosynthesis_III | 10988.46 | 1.28 | 3.57E-12 |
| SALVADEHYPOX_PWY_adenosine_nucleotides_degradation_II | 5138.19 | 1.28 | 9.58E-11 |
| PROPFERM_PWY_L_alanine_fermentation_to_propanoate_and_acetate | 2006.85 | 1.26 | 1.29E-04 |
| GALACTUROCAT_PWY_D_galacturonate_degradation_I | 9698.30 | 1.24 | 5.61E-06 |
| PWY_6168_flavin_biosynthesis_III_fungi_ | 3997.50 | 1.22 | 4.17E-06 |
| ILEUSYN_PWY_L_isoleucine_biosynthesis_I_from_threonine_ | 13093.62 | 1.21 | 7.15E-10 |
| VALSYN_PWY_L_valine_biosynthesis | 13093.62 | 1.21 | 7.15E-10 |
| PWY_7383_anaerobic_energy_metabolism_invertebrates_cytosol_ | 2681.54 | 1.21 | 5.72E-10 |
| PWY_5104_L_isoleucine_biosynthesis_IV | 11287.74 | 1.21 | 3.13E-11 |
| PWY66_398_TCA_cycle_III_animals_ | 1000.25 | 1.19 | 2.25E-07 |
| BRANCHED_CHAIN_AA_SYN_PWY_superpathway_of_branched_amino_acid_biosynthesis | 11576.23 | 1.18 | 1.73E-10 |
| PWY_6123_inosine_5_phosphate_biosynthesis_I | 8650.58 | 1.17 | 6.99E-09 |
| PWY_6124_inosine_5_phosphate_biosynthesis_II | 9676.46 | 1.16 | 7.49E-10 |
| PWY_6285_superpathway_of_fatty_acids_biosynthesis_E._coli_ | 1868.75 | 1.15 | 1.23E-23 |
| PWY_7269_NAD_NADP_NADH_NADPH_mitochondrial_interconversion_yeast_ | 75.41 | 1.15 | 8.20E-04 |

FIG. 15F

| Pathway | baseMean | log2FoldChange | padj |
|---|---|---|---|
| PWY_6285_superpathway_of_fatty_acids_biosynthesis_E._coli_ | 1868.75 | 1.15 | 1.23E-23 |
| PWY_7269_NAD_NADP_NADH_NADPH_mitochondrial_interconversion_yeast_ | 75.41 | 1.15 | 8.20E-04 |
| PWY_6145_superpathway_of_sialic_acids_and_CMP_sialic_acids_biosynthesis | 74.02 | 1.13 | 1.80E-02 |
| PWY_6507_4_deoxy_L_threo_hex_4_enopyranuronate_degradation | 7859.65 | 1.12 | 1.33E-11 |
| PWY_3841_folate_transformations_II | 11791.23 | 1.11 | 5.74E-10 |
| PWY_5100_pyruvate_fermentation_to_acetate_and_lactate_II | 22467.73 | 1.10 | 2.26E-05 |
| THISYN_PWY_superpathway_of_thiamin_diphosphate_biosynthesis_I | 4744.86 | 1.10 | 1.52E-08 |
| PWY_5971_palmitate_biosynthesis_II_bacteria_and_plants_ | 10989.24 | 1.09 | 3.35E-08 |
| GLUTORN_PWY_L_ornithine_biosynthesis | 4804.61 | 1.09 | 6.52E-11 |
| PWY0_862_5Z_dodec_5_enoate_biosynthesis | 9657.46 | 1.06 | 8.87E-06 |
| PWY66_422_D_galactose_degradation_V_Leloir_pathway_ | 10880.58 | 1.06 | 2.56E-03 |
| PWY_7111_pyruvate_fermentation_to_isobutanol_engineered_ | 16173.41 | 1.06 | 5.57E-08 |
| PWY_5189_tetrapyrrole_biosynthesis_II_from_glycine_ | 1530.21 | 1.05 | 3.61E-05 |
| PWY_6353_purine_nucleotides_degradation_II_aerobic_ | 6694.64 | 1.03 | 2.72E-07 |
| RIBOSYN2_PWY_flavin_biosynthesis_I_bacteria_and_plants_ | 3577.60 | 1.03 | 4.68E-05 |
| PWY_6608_guanosine_nucleotides_degradation_III | 7539.12 | 1.02 | 4.79E-05 |
| PYRIDNUCSAL_PWY_NAD_salvage_pathway_I | 916.14 | 1.02 | 5.70E-04 |
| PWY_5156_superpathway_of_fatty_acid_biosynthesis_II_plant_ | 531.21 | 1.01 | 1.67E-03 |

FIG. 16A

| Pathway | baseMean | log2FoldChange | padj |
|---|---|---|---|
| PWY_5088_L_glutamate_degradation_VIII_to_propanoate_ | 1768.79 | 12.59 | 1.5E-59 |
| PWY_6318_L_phenylalanine_degradation_IV_mammalian_via_side_chain_ | 1690.15 | 12.24 | 9.9E-69 |
| GLUDEG_II_PWY_L_glutamate_degradation_VII_to_butanoate_ | 854.51 | 11.77 | 6.0E-51 |
| PWY_6895_superpathway_of_thiamin_diphosphate_biosynthesis_II | 1549.17 | 11.31 | 8.1E-79 |
| PWY_7315_dTDP_N_acetylthomosamine_biosynthesis | 575.21 | 11.27 | 1.8E-45 |
| PWY_6731_starch_degradation_III | 554.47 | 11.20 | 1.7E-44 |
| GLYCOLYSIS_TCA_GLYOX_BYPASS_superpathway_of_glycolysis_pyruvate_dehydrogenase_TCA_and_glyoxylate_bypass | 994.30 | 11.15 | 7.0E-46 |
| PWY_6891_thiazole_biosynthesis_II_Bacillus_ | 602.23 | 11.02 | 1.0E-39 |
| GLYOXYLATE_BYPASS_glyoxylate_cycle | 680.84 | 10.89 | 3.1E-36 |
| TCA_GLYOX_BYPASS_superpathway_of_glyoxylate_bypass_and_TCA | 594.14 | 10.76 | 2.1E-35 |
| PWY_561_superpathway_of_glyoxylate_cycle_and_fatty_acid_degradation | 713.19 | 10.70 | 5.2E-41 |
| P162_PWY_L_glutamate_degradation_V_via_hydroxyglutarate_ | 2197.56 | 9.82 | 6.2E-171 |
| PWY490_3_nitrate_reduction_VI_assimilatory_ | 506.18 | 9.61 | 1.9E-85 |
| PWY_4702_phytate_degradation_I | 124.55 | 9.30 | 4.6E-27 |
| PWY_6165_chorismate_biosynthesis_II_archaea_ | 99.93 | 9.11 | 3.2E-26 |
| P105_PWY_TCA_cycle_IV_2_oxoglutarate_decarboxylase_ | 988.15 | 9.11 | 3.1E-39 |
| PWY_5508_adenosylcobalamin_biosynthesis_from_cobyrinate_a_c_diamide_II | 81.08 | 8.52 | 2.0E-20 |
| TYRFUMCAT_PWY_L_tyrosine_degradation_I | 114.29 | 8.51 | 4.5E-25 |
| PWY0_1277_3_phenylpropanoate_and_3_3_hydroxyphenyl_propanoate_degradation | 100.45 | 8.30 | 1.6E-17 |
| CODH_PWY_reductive_acetyl_coenzyme_A_pathway | 70.65 | 8.20 | 5.2E-18 |
| PWY_7295_L_arabinose_degradation_IV | 52.29 | 8.14 | 6.6E-19 |
| 7ALPHADEHYDROX_PWY_cholate_degradation_bacteria_anaerobic_ | 84.16 | 8.05 | 2.3E-21 |
| PWY_6728_methylaspartate_cycle | 38.67 | 7.80 | 4.1E-17 |
| PWY0_42_2_methylcitrate_cycle_I | 52.84 | 7.72 | 3.4E-15 |
| HCAMHPDEG_PWY_3_phenylpropanoate_and_3_3_hydroxyphenyl_propanoate_degradation_to_2_oxopent_4_enoate | 59.10 | 7.69 | 1.2E-14 |
| PWY_6690_cinnamate_and_3_hydroxycinnamate_degradation_to_2_oxopent_4_enoate | 59.10 | 7.69 | 1.2E-14 |
| NAGLIPASYN_PWY_lipid_IVA_biosynthesis | 120.78 | 7.54 | 1.8E-29 |
| PWY_6803_phosphatidylcholine_acyl_editing | 2309.22 | 7.47 | 6.1E-83 |
| PWY_5747_2_methylcitrate_cycle_II | 47.25 | 7.39 | 2.8E-13 |
| PWY_5417_catechol_degradation_III_ortho_cleavage_pathway_ | 28.29 | 7.37 | 1.2E-14 |
| PWY_5431_aromatic_compounds_degradation_via_beta_ketoadipate | 28.29 | 7.37 | 1.2E-14 |
| PWY_6906_chitin_derivatives_degradation | 249.34 | 7.23 | 5.8E-88 |
| PWY_6182_superpathway_of_salicylate_degradation | 24.68 | 7.14 | 2.2E-13 |
| ALL_CHORISMATE_PWY_superpathway_of_chorismate_metabolism | 28.47 | 7.13 | 6.6E-13 |
| PWY_6641_superpathway_of_sulfolactate_degradation | 53.38 | 7.04 | 3.9E-17 |
| PWY_5055_nicotinate_degradation_III | 18.94 | 7.02 | 1.9E-13 |
| CATECHOL_ORTHO_CLEAVAGE_PWY_catechol_degradation_to_beta_ketoadipate | 20.14 | 6.94 | 1.2E-12 |
| PWY_5178_toluene_degradation_IV_aerobic_via_catechol_ | 19.29 | 6.90 | 1.6E-12 |

FIG. 16B

| Pathway | baseMean | log2FoldChange | padj |
|---|---|---|---|
| P261_PWY_coenzyme_M_biosynthesis_I | 18.08 | 6.89 | 1.1E-12 |
| PWY_5181_toluene_degradation_III_aerobic_via_p_cresol_ | 20.58 | 6.75 | 2.2E-11 |
| PWY_6107_chlorosalicylate_degradation | 25.36 | 6.73 | 7.8E-11 |
| PWY_6863_pyruvate_fermentation_to_hexanol | 19.50 | 6.71 | 2.6E-11 |
| P23_PWY_reductive_TCA_cycle_I | 678.91 | 6.54 | 1.4E-106 |
| PWY_5109_2_methylbutanoate_biosynthesis | 29.98 | 6.54 | 6.7E-17 |
| URSIN_PWY_ureide_biosynthesis | 13.05 | 6.45 | 1.1E-10 |
| PWY_7165_L_ascorbate_biosynthesis_VI_engineered_pathway_ | 17.33 | 6.42 | 6.0E-10 |
| DHGLUCONATE_PYR_CAT_PWY_glucose_degradation_oxidative_ | 12.64 | 6.39 | 1.8E-10 |
| PWY5F9_12_biphenyl_degradation | 32.59 | 6.39 | 5.3E-09 |
| PWY_6708_ubiquinol_8_biosynthesis_prokaryotic_ | 16.51 | 6.33 | 1.4E-09 |
| PWY_7371_1_4_dihydroxy_6_naphthoate_biosynthesis_II | 11.13 | 6.32 | 2.4E-10 |
| UBISYN_PWY_superpathway_of_ubiquinol_8_biosynthesis_prokaryotic_ | 15.84 | 6.31 | 1.4E-09 |
| PWY_6060_malonate_degradation_II_biotin_dependent_ | 10.26 | 6.24 | 4.5E-10 |
| PWY_6215_4_chlorobenzoate_degradation | 12.94 | 6.13 | 4.5E-09 |
| KDO_NAGLIPASYN_PWY_superpathway_of_Kdo_2_lipid_A_biosynthesis | 11.23 | 6.12 | 2.8E-09 |
| PWY3O_1109_superpathway_of_4_hydroxybenzoate_biosynthesis_yeast_ | 30.55 | 6.11 | 3.5E-14 |
| PWY_5183_superpathway_of_aerobic_toluene_degradation | 9.20 | 6.06 | 2.5E-09 |
| PWY_6953_dTDP_3_acetamido_3_6_dideoxy_alpha_D_galactose_biosynthesis | 22.13 | 6.04 | 2.6E-13 |
| PWY_7316_dTDP_N_acetylviosamine_biosynthesis | 591.48 | 6.02 | 3.2E-69 |
| PWY_6565_superpathway_of_polyamine_biosynthesis_III | 95.67 | 5.92 | 8.1E-47 |
| PWY_5005_biotin_biosynthesis_II | 185.39 | 5.91 | 3.5E-16 |
| ECASYN_PWY_enterobacterial_common_antigen_biosynthesis | 11.71 | 5.90 | 3.5E-08 |
| PWY_5532_adenosine_nucleotides_degradation_IV | 8.60 | 5.85 | 2.0E-08 |
| PWY_6415_L_ascorbate_biosynthesis_V | 24.06 | 5.85 | 2.3E-07 |
| P165_PWY_superpathway_of_purines_degradation_in_plants | 6.99 | 5.80 | 1.4E-08 |
| PWY_7374_1_4_dihydroxy_6_naphthoate_biosynthesis_I | 6.98 | 5.75 | 2.5E-08 |
| P281_PWY_3_phenylpropanoate_degradation | 9.11 | 5.74 | 7.8E-08 |
| PWY_5743_3_hydroxypropanoate_cycle | 6.52 | 5.64 | 6.4E-08 |
| AST_PWY_L_arginine_degradation_II_AST_pathway_ | 6.45 | 5.61 | 8.5E-08 |
| PWY_7118_chitin_degradation_to_ethanol | 29.26 | 5.57 | 1.2E-20 |
| 4_HYDROXYMANDELATE_DEGRADATION_PWY_4_hydroxymandelate_degradation | 6.29 | 5.55 | 1.4E-07 |
| PWY_5507_adenosylcobalamin_biosynthesis_I_early_cobalt_insertion_ | 9.12 | 5.52 | 3.0E-10 |
| DENITRIFICATION_PWY_nitrate_reduction_I_denitrification_ | 6.92 | 5.50 | 2.9E-07 |
| PWY_6769_rhamnogalacturonan_type_I_degradation_I_fungi_ | 5.67 | 5.49 | 1.7E-07 |
| PWY_7318_dTDP_3_acetamido_3_6_dideoxy_alpha_D_glucose_biosynthesis | 29.41 | 5.46 | 5.2E-12 |
| PWY_6981_chitin_biosynthesis | 9.15 | 5.42 | 1.1E-06 |
| PWY_6562_norspermidine_biosynthesis | 64.05 | 5.34 | 6.2E-35 |
| PWY_7007_methyl_ketone_biosynthesis | 2139.12 | 5.26 | 3.3E-34 |
| PWY_622_starch_biosynthesis | 41.39 | 5.25 | 1.2E-06 |
| PWY_5430_meta_cleavage_pathway_of_aromatic_compounds | 4.42 | 5.23 | 9.0E-07 |
| PWY_7317_superpathway_of_dTDP_glucose_derived_O_antigen_building_blocks_biosynthesis | 5.45 | 5.16 | 2.6E-06 |

FIG. 16C

| Pathway | baseMean | log2FoldChange | padj |
|---|---|---|---|
| PWY_7373_superpathway_of_demethylmenaquinol_6_biosynthesis_II | 4.09 | 5.16 | 1.4E-06 |
| PWY_6596_adenosine_nucleotides_degradation_I | 56.89 | 5.16 | 1.5E-10 |
| PWY_5265_peptidoglycan_biosynthesis_II_staphylococci_ | 6.15 | 5.05 | 7.5E-06 |
| PWY_2723_trehalose_degradation_V | 16.54 | 5.05 | 2.0E-05 |
| PWY_5044_purine_nucleotides_degradation_I_plants_ | 103.28 | 5.02 | 6.8E-12 |
| REDCITCYC_TCA_cycle_VIII_helicobacter_ | 1014.89 | 4.85 | 4.1E-16 |
| GLYCOCAT_PWY_glycogen_degradation_I_bacterial_ | 47.79 | 4.84 | 3.0E-22 |
| PWY_5179_toluene_degradation_V_aerobic_via_toluene_cis_diol_ | 4.52 | 4.83 | 2.0E-05 |
| PWY_6518_glycocholate_metabolism_bacteria_ | 352.61 | 4.75 | 7.6E-07 |
| PWY_6531_mannitol_cycle | 63.89 | 4.63 | 1.1E-36 |
| PWY_5855_ubiquinol_7_biosynthesis_prokaryotic_ | 16.07 | 4.53 | 1.2E-06 |
| PWY_5857_ubiquinol_10_biosynthesis_prokaryotic_ | 16.07 | 4.53 | 1.2E-06 |
| PWY_6749_CMP_legionaminate_biosynthesis_I | 92.42 | 4.53 | 4.4E-36 |
| PWY_5420_catechol_degradation_II_meta_cleavage_pathway_ | 7.07 | 4.50 | 5.5E-07 |
| LPSSYN_PWY_superpathway_of_lipopolysaccharide_biosynthesis | 7.44 | 4.43 | 2.4E-04 |
| UDPNACETYLGALSYN_PWY_UDP_N_acetyl_D_glucosamine_biosynthesis_II | 123.13 | 4.39 | 1.3E-16 |
| PWY_5514_UDP_N_acetyl_D_galactosamine_biosynthesis_II | 184.59 | 4.36 | 8.6E-17 |
| GLUDEG_I_PWY_GABA_shunt | 426.68 | 4.34 | 1.1E-56 |
| PWY_5419_catechol_degradation_to_2_oxopent_4_enoate_II | 4.13 | 4.32 | 1.3E-05 |
| PWY_5180_toluene_degradation_I_aerobic_via_o_cresol_ | 117.25 | 4.29 | 1.3E-04 |
| PWY_5182_toluene_degradation_II_aerobic_via_4_methylcatechol_ | 117.25 | 4.29 | 1.3E-04 |
| PWY_7384_anaerobic_energy_metabolism_invertebrates_mitochondrial_ | 1837.62 | 4.21 | 8.1E-14 |
| THREOCAT_PWY_superpathway_of_L_threonine_metabolism | 19.57 | 4.05 | 1.6E-07 |
| PWY3O_19_ubiquinol_6_biosynthesis_from_4_hydroxybenzoate_eukaryotic_ | 3.91 | 4.00 | 1.1E-03 |
| PWY_5392_reductive_TCA_cycle_II | 88.48 | 3.90 | 1.5E-49 |
| PWY_6138_CMP_N_acetylneuraminate_biosynthesis_I_eukaryotes_ | 60.48 | 3.82 | 9.1E-32 |
| PWY_4321_L_glutamate_degradation_IV | 76.29 | 3.80 | 2.6E-19 |
| 3_HYDROXYPHENYLACETATE_DEGRADATION_PWY_4_hydroxyphenylacetate_degradation | 32.89 | 3.80 | 1.6E-08 |
| PWY_6823_molybdenum_cofactor_biosynthesis | 60.16 | 3.78 | 1.8E-21 |
| P3_PWY_gallate_degradation_III_anaerobic_ | 118.85 | 3.73 | 2.2E-04 |
| PWY_5856_ubiquinol_9_biosynthesis_prokaryotic_ | 9.25 | 3.70 | 3.3E-05 |
| CRNFORCAT_PWY_creatinine_degradation_I | 769.59 | 3.70 | 9.7E-12 |
| PWY_822_fructan_biosynthesis | 2.46 | 3.54 | 1.1E-03 |
| PWY_7204_pyridoxal_5_phosphate_salvage_II_plants_ | 46.04 | 3.53 | 6.9E-18 |
| PWY_7389_superpathway_of_anaerobic_energy_metabolism_invertebrates_ | 1404.17 | 3.49 | 3.3E-12 |
| PWY_4202_arsenate_detoxification_I_glutaredoxin_ | 2.16 | 3.40 | 1.5E-03 |
| NPGLUCAT_PWY_Entner_Doudoroff_pathway_II_non_phosphorylative_ | 11.89 | 3.33 | 1.0E-04 |
| PWY_7414_dTDP_alpha_D_mycaminose_biosynthesis | 1.46 | 3.32 | 7.8E-03 |
| METH_ACETATE_PWY_methanogenesis_from_acetate | 2240.01 | 3.29 | 2.2E-13 |
| PWY0_1241_ADP_L_glycero_beta_D_manno_heptose_biosynthesis | 48.55 | 3.22 | 3.5E-21 |
| PWY0_1261_anhydromuropeptides_recycling | 272.39 | 3.11 | 2.0E-04 |

FIG. 16D

| Pathway | baseMean | log2FoldChange | padj |
|---|---|---|---|
| PWY_7090_UDP_2_3_diacetamido_2_3_dideoxy_alpha_D_mannuronate_biosynthesis | 10.64 | 2.94 | 1.6E-06 |
| PWY_5870_ubiquinol_8_biosynthesis_eukaryotic_ | 4.95 | 2.91 | 2.4E-02 |
| LYSINE_DEG1_PWY_L_lysine_degradation_XI_mammalian_ | 1.12 | 2.85 | 2.6E-02 |
| PWY66_399_gluconeogenesis_III | 5270.58 | 2.83 | 1.2E-28 |
| PWY_6383_mono_trans_poly_cis_decaprenyl_phosphate_biosynthesis | 48.63 | 2.81 | 2.1E-37 |
| KETOGLUCONMET_PWY_ketogluconate_metabolism | 503.84 | 2.79 | 1.2E-41 |
| PWY_6957_mandelate_degradation_to_acetyl_CoA | 1.05 | 2.78 | 3.0E-02 |
| PWY_6145_superpathway_of_sialic_acids_and_CMP_sialic_acids_biosynthesis | 39.29 | 2.74 | 5.3E-08 |
| PWY_5531_chlorophyllide_a_biosynthesis_II_anaerobic_ | 11.22 | 2.73 | 1.1E-03 |
| PWY_7159_chlorophyllide_a_biosynthesis_III_aerobic_light_independent_ | 11.22 | 2.73 | 1.1E-03 |
| PWY_6263_superpathway_of_menaquinol_8_biosynthesis_II | 23.23 | 2.71 | 2.2E-14 |
| CHLOROPHYLL_SYN_chlorophyllide_a_biosynthesis_I_aerobic_light_dependent_ | 10.21 | 2.60 | 1.7E-03 |
| PWY_6992_1_5_anhydrofructose_degradation | 542.18 | 2.60 | 3.2E-05 |
| PWY_7383_anaerobic_energy_metabolism_invertebrates_cytosol_ | 2043.62 | 2.55 | 2.1E-30 |
| PWY_6886_1_butanol_autotrophic_biosynthesis | 0.77 | 2.55 | 4.9E-02 |
| PWY_5306_superpathway_of_thiosulfate_metabolism_Desulfovibrio_sulfodismutans_ | 1.80 | 2.51 | 4.6E-02 |
| PWY_6876_isopropanol_biosynthesis | 1482.98 | 2.49 | 2.5E-18 |
| PWY_3941_beta_alanine_biosynthesis_II | 2.90 | 2.41 | 2.6E-03 |
| PWY_4221_pantothenate_and_coenzyme_A_biosynthesis_II_plants_ | 8.38 | 2.40 | 2.2E-05 |
| PWY_7357_thiamin_formation_from_pyrithiamine_and_oxythiamine_yeast_ | 2137.76 | 2.27 | 2.9E-11 |
| ARGDEG_PWY_superpathway_of_L_arginine_putrescine_and_4_aminobutanoate_degradation | 27.59 | 2.22 | 2.5E-10 |
| ORNARGDEG_PWY_superpathway_of_L_arginine_and_L_ornithine_degradation | 27.59 | 2.22 | 2.5E-10 |
| GLYCOL_GLYOXDEG_PWY_superpathway_of_glycol_metabolism_and_degradation | 447.62 | 2.19 | 3.8E-04 |
| ARGDEG_IV_PWY_L_arginine_degradation_VIII_arginine_oxidase_pathway_ | 1.22 | 2.18 | 3.8E-02 |
| PWY_7345_superpathway_of_anaerobic_sucrose_degradation | 29.42 | 2.16 | 6.6E-09 |
| PWY_3801_sucrose_degradation_II_sucrose_synthase_ | 31.40 | 2.15 | 6.5E-09 |
| PWY_6897_thiamin_salvage_II | 2510.63 | 2.13 | 6.8E-17 |
| PROPFERM_PWY_L_alanine_fermentation_to_propanoate_and_acetate | 1582.34 | 2.09 | 1.7E-05 |
| SALVADEHYPOX_PWY_adenosine_nucleotides_degradation_II | 4779.67 | 2.06 | 7.3E-28 |
| PWY_1622_formaldehyde_assimilation_I_serine_pathway_ | 161.14 | 1.88 | 1.0E-04 |
| P164_PWY_purine_nucleobases_degradation_I_anaerobic_ | 10311.89 | 1.88 | 1.6E-21 |
| PWY_5022_4_aminobutanoate_degradation_V | 529.56 | 1.84 | 2.5E-03 |
| PWY_6700_queuosine_biosynthesis | 2851.02 | 1.83 | 1.6E-20 |
| PWY_7377_cob_II_yrinate_a_c_diamide_biosynthesis_I_early_cobalt_insertion_ | 25.05 | 1.82 | 1.9E-11 |
| PWY66_201_nicotine_degradation_IV | 7.51 | 1.75 | 6.7E-03 |
| GALACTARDEG_PWY_D_galactarate_degradation_I | 174.18 | 1.73 | 6.6E-19 |
| GLUCARGALACTSUPER_PWY_superpathway_of_D_glucarate_and_D_galactarate_degradation | 174.18 | 1.73 | 6.6E-19 |

FIG. 16E

| Pathway | baseMean | log2FoldChange | padj |
|---|---|---|---|
| PWY_181_photorespiration | 369.11 | 1.52 | 1.3E-02 |
| PWY_7242_D_fructuronate_degradation | 11749.36 | 1.47 | 2.4E-22 |
| PWY_7268_NAD_NADP_NADH_NADPH_cytosolic_interconversion_yeast_ | 26.28 | 1.39 | 6.7E-03 |
| PWY_6608_guanosine_nucleotides_degradation_III | 7143.86 | 1.37 | 5.5E-13 |
| THISYN_PWY_superpathway_of_thiamin_diphosphate_biosynthesis_I | 3868.29 | 1.35 | 2.7E-17 |
| PWY_2201_folate_transformations_I | 430.07 | 1.35 | 7.1E-20 |
| GLUTORN_PWY_L_ornithine_biosynthesis | 3495.23 | 1.28 | 5.2E-36 |
| FUCCAT_PWY_fucose_degradation | 1067.02 | 1.28 | 1.4E-06 |
| PWY_5529_superpathway_of_bacteriochlorophyll_a_biosynthesis | 6.44 | 1.23 | 5.0E-02 |
| PWY_6892_thiazole_biosynthesis_I_E._coli_ | 3637.23 | 1.22 | 7.9E-07 |
| PWY_5367_petroselinate_biosynthesis | 1171.62 | 1.12 | 1.6E-04 |
| FASYN_INITIAL_PWY_superpathway_of_fatty_acid_biosynthesis_initiation_E._coli_ | 14420.51 | 1.12 | 2.8E-13 |
| PWY_3841_folate_transformations_II | 10412.30 | 1.11 | 2.2E-16 |
| PWY_6124_inosine_5_phosphate_biosynthesis_II | 9637.12 | 1.08 | 2.1E-44 |
| TRPSYN_PWY_L_tryptophan_biosynthesis | 67.83 | 1.07 | 1.9E-02 |
| PWY_6629_superpathway_of_L_tryptophan_biosynthesis | 144.69 | 1.06 | 1.7E-02 |
| PWY_7269_NAD_NADP_NADH_NADPH_mitochondrial_interconversion_yeast_ | 43.70 | 1.05 | 9.4E-04 |
| FUC_RHAMCAT_PWY_superpathway_of_fucose_and_rhamnose_degradation | 1547.70 | 1.04 | 2.1E-05 |
| PWY_6123_inosine_5_phosphate_biosynthesis_I | 8169.52 | 1.03 | 5.9E-87 |
| PWY_6284_superpathway_of_unsaturated_fatty_acids_biosynthesis_E._coli_ | 2956.01 | 1.02 | 8.2E-06 |

FIG. 17A

| Pathway | baseMean | log2FoldChange | padj |
|---|---|---|---|
| PWY_922_mevalonate_pathway_I | 61.65 | 4.36 | 4.23E-10 |
| PWY_5910_superpathway_of_geranylgeranyldiphosphate_biosynthesis_I_via_mevalonate_ | 85.58 | 4.24 | 3.46E-09 |
| PWY_7391_isoprene_biosynthesis_II_engineered_ | 40.16 | 4.00 | 5.39E-05 |
| PWY_7433_mucin_core_1_and_core_2_O_glycosylation | 5.96 | 3.97 | 4.77E-05 |
| PWY_6857_retinol_biosynthesis | 27.23 | 3.72 | 8.76E-15 |
| PWY_7420_monoacylglycerol_metabolism_yeast_ | 5.59 | 3.70 | 1.39E-05 |
| PWY_6351_D_myo_inositol_1_4_5_trisphosphate_biosynthesis | 2.42 | 3.48 | 9.29E-04 |
| PWY_5677_succinate_fermentation_to_butanoate | 79.27 | 3.36 | 1.25E-04 |
| PWY_5173_superpathway_of_acetyl_CoA_biosynthesis | 2312.82 | 3.28 | 3.21E-23 |
| PWY_6367_D_myo_inositol_5_phosphate_metabolism | 0.93 | 3.21 | 9.09E-03 |
| LACTOSECAT_PWY_lactose_and_galactose_degradation_I | 6926.21 | 3.19 | 6.41E-72 |
| PWY_6342_noradrenaline_and_adrenaline_degradation | 2.31 | 3.16 | 1.27E-02 |
| PWY_5754_4_hydroxybenzoate_biosynthesis_I_eukaryotes_ | 1211.73 | 3.03 | 3.20E-10 |
| PWY_5384_sucrose_degradation_IV_sucrose_phosphorylase_ | 788.10 | 3.00 | 4.39E-22 |
| PWY_4041_gamma_glutamyl_cycle | 512.49 | 2.96 | 6.02E-15 |
| PWY_5791_1_4_dihydroxy_2_naphthoate_biosynthesis_II_plants_ | 395.20 | 2.95 | 2.60E-05 |
| PWY_5837_1_4_dihydroxy_2_naphthoate_biosynthesis_I | 395.20 | 2.95 | 2.60E-05 |
| PWY_7117_C4_photosynthetic_carbon_assimilation_cycle_PEPCK_type | 3204.80 | 2.92 | 8.68E-20 |
| PWY_6362_1D_myo_inositol_hexakisphosphate_biosynthesis_II_mammalian_ | 1.63 | 2.86 | 1.13E-02 |
| PWY_5863_superpathway_of_phylloquinol_biosynthesis | 419.41 | 2.85 | 3.86E-05 |
| PWY_241_C4_photosynthetic_carbon_assimilation_cycle_NADP_ME_type | 2552.59 | 2.85 | 1.24E-20 |
| PWY_7277_sphingolipid_biosynthesis_mammals_ | 0.80 | 2.80 | 2.77E-02 |
| PWY_621_sucrose_degradation_III_sucrose_invertase_ | 2688.21 | 2.78 | 3.79E-17 |
| PWY_6352_3_phosphoinositide_biosynthesis | 1.58 | 2.73 | 1.93E-02 |
| PWY_5381_pyridine_nucleotide_cycling_plants_ | 35.75 | 2.64 | 6.88E-05 |
| PWY_6554_1D_myo_inositol_hexakisphosphate_biosynthesis_V_from_Ins_1_3_4_P3_ | 6.52 | 2.62 | 5.67E-05 |
| PWY_6185_4_methylcatechol_degradation_ortho_cleavage_ | 433.71 | 2.60 | 3.11E-15 |
| PWY_7511_protein_ubiquitylation | 1.17 | 2.55 | 2.45E-02 |
| PWY_7434_terminal_O_glycans_residues_modification | 9.17 | 2.47 | 3.92E-04 |
| PWY_6555_superpathway_of_1D_myo_inositol_hexakisphosphate_biosynthesis_plants_ | 8.14 | 2.44 | 3.92E-05 |
| PWY_7039_phosphatidate_metabolism_as_a_signaling_molecule | 2.29 | 2.42 | 8.91E-03 |
| PWY_7616_methanol_oxidation_to_carbon_dioxide | 63.26 | 2.39 | 3.46E-09 |
| PWY_6549_L_glutamine_biosynthesis_III | 3649.20 | 2.37 | 8.42E-37 |
| PWY_7220_adenosine_deoxyribonucleotides_de_novo_biosynthesis_II | 10317.58 | 2.36 | 2.35E-32 |
| PWY_7222_guanosine_deoxyribonucleotides_de_novo_biosynthesis_II | 10317.58 | 2.36 | 2.35E-32 |
| PWY_1861_formaldehyde_assimilation_II_RuMP_Cycle_ | 839.82 | 2.35 | 8.21E-06 |
| PWY_6478_GDP_D_glycero_alpha_D_manno_heptose_biosynthesis | 20.99 | 2.19 | 1.95E-08 |
| PWY_6883_pyruvate_fermentation_to_butanol_II | 1279.01 | 2.18 | 3.23E-30 |
| P124_PWY_Bifidobacterium_shunt | 9880.71 | 2.18 | 6.45E-12 |
| P122_PWY_heterolactic_fermentation | 8359.17 | 2.16 | 4.87E-12 |
| RUMP_PWY_formaldehyde_oxidation_I | 504.38 | 2.11 | 1.73E-05 |
| PWY_6572_chondroitin_sulfate_degradation_I_bacterial_ | 24.21 | 2.08 | 2.07E-05 |
| PWY_6470_peptidoglycan_biosynthesis_V_beta_lactam_resistance_ | 478.42 | 2.08 | 1.05E-20 |
| PWY3O_355_stearate_biosynthesis_III_fungi_ | 927.64 | 2.08 | 1.17E-12 |
| PWY0_41_allantoin_degradation_IV_anaerobic_ | 40.66 | 1.93 | 1.62E-04 |
| PWY_5861_superpathway_of_demethylmenaquinol_8_biosynthesis | 403.04 | 1.93 | 2.53E-03 |
| PWY_5897_superpathway_of_menaquinol_11_biosynthesis | 547.22 | 1.93 | 2.28E-03 |
| PWY_5898_superpathway_of_menaquinol_12_biosynthesis | 547.22 | 1.93 | 2.28E-03 |
| PWY_5899_superpathway_of_menaquinol_13_biosynthesis | 547.22 | 1.93 | 2.28E-03 |

FIG. 17B

| Pathway | baseMean | log2FoldChange | padj |
|---|---|---|---|
| HEXITOLDEGSUPER_PWY_superpathway_of_hexitol_degradation_bacteria_ | 248.55 | 1.92 | 6.44E-03 |
| PWY_7234_inosine_5_phosphate_biosynthesis_III | 1194.50 | 1.91 | 6.12E-11 |
| PWY_7328_superpathway_of_UDP_glucose_derived_O_antigen_building_blocks_biosynthesis | 1020.84 | 1.86 | 1.89E-14 |
| PWY_5840_superpathway_of_menaquinol_7_biosynthesis | 577.44 | 1.84 | 3.14E-03 |
| PWY_5692_allantoin_degradation_to_glyoxylate_II | 37.20 | 1.82 | 2.99E-05 |
| URDEGR_PWY_superpathway_of_allantoin_degradation_in_plants | 37.20 | 1.82 | 2.99E-05 |
| PWY_5705_allantoin_degradation_to_glyoxylate_III | 58.30 | 1.82 | 1.73E-05 |
| PWY_5838_superpathway_of_menaquinol_8_biosynthesis_I | 531.80 | 1.81 | 3.51E-03 |
| PWY_7456_mannan_degradation | 3776.46 | 1.76 | 2.15E-05 |
| PWY_5994_palmitate_biosynthesis_I_animals_and_fungi_ | 1060.29 | 1.75 | 1.26E-10 |
| PWY_2221_Entner_Doudoroff_pathway_III_semi_phosphorylative_ | 283.16 | 1.70 | 3.44E-04 |
| P562_PWY_myo_inositol_degradation_I | 518.22 | 1.69 | 9.87E-11 |
| PWY_6612_superpathway_of_tetrahydrofolate_biosynthesis | 730.83 | 1.69 | 4.81E-10 |
| PWY_7409_phospholipid_remodeling_phosphatidylethanolamine_yeast_ | 11.16 | 1.64 | 8.19E-03 |
| FOLSYN_PWY_superpathway_of_tetrahydrofolate_biosynthesis_and_salvage | 1035.16 | 1.62 | 6.95E-10 |
| PWY_5083_NAD_NADH_phosphorylation_and_dephosphorylation | 1335.17 | 1.56 | 5.30E-03 |
| PWY_6471_peptidoglycan_biosynthesis_IV_Enterococcus_faecium_ | 1489.89 | 1.55 | 1.37E-09 |
| PWY4LZ_257_superpathway_of_fermentation_Chlamydomonas_reinhardtii | 16582.56 | 1.55 | 1.11E-69 |
| PWY_6595_superpathway_of_guanosine_nucleotides_degradation_plants_ | 3127.18 | 1.54 | 8.14E-08 |
| PWY_7237_myo_chiro_and_scillo_inositol_degradation | 10898.90 | 1.42 | 3.62E-13 |
| PWY_6396_superpathway_of_2_3_butanediol_biosynthesis | 711.01 | 1.42 | 3.65E-06 |
| PWY_6125_superpathway_of_guanosine_nucleotides_de_novo_biosynthesis_II | 8847.81 | 1.39 | 6.21E-51 |
| PWY_6901_superpathway_of_glucose_and_xylose_degradation | 17459.14 | 1.38 | 8.79E-40 |
| PWY0_845_superpathway_of_pyridoxal_5_phosphate_biosynthesis_and_salvage | 2848.83 | 1.37 | 1.53E-12 |
| METHGLYUT_PWY_superpathway_of_methylglyoxal_degradation | 797.82 | 1.33 | 3.36E-08 |
| PWY_7224_purine_deoxyribonucleosides_salvage | 16.48 | 1.32 | 2.72E-03 |
| PWY_6630_superpathway_of_L_tyrosine_biosynthesis | 3199.17 | 1.31 | 2.38E-12 |
| PWY_5941_glycogen_degradation_II_eukaryotic_ | 3845.08 | 1.28 | 5.79E-04 |
| P125_PWY_superpathway_of_R_R_butanediol_biosynthesis | 373.52 | 1.28 | 9.37E-05 |
| PWY_6126_superpathway_of_adenosine_nucleotides_de_novo_biosynthesis_II | 10307.84 | 1.27 | 5.07E-28 |
| ASPASN_PWY_superpathway_of_L_aspartate_and_L_asparagine_biosynthesis | 10274.14 | 1.25 | 8.56E-15 |
| PWY_6269_adenosylcobalamin_salvage_from_cobinamide_II | 847.25 | 1.25 | 4.76E-12 |
| PWY_5464_superpathway_of_cytosolic_glycolysis_plants_pyruvate_dehydrogenase_and_TCA_cycle | 2234.58 | 1.16 | 3.65E-06 |
| PWY_7046_4_coumarate_degradation_anaerobic_ | 438.32 | 1.12 | 1.77E-02 |
| PWY0_1479_tRNA_processing | 4056.12 | 1.11 | 6.81E-12 |
| PWY66_367_ketogenesis | 18.06 | 1.11 | 1.20E-02 |
| PWY_3481_superpathway_of_L_phenylalanine_and_L_tyrosine_biosynthesis | 59.79 | 1.11 | 1.41E-04 |
| PWY0_166_superpathway_of_pyrimidine_deoxyribonucleotides_de_novo_biosynthesis_E_coli_ | 2853.48 | 1.10 | 2.09E-17 |
| PWY_7197_pyrimidine_deoxyribonucleotide_phosphorylation | 2054.02 | 1.10 | 3.95E-08 |
| PRPP_PWY_superpathway_of_histidine_purine_and_pyrimidine_biosynthesis | 3044.52 | 1.09 | 5.26E-07 |
| GLUCONEO_PWY_gluconeogenesis_I | 38276.59 | 1.08 | 6.01E-38 |
| HEMESYN2_PWY_heme_biosynthesis_II_anaerobic_ | 194.92 | 1.08 | 3.46E-03 |
| PWY_821_superpathway_of_sulfur_amino_acid_biosynthesis_Saccharomyces_cerevisiae_ | 636.26 | 1.08 | 9.45E-11 |
| PWY_7228_superpathway_of_guanosine_nucleotides_de_novo_biosynthesis_I | 9516.92 | 1.08 | 1.82E-12 |
| PWY_7337_10_cis_heptadecenoyl_CoA_degradation_yeast_ | 28.75 | 1.05 | 1.91E-03 |
| PWY_7338_10_trans_heptadecenoyl_CoA_degradation_reductase_dependent_yeast_ | 28.75 | 1.05 | 1.91E-03 |
| PENTOSE_P_PWY_pentose_phosphate_pathway | 15216.66 | 1.03 | 3.50E-13 |
| PWY_7184_pyrimidine_deoxyribonucleotides_de_novo_biosynthesis_I | 3815.99 | 1.03 | 1.75E-22 |
| PWY_6519_8_amino_7_oxononanoate_biosynthesis_I | 1207.04 | 1.02 | 1.02E-02 |
| PWY_7198_pyrimidine_deoxyribonucleotides_de_novo_biosynthesis_IV | 2367.86 | 1.01 | 2.86E-09 |

FIG. 18A

| Candidate Name | candidate_kegg | Log2Fold Change | pvalue |
|---|---|---|---|
| 1,2-Dioleoyl PC | | 7.73 | 6.76E-03 |
| 1,2-Dioleoyl phosphatidyl ethanolamine | | 7.72 | 6.11E-03 |
| Sphinganine-phosphate | C01120 | 6.75 | 5.41E-03 |
| Vitamin D2 3-glucuronide | C03033 | 6.68 | 1.57E-03 |
| L-Oleandrosyl-oleandolide | C11992 | 6.56 | 4.25E-05 |
| Butirosin B | C17586 | 6.50 | 1.46E-03 |
| Ouabain | C01443 | 6.15 | 6.07E-04 |
| S-(2-Methylpropionyl)-dihydrolipoamide-E | C15977 | 5.85 | 5.44E-03 |
| Astaxanthin | C08580 | 5.83 | 8.19E-06 |
| 6,8a-Seco-6,8a-deoxy-5-oxoavermectin "1b" aglycone | C11961 | 5.69 | 2.77E-03 |
| Estrone | C00468 | 5.62 | 2.06E-02 |
| N-Desmethyltamoxifen | C16546 | 5.57 | 4.96E-03 |
| Mesobilirubinogen | C05790 | 5.45 | 3.25E-05 |
| 2-Octaprenyl-3-methyl-6-methoxy-1,4-benzoquinone | C05814 | 5.35 | 3.93E-03 |
| 6,8a-Seco-6,8a-deoxy-5-oxoavermectin "1a" aglycone | C11977 | 5.31 | 1.24E-04 |
| 3α,12α-Dihydroxy-5β-chol-6-en-24-oic Acid | C11637 | 5.21 | 6.57E-03 |
| Ergocornine | C09162 | 4.89 | 4.11E-04 |
| Tetrahydrocorticosterone | C05476 | 4.81 | 4.57E-04 |
| Butyryl-CoA | C00136 | 4.80 | 7.77E-03 |
| 25-hydroxyvitamin D3 / 25-hydroxycholecalciferol / calcidiol | C01561 | 4.75 | 6.16E-03 |
| Cucurbitacin A | C08793 | 4.74 | 5.66E-03 |
| 13(Z)-Docosenoic Acid | C08316 | 4.61 | 9.21E-03 |
| Adrenic Acid | C16527 | 4.60 | 7.89E-03 |
| LPA(0:0/18:0) | C00416 | 4.39 | 3.80E-03 |
| D-Urobilinogen | C05791 | 4.34 | 1.79E-04 |
| 5,10-Methylenetetrahydromethanopterin | C04377 | 4.01 | 1.21E-02 |
| NeuAcalpha2-3Galbeta1-4GlcNAcbeta1-3(Galalpha1-3Galbeta1-4GlcNAcbeta1-6)Galbeta1-4GlcNAcbeta1-3Galbeta1-4Glcbeta-Cer(d18:1/24:0) | | 3.83 | 2.38E-02 |

FIG. 18B

| Candidate Name | candidate_kegg | Log2Fold Change | pvalue |
|---|---|---|---|
| Asclepin | C08849 | 3.82 | 1.73E-04 |
| Benzoyl glucuronide (Benzoic acid) | C03033 | 3.47 | 5.27E-06 |
| Chlortetracycline | C06571 | 3.41 | 1.52E-04 |
| 7Z, 10Z, 13Z, 16Z, 19Z-docosapentaenoic acid | C16513 | 3.37 | 1.28E-02 |
| L-Urobilinogen | C05789 | 3.29 | 4.00E-03 |
| cis-9,10-Epoxystearic acid | C19418 | 3.12 | 7.45E-04 |
| 4,4'-Diaponeurosporene | C16145 | 3.10 | 9.06E-04 |
| 15(S)-HpEDE | | 3.02 | 6.24E-03 |
| (9S,10S)-10-hydroxy-9-(phosphonooxy)octadecanoic acid | C15989 | 3.00 | 6.18E-03 |
| PS(18:0/20:0) | C02737 | 2.99 | 2.01E-02 |
| Tamoxifen | C07108 | 2.96 | 1.16E-02 |
| Trehalose-6,6'-dibehenate | C19190 | 2.72 | 4.15E-04 |
| 2-Methyl-6-solanyl-1,4-benzoquinol | C17570 | 2.59 | 6.08E-04 |
| 3-alpha-hydroxy-5-alpha-androstane-17-one 3-D-glucuronide | C03033 | 2.51 | 2.27E-03 |
| Oligomycin D | C11314 | 2.47 | 1.54E-02 |
| Taurochenodeoxycholic acid | C05465 | 2.41 | 2.09E-03 |
| Pheophorbide a | C18021 | 2.40 | 1.77E-02 |
| | | 2.28 | 3.37E-03 |
| gamma-L-Glutamyl-butirosin B | C18005 | 2.22 | 5.84E-04 |
| Sphingosine-1-phosphate | C06124 | 2.21 | 7.18E-03 |
| Trp-P-1 | C19306 | 2.16 | 2.03E-04 |
| Picrasin C | C08776 | 2.16 | 1.98E-03 |
| 3-Demethylubiquinone-9 | C03226 | 2.12 | 5.63E-03 |
| Cassaine | C08670 | 2.08 | 8.61E-03 |
| (-)-Jasmonic acid | C08491 | 2.05 | 4.93E-04 |
| Pregnanediol-3-glucuronide | C03033 | 2.04 | 2.54E-04 |
| Epoxymurin-A | C08484 | 2.03 | 1.57E-03 |
| L-Lysine | C00047 | 2.03 | 8.33E-04 |

FIG. 19A

| Candidate Name | candidate_kegg | Log2Fold Change | pvalue |
|---|---|---|---|
| γ-Glutamyl-γ-aminobutyraldehyde | C15700 | 9.75 | 2.17E-03 |
| Perfluidone | C19054 | 9.13 | 2.32E-02 |
| Oxoadipic acid | C00322 | 8.70 | 2.95E-04 |
| (R)-2-Hydroxybutane-1,2,4-tricarboxylate | C01251 | 8.50 | 1.91E-04 |
| 2-Naphtylmethylsuccinic acid | C14115 | 8.44 | 7.25E-04 |
| 5-Methyl-5,6,7,8-tetrahydromethanopterin | C04488 | 8.10 | 1.24E-03 |
| Salidroside | C06046 | 8.07 | 3.87E-03 |
| (R)-S-Lactoylglutathione | C03451 | 7.80 | 2.36E-03 |
| PGD2-d4 | C00696 | 7.71 | 1.77E-03 |
| S-Acetyldihydrolipoamide-E | C16255 | 7.67 | 4.53E-03 |
| 2,6-Dihydroxypseudooxynicotine | C15986 | 7.40 | 1.65E-02 |
| Coumermic acid | C12479 | 7.36 | 9.21E-04 |
| 2-Hexaprenyl-3-methyl-6-methoxy-1,4 benzoquinone | C05804 | 7.02 | 2.90E-03 |
| Rhizocticin A | C17944 | 6.60 | 2.92E-03 |
| Indole-3-acetaldehyde oxime | C02937 | 6.56 | 9.65E-03 |
| 2-deoxyecdysone | C16495 | 6.52 | 2.64E-03 |
| 2-(5'-Methylthio)pentylmalic acid | C17222 | 6.51 | 1.54E-03 |
| D-Saccharic acid | C00818 | 6.51 | 2.45E-03 |
| Avermectin A2b | C11960 | 6.40 | 2.01E-03 |
| TXB2 | C05963 | 6.31 | 3.28E-03 |
| Pyridoxamine | C00534 | 6.28 | 1.85E-02 |
| Stypandrol | C09971 | 6.25 | 2.67E-03 |
| Avermectin B1b monosaccharide | C11965 | 6.23 | 1.57E-02 |
| Porphobilinogen | C00931 | 6.11 | 1.29E-04 |
| Pseudaminic acid | C20082 | 6.06 | 2.63E-03 |
| pregnenolone sulfate | C18044 | 5.97 | 1.44E-03 |
| Chenodeoxycholic acid glycine conjugate | C05466 | 5.94 | 3.30E-03 |
| Nicotinamide riboside | C03150 | 5.94 | 4.46E-04 |
| Zeaxanthin diglucoside | C15969 | 5.92 | 2.43E-03 |
| TG(12:0/12:0/12:0) | C00422 | 5.87 | 4.20E-03 |
| Polhovolide | C09532 | 5.87 | 1.81E-03 |
| Avermectin A2a monosaccharide | C11974 | 5.85 | 1.03E-02 |
| 1-Methoxypyrene-6,7-oxide | C18262 | 5.84 | 4.12E-03 |
| Melibiitol | C05399 | 5.82 | 2.90E-03 |
| N-Carbamoyl-L-aspartic acid | C00438 | 5.76 | 3.15E-04 |
| 2'-N-Acetylparomamine | C17582 | 5.73 | 1.51E-02 |
| PS(13:0/22:6(4Z,7Z,10Z,13Z,16Z,19Z)) | | 5.63 | 1.07E-02 |
| Azadirachtin A | C08748 | 5.57 | 1.57E-03 |
| PS(22:6(4Z,7Z,10Z,13Z,16Z,19Z)/20:5(5Z,8Z,11Z,14Z,17Z)) | | 5.56 | 6.42E-02 |
| Demethylalangiside | C11813 | 5.51 | 1.15E-02 |
| Urocortisol | C05472 | 5.49 | 1.42E-03 |

FIG. 19B

| Candidate Name | candidate_kegg | Log2Fold Change | pvalue |
|---|---|---|---|
| Urocortisol | C05472 | 5.49 | 1.42E-03 |
| Daunorubicin | C01907 | 5.49 | 1.08E-03 |
| Desacetoxyvindoline | C02673 | 5.44 | 8.93E-03 |
| Rabelomycin | C12402 | 5.44 | 8.83E-04 |
| 3',4'-Anhydrovinblastine | C11641 | 5.41 | 2.12E-03 |
| Avermectin A2a | C11976 | 5.34 | 1.00E-03 |
| Traumatic Acid | C16308 | 5.34 | 8.40E-03 |
| Dihydroechinofuran | C18134 | 5.31 | 1.37E-03 |
| Se-Adenosylselenomethionine | C05691 | 5.31 | 2.68E-03 |
| Myriocin | C19914 | 5.31 | 3.92E-04 |
| β-Cryptoxanthin | C08591 | 5.27 | 2.90E-01 |
| L-Histidinol phosphate | C01100 | 5.24 | 1.15E-03 |
| N-Formyldemecolcine | C16710 | 5.22 | 5.59E-03 |
| Thiamine acetic acid | C02892 | 5.18 | 9.41E-04 |
| 7a,12a-Dihydroxy-3-oxo-4-cholenoic acid | C15568 | 5.15 | 1.29E-03 |
| Sarcostin | C17770 | 5.13 | 1.29E-04 |
| PS(P-16:0/22:6(4Z,7Z,10Z,13Z,16Z,19Z)) | | 5.12 | 2.68E-03 |
| N10-Formyltetrahydrofolic acid | C00234 | 5.10 | 2.37E-03 |
| Cortol | C05482 | 5.02 | 4.57E-03 |
| Linatine | C05939 | 4.99 | 4.02E-03 |
| Batrachotoxin | C13750 | 4.99 | 2.60E-03 |
| 2-Octaprenyl-3-methyl-5-hydroxy-6-methoxy-1,4-benzoquinone | C05815 | 4.93 | 2.95E-03 |
| | | 4.89 | 1.20E-03 |
| Indoleglycerol phosphate | C03506 | 4.86 | 2.77E-03 |
| 1,25-hydroxyvitamin D3 | C01673 | 4.82 | 2.41E-04 |
| Echitovenine | C11784 | 4.82 | 2.89E-03 |
| 5-Formyltetrahydrofolate | C03479 | 4.80 | 3.49E-03 |
| α-Cryptoxanthin | C15981 | 4.78 | 6.90E-05 |
| Ribostamycin | C01759 | 4.72 | 2.47E-03 |
| LPA(P-16:0e/0:0) | C15646 | 4.65 | 2.28E-03 |
| Estrone 3-glucuronide | C11133 | 4.65 | 9.43E-03 |
| Staurosporine | C02079 | 4.58 | 1.02E-03 |
| Delphinidin 3-O-glucoside | C12138 | 4.58 | 4.61E-04 |
| 2-Oxoarginine | C03771 | 4.57 | 2.13E-03 |
| Estriol-17-glucuronide | C03033 | 4.47 | 6.04E-03 |
| Anhydrotetracycline | C02811 | 4.47 | 5.62E-03 |
| N-Acetyldemethylphosphinothricin tripeptide | C17950 | 4.47 | 1.18E-02 |
| Erythromycin A | C01912 | 4.46 | 1.62E-03 |
| Avermectin B2b | C11959 | 4.46 | 2.62E-03 |
| Digoxin | C06956 | 4.42 | 1.91E-03 |
| Neamine (Neomycin A) | C01441 | 4.41 | 3.96E-03 |
| 5β-Cyprinolsulfate | C05468 | 4.41 | 1.46E-03 |
| Avermectin B2a | C11975 | 4.38 | 1.15E-03 |

FIG. 19C

| Candidate Name | candidate_kegg | Log2Fold Change | pvalue |
|---|---|---|---|
| Premithramycin B | C12388 | 4.36 | 7.73E-03 |
| Cavinine | C08524 | 4.33 | 7.40E-03 |
| trans-Cinnamic acid | C00423 | 4.29 | 4.04E-04 |
| L-Urobilin | C05793 | 4.28 | 3.02E-03 |
| Coproporphyrin | C03263 | 4.27 | 3.97E-03 |
| Dehydroisoandrosterone 3-glucuronide | C03033 | 4.25 | 6.42E-04 |
| 12-oxo-9(Z)-dodecenoic acid | C16311 | 4.25 | 1.31E-03 |
| Naphthalene-1,2-diol | C03012 | 4.24 | 1.92E-03 |
| Vanillyl alcohol | C06317 | 4.17 | 8.40E-05 |
| UDPMurAc(oyl-L-Ala-D-γ-Glu-L-Lys-D-Ala-D-Ala) | C04702 | 4.17 | 5.64E-03 |
| Megalomicin B | C11986 | 4.17 | 2.62E-04 |
| Chikusetsusaponin IV | C17540 | 4.15 | 9.99E-04 |
| 1D-1-Guanidino-3-amino-1,3-dideoxy-scyllo-inositol | C01298 | 4.15 | 5.53E-04 |
| Macrocin | C00744 | 4.14 | 8.98E-04 |
| L-Glutamyl 5-phosphate | C03287 | 4.12 | 8.26E-03 |
| Tetrahydroaldosterone-3-glucuronide | C03033 | 4.02 | 1.52E-03 |
| Dihydromacarpine | C05316 | 4.02 | 4.47E-04 |
| Gibberellin A44 diacid | C06095 | 3.95 | 2.23E-02 |
| Ritonavir | C07240 | 3.95 | 2.45E-05 |
| Glutathionylspermine | C16562 | 3.88 | 1.20E-02 |
| Isobenzan | C18960 | 3.86 | 2.08E-03 |
| Phenethylamine glucuronide | C03033 | 3.85 | 2.02E-03 |
| (S)-N-Methylcoclaurine | C05176 | 3.85 | 2.12E-02 |
| Pyruvophenone | C17268 | 3.82 | 2.15E-03 |
| 9S,11R,15S-trihydroxy-2,3-dinor-13E-prostaenoic acid-cyclo[8S,12R] | C14795 | 3.80 | 6.45E-04 |
| L-Cystathionine | C02291 | 3.79 | 3.13E-03 |
| Galactosylglycerol | C05401 | 3.79 | 1.27E-02 |
| 20-hydroxy-LTE4 | C03577 | 3.79 | 9.91E-04 |
| Cucurbitacin S | C08806 | 3.76 | 2.19E-03 |
| Staphyloxanthin | C16148 | 3.75 | 7.53E-03 |
| Dihydrodeoxystreptomycin | C03755 | 3.75 | 3.42E-03 |
| 6-deoxyerythronolide B | C03240 | 3.69 | 8.39E-05 |
| 2,4-Bis(acetamido)-2,4,6-trideoxy-beta-L-altropyranose | C19972 | 3.67 | 1.85E-02 |
| Lithocholic acid | C03990 | 3.59 | 6.02E-03 |
| MILTEFOSINE |  | 3.53 | 2.56E-04 |
| Oleandolide | C11990 | 3.53 | 3.03E-03 |
| CAPSAICIN | C06866 | 3.52 | 1.40E-03 |
| Sucrose | C00089 | 3.52 | 2.53E-03 |
| 7-Methylxanthosine | C16352 | 3.49 | 6.10E-03 |
| LIMONIN | C03514 | 3.48 | 4.16E-03 |
| Abscisate | C06082 | 3.47 | 4.49E-03 |
| 9alpha-Hydroxyandrosta-1,4-diene-3,17-dione | C14909 | 3.46 | 3.14E-03 |
| Allocryptopine | C02134 | 3.45 | 5.74E-04 |

FIG. 19D

| Candidate Name | candidate_kegg | Log2Fold Change | pvalue |
|---|---|---|---|
| Adenosyl cobinamide | C06508 | 3.45 | 6.39E-04 |
| Shikimic acid | C00493 | 3.41 | 1.67E-02 |
| Biliverdin IX | C00500 | 3.37 | 2.36E-03 |
| Arachidonoyl Ethanolamide | C11695 | 3.37 | 1.27E-02 |
| Precorrin 8X | C06408 | 3.36 | 4.62E-04 |
| Thebaine | C06173 | 3.34 | 3.90E-04 |
| 3-Hydroxyethylbacteriochlorophyllide a | C18153 | 3.34 | 1.76E-03 |
| Tetrahydrofolic acid | C00101 | 3.33 | 1.42E-02 |
| 3,7,12-Trioxo-5β-cholan-24-oic Acid | C13154 | 3.32 | 1.13E-02 |
| Prebetanin | C08567 | 3.31 | 4.39E-04 |
| Avermectin A1b | C11968 | 3.31 | 3.84E-03 |
| Leukotriene A4 | C00909 | 3.30 | 2.95E-03 |
|  |  | 3.29 | 2.63E-03 |
| Leukotriene E4 | C05952 | 3.29 | 4.63E-03 |
| Homotrypanothione | C16567 | 3.26 | 3.39E-05 |
| Buspirone | C06861 | 3.25 | 9.01E-04 |
| 7α-Hydroxycholest-4-en-3-one | C05455 | 3.23 | 2.06E-04 |
| FMLP | C11596 | 3.19 | 3.29E-03 |
| 17-beta-estradiol-3-glucuronide | C03033 | 3.12 | 8.42E-03 |
| meso-2,6-Diaminoheptanedioate | C00680 | 3.12 | 4.69E-03 |
| Cholesterol | C00187 | 3.08 | 4.24E-04 |
| Chondroitin | C00401 | 3.08 | 3.83E-03 |
| Z-Gly-Pro-Leu-Gly-Pro | C03183 | 3.07 | 6.04E-03 |
| Nopaline | C01682 | 3.05 | 3.66E-03 |
| prasterone sulfate | C04555 | 3.05 | 5.82E-03 |
| Erythronolide B | C06635 | 2.99 | 1.91E-04 |
| Rec-beta-Tocopherol | C14152 | 2.99 | 1.90E-03 |
| 2-Arachidonoylglycerol | C13856 | 2.98 | 1.43E-02 |
| S-Adenosylmethioninamine | C01137 | 2.96 | 2.24E-02 |
| Daunorubicin | C01907 | 2.94 | 1.39E-02 |
| Epothilone C | C15694 | 2.93 | 1.33E-02 |
| O-1,4-α-L-Dihydrostreptosyl-streptidine 6-phosphate | C04767 | 2.93 | 4.17E-03 |
| germacradienol | C16143 | 2.92 | 2.17E-03 |
| Morphine 3-glucuronide | C16643 | 2.87 | 6.70E-03 |
| 1-Palmitoyl-2-(5-keto-8-oxo-6-octenoyl)-sn-glycero-3-phosphatidylcholine | C13902 | 2.86 | 6.36E-04 |
| (10S)-Juvenile hormone III diol phosphate | C16507 | 2.86 | 7.54E-02 |
| Kabiramide B |  | 2.85 | 1.12E-02 |
| Traumatic acid | C16308 | 2.85 | 3.97E-02 |
| 3alpha,7alpha,12alpha-trihydroxy-5alpha-cholan-24-yl sulfate | C16259 | 2.83 | 4.70E-03 |
| Urdamycinone B | C12404 | 2.83 | 1.56E-03 |
| Gambiriin A1 | C17772 | 2.77 | 5.33E-03 |
| Phorbol 12,13-dibutanoate | C03634 | 2.75 | 3.30E-04 |
| (S)-6-O-Methylnorlaudanosoline | C06517 | 2.73 | 2.66E-02 |

FIG. 19E

| Candidate Name | candidate_kegg | Log2Fold Change | pvalue |
| --- | --- | --- | --- |
| Amikacin | C06820 | 2.73 | 3.06E-03 |
| Nicotianamine | C05324 | 2.73 | 4.06E-02 |
| Tetracosatetraenoyl CoA | C16171 | 2.66 | 7.27E-03 |
| 27-O-Demethyl-rifamycin SV | C14727 | 2.65 | 2.87E-03 |
| beta-D-Glucosyl crocetin | C19867 | 2.64 | 2.60E-03 |
| Iokundjoside | C08874 | 2.63 | 2.01E-03 |
| trans,trans-Farnesyl phosphate | C20121 | 2.63 | 1.65E-02 |
| Horhammericine | C11677 | 2.60 | 2.25E-03 |
| 6,8a-Seco-6,8a-deoxy-5-oxoavermectin "2a" aglycone | C11969 | 2.55 | 2.18E-02 |
| Mascaroside | C09132 | 2.54 | 7.58E-02 |
| Tylactone | C12000 | 2.53 | 1.46E-02 |
| 13S-hydroperoxy-9Z,11E,14Z-octadecatrienoic acid | C04785 | 2.45 | 8.02E-03 |
| 6'-Dehydro-6'-oxoparomamine | C17583 | 2.43 | 9.23E-03 |
| Chlorobactane |  | 2.40 | 1.09E-02 |
| Linamarin | C01594 | 2.38 | 2.59E-02 |
| Avermectin A1a monosaccharide | C11982 | 2.38 | 2.32E-03 |
| (-)-Menthyl acetate | C09870 | 2.38 | 5.13E-03 |
| Glutathionylaminopropylcadaverine | C16566 | 2.37 | 7.15E-04 |
| S-Glutaryldihydrolipoamide | C06157 | 2.36 | 1.68E-02 |
| Chlorophyllide b | C16541 | 2.35 | 4.90E-03 |
| 3-Hydroxy-9,10-secoandrosta-1,3,5(10)-triene-9,17-dione | C19944 | 2.33 | 4.13E-02 |
| Ergosta-5,7,22,24(28)-tetraen-3β-ol | C05440 | 2.33 | 9.47E-04 |
| glycochenodeoxycholic acid 7-sulfate | C15559 | 2.32 | 2.53E-03 |
| LPA(0:0/16:0) | C00416 | 2.31 | 2.88E-04 |
| Cer(d16:1/23:0) |  | 2.31 | 1.83E-03 |
| N4-(b-N-Acetyl-D-glucosaminyl)-L-asparagine | C04540 | 2.30 | 8.20E-03 |
| 3-Oxo-delta4-steroid | C00619 | 2.28 | 8.69E-02 |
| D-Glucosaminide | C06023 | 2.28 | 3.31E-03 |
| Dinoprost (protaglandin F2-α) | C00639 | 2.27 | 3.71E-03 |
| Protorifamycin I | C12246 | 2.27 | 1.51E-03 |
| Pantetheine | C00831 | 2.27 | 1.68E-01 |
| 8,8a-Deoxyoleandolide | C11989 | 2.26 | 6.63E-03 |
| Deoxycytidine | C00881 | 2.25 | 9.08E-02 |
| Glycosyl-4,4'-diaponeurosporenoate | C16147 | 2.24 | 1.23E-03 |
| Methymycin | C11996 | 2.22 | 1.43E-02 |
| Demethylcitalopram | C16608 | 2.14 | 2.24E-02 |
| Albomaculine | C08515 | 2.14 | 1.42E-02 |
| L-Serine-phosphoethanolamine | C03872 | 2.10 | 1.31E-02 |
| L-N2-(2-Carboxyethyl)arginine | C06655 | 2.05 | 1.65E-03 |
| (2-Naphthyl)methanol | C02909 | 2.04 | 2.73E-02 |
| 5-(3'-Carboxy-3'-oxopropenyl)-4,6-dihydroxypicolinate | C05641 | 2.04 | 5.81E-02 |
| Ipecac (Emetamine) | C09420 | 2.02 | 2.28E-02 |
| PI(17:0/20:4(5Z,8Z,11Z,14Z)) |  | 2.01 | 1.01E-02 |
| Dihydropteroic acid | C00921 | 2.01 | 1.11E-02 |
| Desmosterol | C01802 | 2.01 | 6.82E-04 |

METHODS AND MATERIALS FOR USING BIOMARKERS WHICH PREDICT SUSCEPTIBILITY TO CLOSTRIDIUM DIFFICILE INFECTION

CROSS-REFERENCE TO RELATED APPLICATIONS

This application is a Continuation of U.S. application Ser. No. 15/762,203, filed Mar. 22, 2018, which is a National Stage application under 35 U.S.C. § 371 of International Application No. PCT/US2016/053073, having an International Filing Date of Sep. 22, 2016, which claims priority to U.S. Application Ser. No. 62/222,034, filed on Sep. 22, 2015. The disclosure of the prior applications are considered part of the disclosure of this application, and are incorporated in their entirety into this application.

BACKGROUND

1. Technical Field

This document relates to biomarkers of gut microbiota dysbiosis which can predict dysbiosis and/or predict susceptibility to *Clostridium difficile* infection, as well as compositions and methods for treating and/or preventing *C. difficile* infection.

2. Background Information

Hospital-acquired infections are a major cause of morbidity and mortality. *C. difficile* infections cause nearly half a million illnesses each year, and 1 in 11 people 65 and older died within a month of *C. difficile* infection diagnoses (Lessa et al. 2015 *N Engl J Med* 372:825-834). However, antibiotics reduce gut microbiome diversity, alter the metabolic landscape (Theriot et al. 2014 *Nat Commun* 5:3114-3114), and enable pathogen invasion—indicating that disturbances increase ecosystem vulnerability. Notably, risk factors associated with *C. difficile* infection (CDI) in humans extend beyond antibiotic use and include altered motility states such as diarrhea (Ferreyra et al. 2014 *Cell Host Microbe* 16:770-777).

SUMMARY

This document relates to biomarkers of gut microbiota dysbiosis. For example, this document provides biomarkers which predict susceptibility to CDI and targeted therapeutics to prevent CDI. Enteric pathogens can induce diarrhea (one of the most common symptoms of gastrointestinal disorders such as CDI), and can significantly remodel the gut microenvironment.

As described herein, a subset of patients with diarrhea has an altered gut microbiota (i.e., dysbiosis) relative to healthy individuals, but a gut microbiome that is similar to individuals with *C. difficile* infection. Bacteria that are increased or decreased in gut microbiota dysbiosis can be used as biomarkers to predict dysbiosis in patients with diarrhea and/or to predict susceptibility to CDI. In addition, provided herein are compositions including bacteria that are decreased in dysbiosis which can be used, for example, to restore heathy gut microbiota (e.g., by probiotic or by fecal microbiota transplant (FMT)) to prevent and/or treat CDI. For example, prophylactic FMT with a healthy microbial community restructured the metabolic landscape, restoring colonization resistance to *C. difficile*. A lack of colonization resistance, defined with simple stool metabolic parameters, can be an inherent phenotype of the microbiome, and can be corrected by introducing a diverse microbial community. The ability to identify at-risk individuals using simple noninvasive metrics and restore colonization resistance through FMT represents a novel approach to the prevention of diseases like CDI, especially among hospitalized and immunocompromised patients.

In general, one aspect of this document features a method for predicting dysbiosis in a mammal with diarrhea. The method includes, or consists essentially of, determining the amount of at least one biomarker of gut microbiota dysbiosis in a fecal sample obtained from the mammal and identifying the mammal as having dysbiosis if the amount of the at least one biomarker of gut microbiota is altered relative to a mammal without diarrhea. The alteration in gut microbiota can be a decrease in at least one of *Roseburia, Faecalibacterium, Akkermansia, Bacteroides,* or *Blautia*. The alteration in gut microbiota can be an increase in at least one of *Escherichia, Shigella, Enterobacter, Enterococcus,* or *Parasutterella*. In some cases, the alteration in gut microbiota can include both a decrease in at least one of *Roseburia, Faecalibacterium, Akkermansia, Bacteroides,* or *Blautia* and an increase in at least one of *Escherichia, Shigella, Enterobacter, Enterococcus,* or *Parasutterella*. The mammal can be a human. The human can exhibit at least one clinical biomarker of dysbiosis (e.g., current/recent hospitalization, immune suppression, recent/current antibiotic use, and prior *C. difficile* infection).

In another aspect, this document features a method for predicting susceptibility to *C. difficile* infection in a mammal with diarrhea. The method includes, or consists essentially of, determining the amount of at least one biomarker of gut microbiota dysbiosis in a fecal sample obtained from the mammal and identifying the mammal as having increased susceptibility to *C. difficile* infection if the amount of the at least one biomarker of gut microbiota is altered relative to a mammal without diarrhea. The alteration in gut microbiota can be a decrease in at least one of *Roseburia, Faecalibacterium, Akkermansia, Bacteroides,* or *Blautia*. The alteration in gut microbiota can be an increase in at least one of *Escherichia, Shigella, Enterobacter, Enterococcus,* or *Parasutterella*. In some cases, the alteration in gut microbiota includes both a decrease in at least one of *Roseburia, Faecalibacterium, Akkermansia, Bacteroides,* or *Blautia* and an increase in at least one of *Escherichia, Shigella, Enterobacter, Enterococcus,* or *Parasutterella*. The mammal can be a human. The human can exhibit at least one clinical biomarker of dysbiosis (e.g., current/recent hospitalization, immune suppression, recent/current antibiotic use, and prior *C. difficile* infection).

In another aspect, this document features a method for treating *C. difficile* infection in a mammal. The method includes, or consists essentially of, administering to the mammal a composition comprising at least three bacteria that are decreased in gut microbiota dysbiosis, wherein the at least three bacteria that are decreased in gut microbiota dysbiosis are selected from the group consisting of *Roseburia, Faecalibacterium, Akkermansia, Bacteroides, Blautia,* and *Bacteroides*. In some cases, the at least two bacteria that are decreased in gut microbiota dysbiosis include *Roseburia feacis, Faecalibacterium prausnitzii,* and optionally *Akkermansia muciniphila*. The method can include identifying said mammal as having said *C. difficile* infection prior to said administration. The mammal can be a human. The human can exhibit at least one clinical biomarker of dysbiosis (e.g., current/recent hospitalization, immune suppression, recent/current antibiotic use, and prior *C. difficile* infection).

Another aspect of this documents is a composition comprising at least two bacteria that are decreased in gut microbiota dysbiosis (e.g., *Roseburia, Faecalibacterium, Akkermansia, Bacteroides, Blautia*, and *Bacteroides*). In some cases, the at least three bacteria that are decreased in gut microbiota dysbiosis include *Roseburia feacis, Faecalibacterium prausnitzii*, and optionally *Akkermansia muciniphila*. The composition can be a pill, tablet, capsule, or enema. The composition is configured to deliver said at least three bacteria to the intestines of said mammal.

In another aspect, this document features a method for predicting susceptibility to *C. difficile* infection in a mammal with diarrhea. In some embodiments, the method includes, or consists essentially of, determining a level of at least one free amino acid in a fecal sample obtained from the mammal, and identifying the mammal as having increased susceptibility to *C. difficile* infection if the level of the at least one amino acid is altered relative to a mammal without diarrhea. The alteration in the free amino acid level can be an increase in the at least one amino acid. The at least one amino acid can include proline, alanine, glycine, histidine, isoleucine, leucine, methionine, phenylalanine, threonine, tryptophan, tyrosine, and/or valine. In some cases, the at least one amino acid is proline. In some embodiments, the method includes, or consists essentially of, determining a clinical risk factor profile, and identifying the mammal as having increased susceptibility to *C. difficile* infection if the mammal has at least one clinical risk factor. The at least one clinical risk factor can include current/recent hospitalization, immune suppression, current/recent antibiotic use, and/or prior *C. difficile* infection. In some embodiments, the method includes, or consists essentially of, determining a level of at least one short chain fatty acid (SCFA) in a fecal sample obtained from the mammal, and identifying the mammal as having increased susceptibility to *C. difficile* infection if the level of the at least one SCFA is altered relative to a mammal without diarrhea. The alteration in the SCFA level can be a decrease in the at least one SCFA. In some embodiments, the method includes, or consists essentially of, determining a level of at least one bile acid (BA) in a fecal sample obtained from the mammal, and identifying the mammal as having increased susceptibility to *C. difficile* infection if the level of the at least one BA is altered relative to a mammal without diarrhea. The BA can be cholic acid (CA), deoxycholic acid (DCA), lithocholic acid (LCA), or ursodeoxycholic acid (UDCA). The determining a level of at least one BA can include determining a level of CA, and determining a level of DCA, can further include determining a ratio of CA/DCA. The alteration in the BA level can be an increase in the ratio of CA/DCA.

In another aspect, this document features a method for preventing *C. difficile* infection in a mammal. The method includes, or consists essentially of, administering to the mammal a composition comprising at least two bacteria that are decreased in gut microbiota dysbiosis, where the at least two bacteria that are decreased in gut microbiota dysbiosis are selected from the group consisting of *Roseburia, Faecalibacterium, Akkermansia, Bacteroides, Blautia*, and *Bacteroides*. The at least two bacteria that are decreased in gut microbiota dysbiosis can include *Roseburia feacis* and *Faecalibacterium prausnitzii*. The composition can be administered by fecal microbiota transplant (FMT). The FMT can be administered by enema, colonoscope, nasogastric tube, or nasoduodenal tube. The method also can include identifying said mammal as having increased susceptibility to *C. difficile* infection prior to said administration (e.g., using any of the methods described herein). The mammal can be a human.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

dysbiotic microbial communities to communities from healthy controls and patients with CDI, overlaid numbers represent absolute numbers, with shading representative of frequency.

Figure 5:
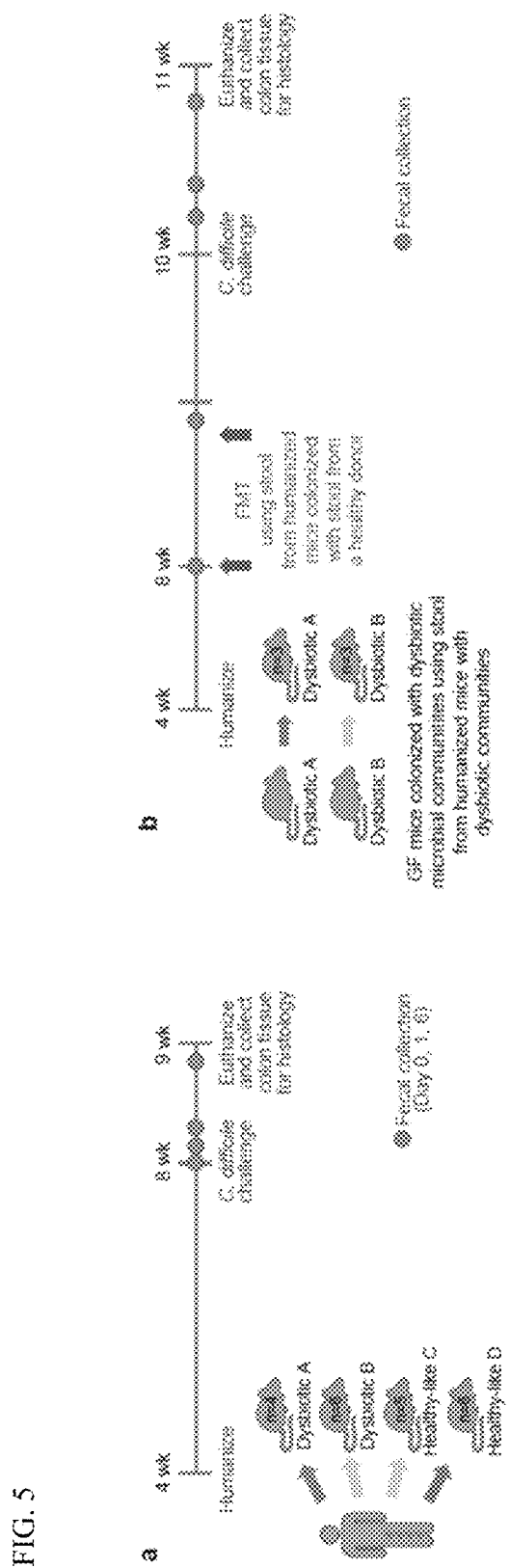

FIG. 5 shows experimental designs for ex-GF mouse experiments assessing *C. difficile* susceptibility. (A) Assessing susceptibility of humanized mice to CDI. (B) Assessing ability of FMT to protect dysbiotic animals from CDI.

Figure 6:
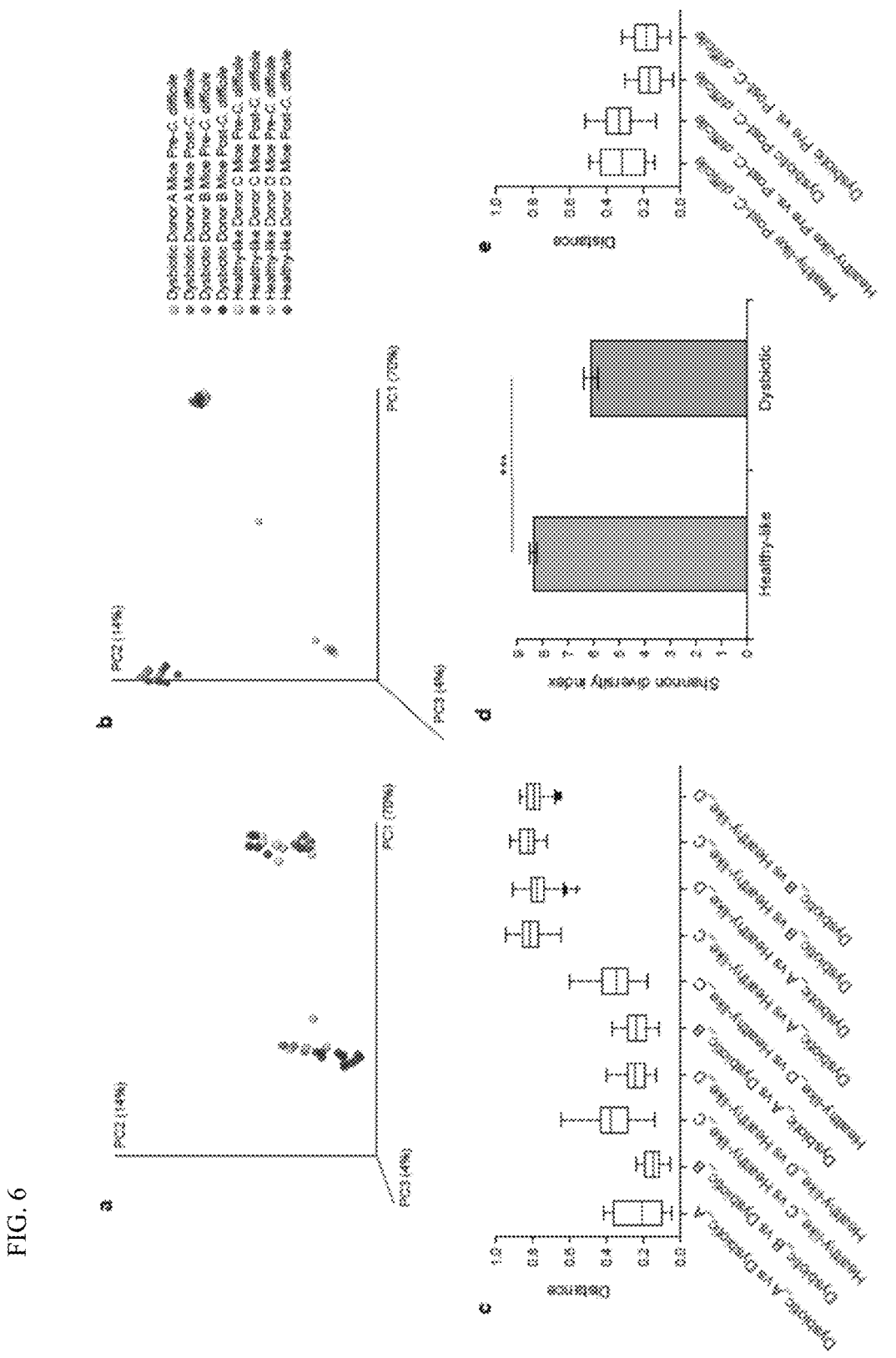

FIG. 6 shows humanized mice clusters by donor (dysbiotic or healthy-like) and dysbiotic mice show decreased diversity. (A) Weighted UniFrac and (B) unweighted UniFrac beta-diversity metric showing microbial communities from ex-GF humanized mice pre- and 2 days post-*C. difficile* challenge. (C) Distances (weighted UniFrac) within dysbiotic and healthy-like mouse groups compared to distances between dysbiotic and healthy-like mice (within group vs. between dysbiotic/healthy-like groups: Bonferroni-corrected $p<0.0001$, t-test). (D) Alpha-diversity in humanized mice with dysbiotic and healthy-like microbial communities (plotted averages with SEM, ***$p<0.0001$, t-test). (E) Distances (weighted UniFrac) within dysbiotic and healthy-like microbial communities 2 days post-*C. difficile* challenge compared to distances between the microbial communities pre- and 2 days post-*C. difficile* challenge (dysbiotic, Bonferroni-corrected $p=1$, healthy-like, Bonferroni-corrected $p=1$, t-test).

Figure 7:
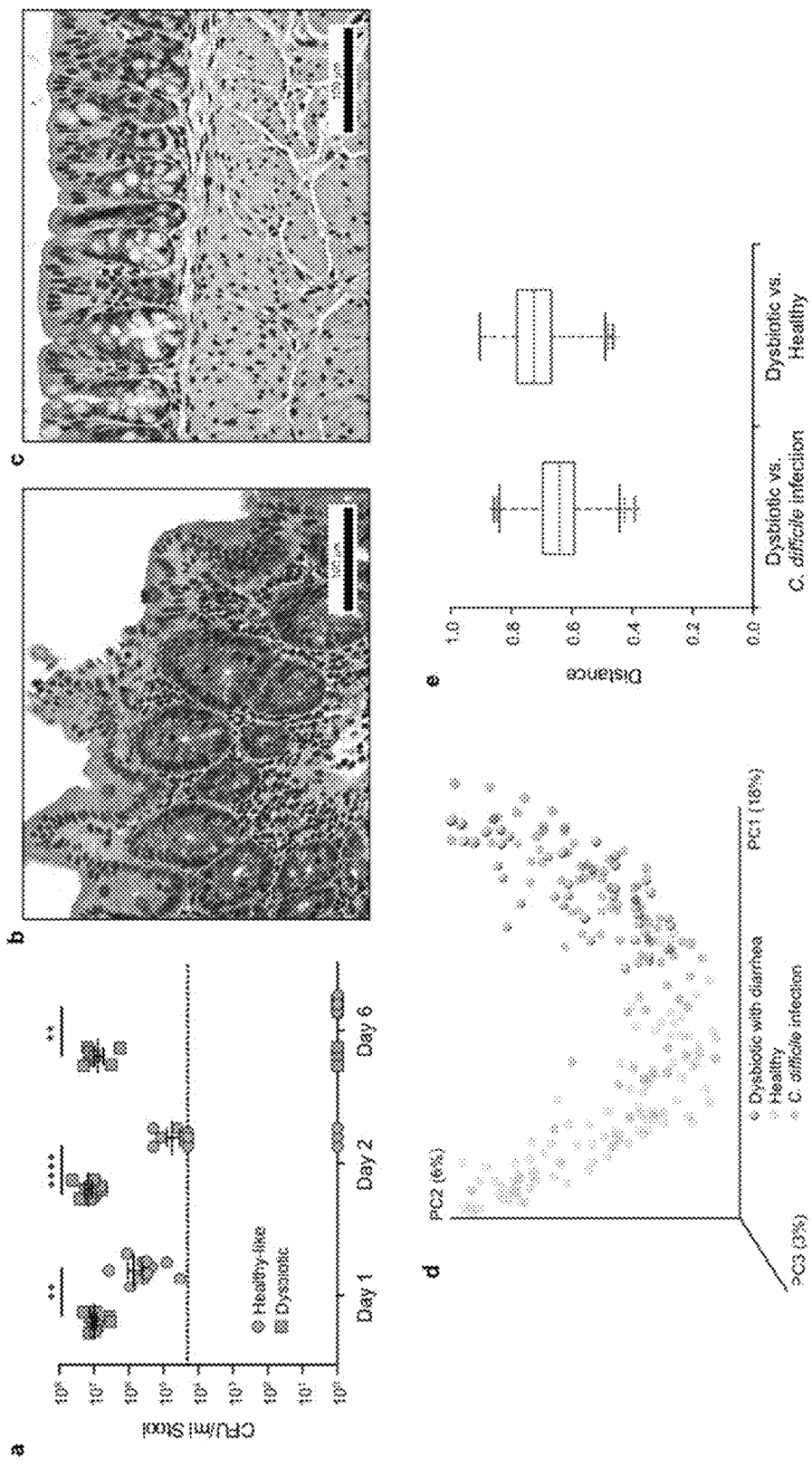

FIG. 7 shows that mice with dysbiotic microbial communities exhibit loss of colonization resistance to *C. difficile*. (A) *C. difficile* CFUs in stool of ex-GF mice colonized with healthy-like (n=11) or dysbiotic (n=10) microbial communities. Data points represent individual animals with lines indicating average and SEM. Assay limit of detection (LOD) indicated by a dashed horizontal line at $2\times10^4$ ($p<0.005$, **$p<0.00005$, two-way ANOVA). (B) Representative H&E-stained proximal colon of mice colonized with dysbiotic or (C) healthy-like communities. (D) Beta-diversity (unweighted UniFrac) of healthy individuals and patients with diarrhea (n=115) and CDI (n=95). (E) Unweighted UniFrac distance between dysbiotic individuals and healthy controls and patients with CDI (plotted are median with IQR and SD, Bonferroni-corrected $p<0.0001$, t-test).

Figure 8:
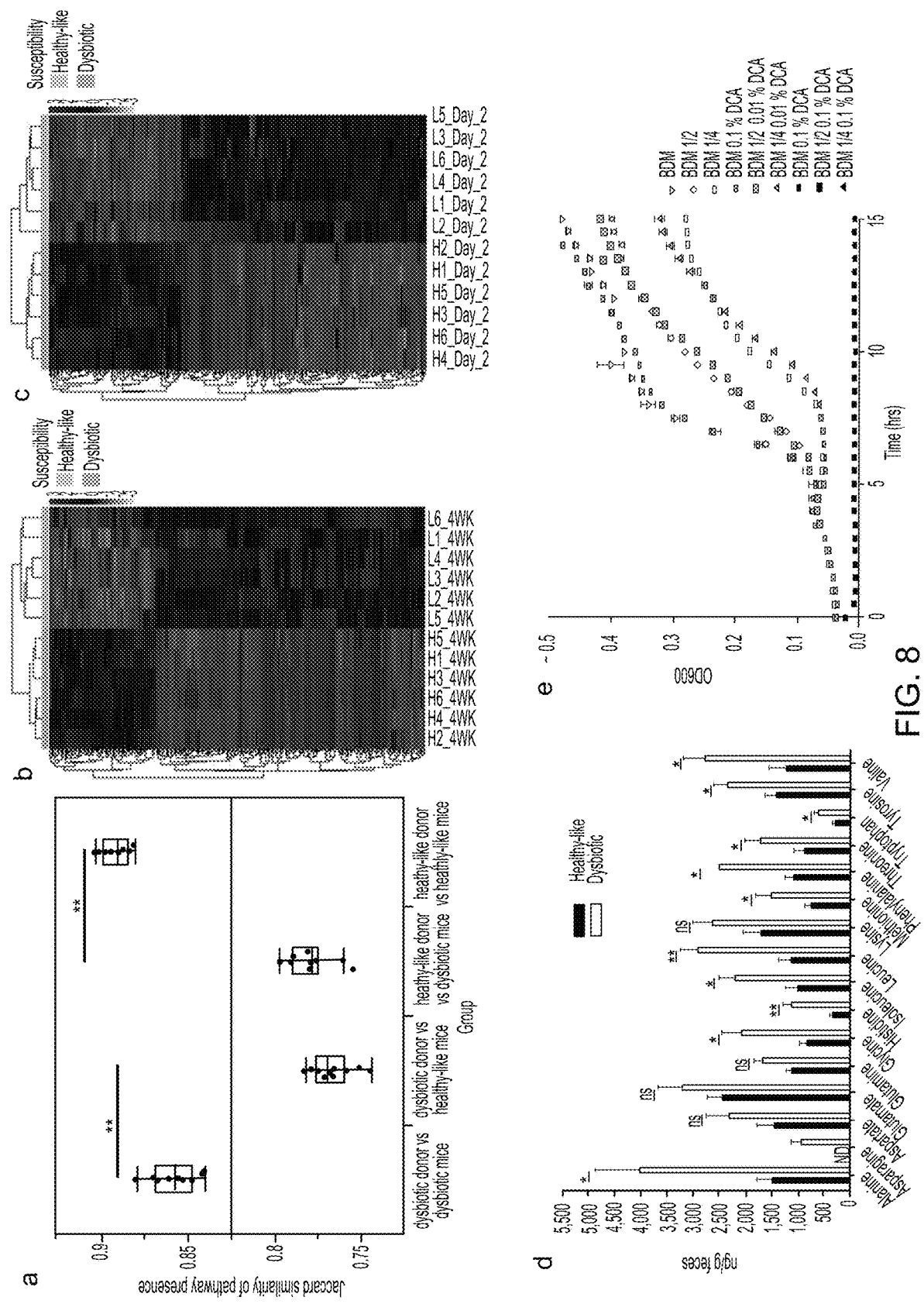

FIG. 8 shows differences in whole community pathway expression and metabolites pre- and 2 days post-*C. difficile* challenge in healthy-like and dysbiotic communities. (A) Distance box plots based on Jaccard similarity of pathway presence between human donors and representative humanized mice (**$p<0.001$, Wilcoxon rank-sum test). Significant differences in pathway expression (DEseq2 v.1.8.2, $p<0.05$). (B) Pre-*C. difficile* challenge (4 weeks post-humanization) and (C) 2 days post-*C. difficile* challenge from ex-GF mice colonized with healthy-like (n=6) or dysbiotic (n=6) donor (D) AA, in stool with healthy-like (n=11) or dysbiotic (n=10) microbial communities (plotted averages with SEM, *$p<0.05$, **$p<0.005$, ns—not significant, ND—not detected, Mann-Whitney.) (E) *C. difficile* growth kinetics in basal defined medium (BDM) with 0%, 0.1% or 0.01% DCA and AA concentrations at full, ½ and ¼ of the standard AA concentration (plotted averages with SEM).

Figure 9:
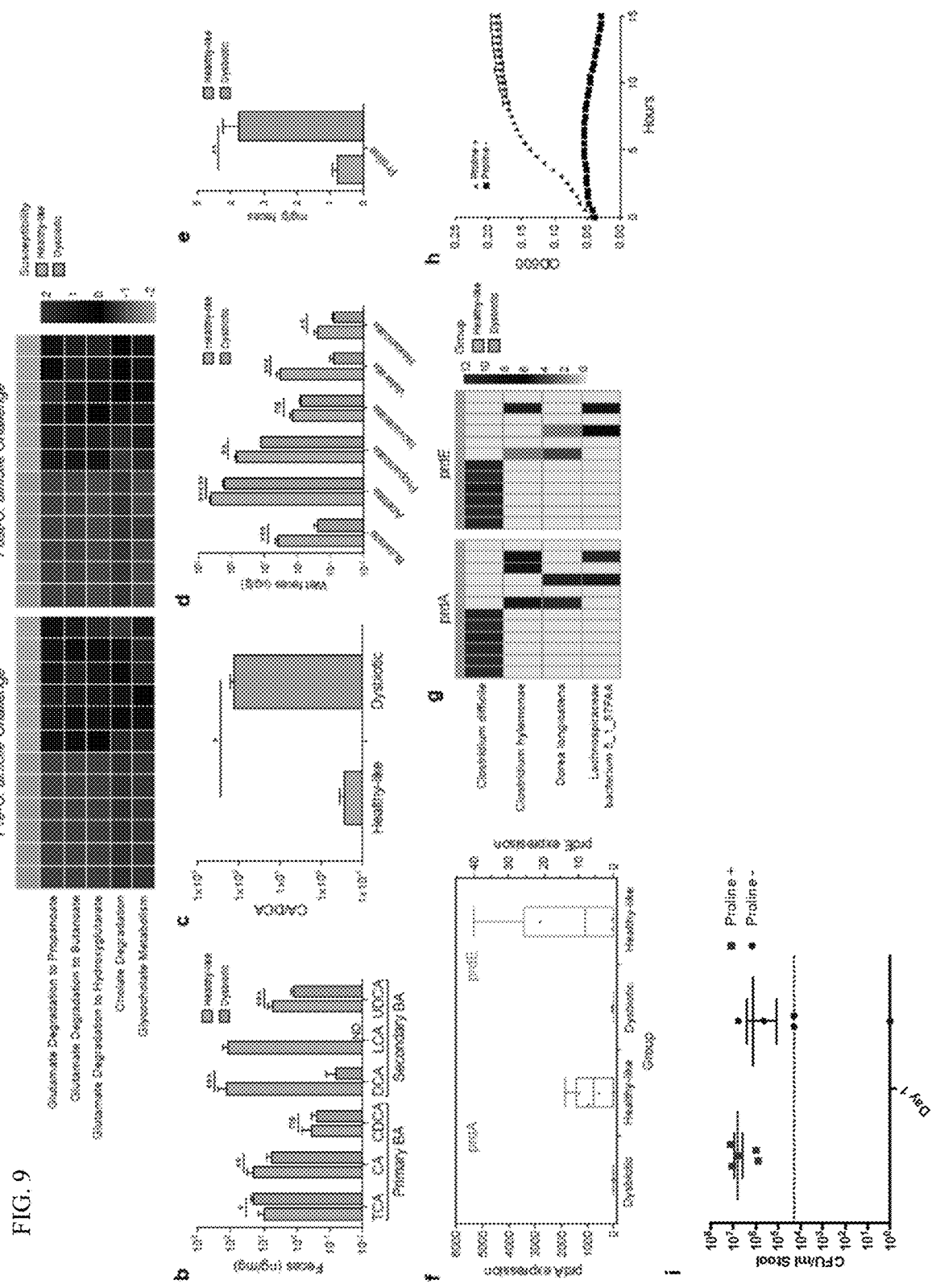

FIG. 9 shows metatranscriptomics and metabolomics reveal secondary bile acid (BAs) and short chain fatty acids (SCFAs) as inhibitors and amino acids (AAs) as promoters of *C. difficile* colonization. (A) A subset of pathway expression based on whole community gene expression (RNAseq) pre- and 2 days post-*C. difficile* challenge from ex-GF mice colonized with healthy-like (n=10) or dysbiotic (n=11) communities. (B) Primary and secondary BA. (C) Ratio of cholic acid (CA)/deoxycholic acid (DCA). (D) SCFA and (E) proline in stool from humanized mice with healthy-like (n=11) or dysbiotic (n=10) communities (plotted mean with SEM, *$p<0.05$, $p<0.005$, *$p<0.0005$, *****$p<0.00005$, ns—not significant, ND—not detected; Mann-Whitney). (F) prdA and prdE gene expression in humanized mice with healthy-like and dysbiotic communities (points represent total RNAseq reads with lines at median with IQR and SD). (G) prdA and prdE gene expression by taxonomic ID in dysbiotic and healthy-communities at day 2 post-*C. difficile* challenge (Log 2 transformed absolute counts). (H) *C. difficile* growth kinetics in the presence or absence of proline in BDM without glucose (plotted averages with SEM). (I) *C. difficile* colonization levels in animals maintained on proline$^+$ or proline$^-$ diets. Data points represent individual animals with lines indicating average and SEM. Assay limit of detection (LOD) indicated by a dashed horizontal line at $2\times10^4$ (*$p<0.05$).

Figure 10:
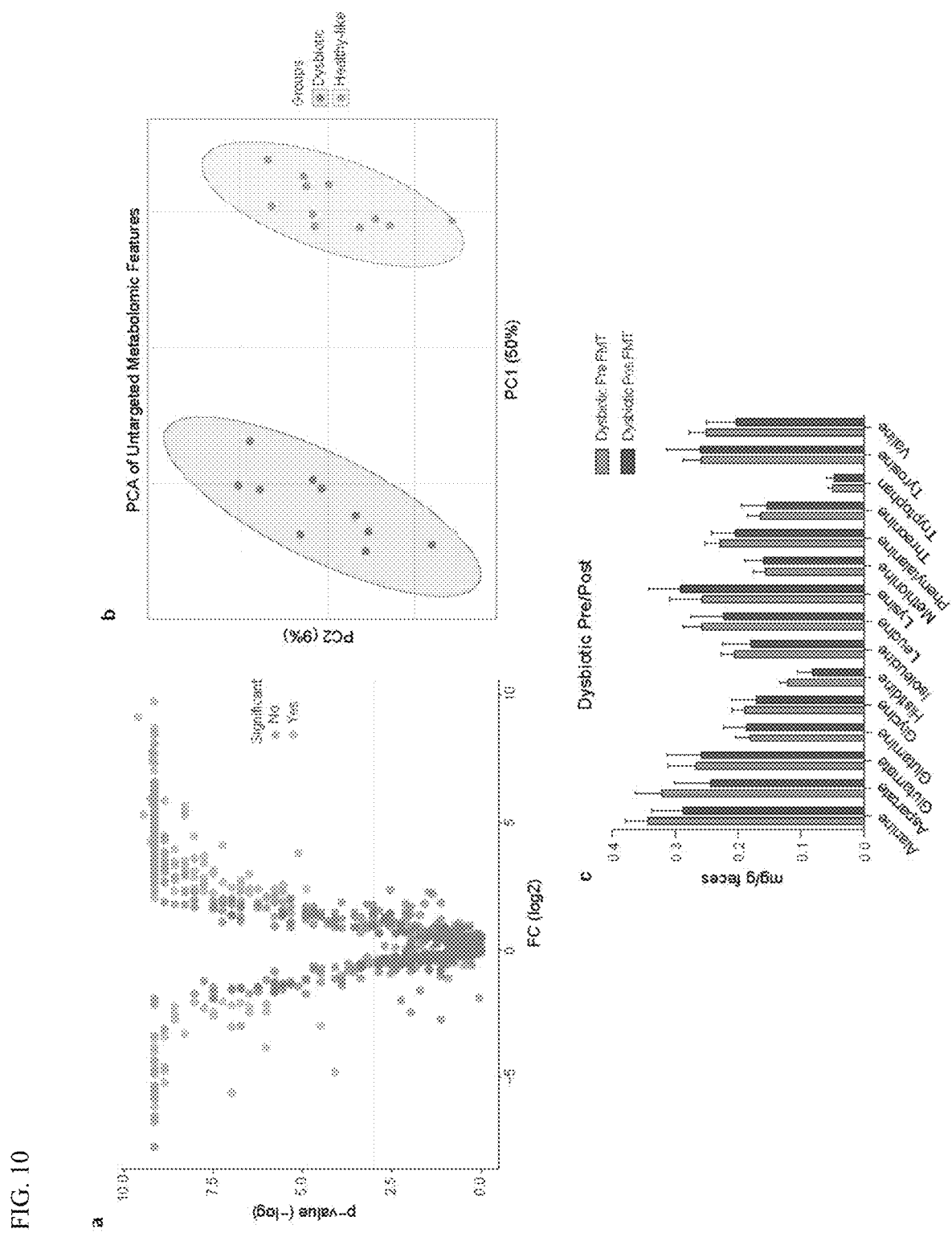

FIG. 10 shows functional changes based on metabolomics. (A) Volcano plot of compounds detected using UPLC-MS in stool samples collected from ex-GF mice colonized with healthy-like (n=11) or dysbiotic (n=10) communities. Compounds with a Log 2 fold change>1 and $p<0.05$ (Kruskal-Wallis H-Tests) are shown. (B) Principal component analysis (PCA) based on log transformed differences in metabolite profiles in healthy-like and dysbiotic communities, ellipses represent 95% confidence intervals. (C) $H^1$-NMR of stool samples quantitating AA content in stool collected from dysbiotic humanized animals collected pre/post-FMT (plotted averages with SEM).

Figure 11:
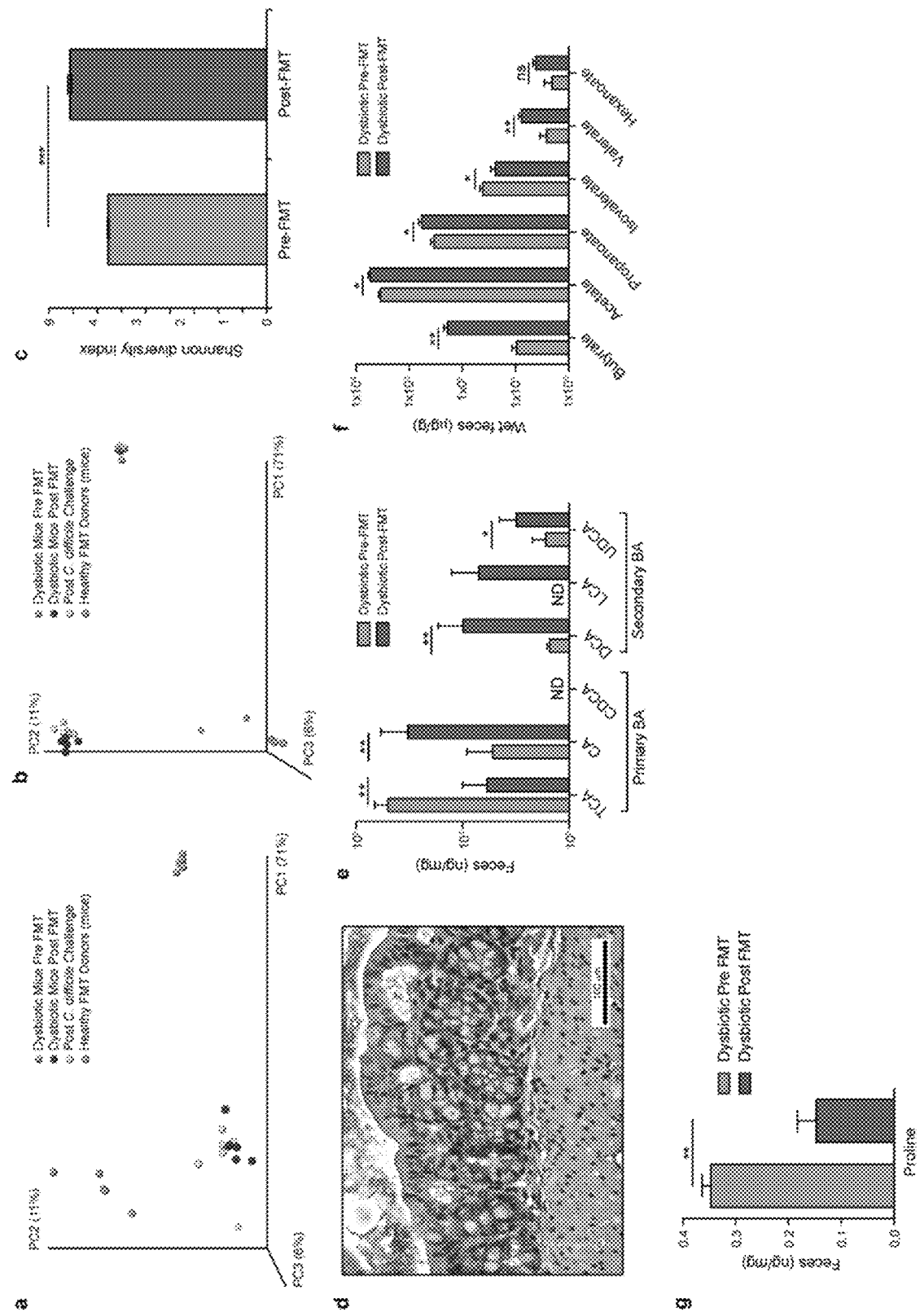

FIG. 11 shows colonization resistance is restored in dysbiotic mice post-FMT with significant increases in BAs, SCFAs and decrease in proline. (A) Weighted and (B) unweighted UniFrac beta diversity metric showing microbial communities pre- and post-FMT (n=6; within pre-FMT samples vs. distance between pre- and post-FMT samples, Bonferroni-corrected $p<0.0001$, t-test, based on weighted UniFrac). (C) Pre- and post-FMT alpha-diversity in dysbiotic mice (n=6, ***$p<0.0005$, t-test). (D) Representative H&E-stained proximal colon of ex-GF mice with dysbiotic communities, post-FMT, post-*C. difficile* challenge. (E) BA, (F) SCFA, and (G) proline in stool pre- and post-FMT (plotted averages with SEM; *$p<0.05$, **$p<0.005$, Mann-Whitney).

FIG. 12 is a table showing humanization efficiency for mice at the family level.

FIG. 13 is a table showing colon inflammation scores in dysbiotic and healthy-like mice post-*C. difficile* challenge.

FIGS. 14A-14B contain a table showing upregulated pathways in dysbiotic communities at 4 weeks post-humanization (pre-*C. difficile* challenge).

FIGS. 15A-15F contain a table showing upregulated pathways in healthy-like communities at 4 weeks post-humanization (pre-*C. difficile* challenge).

FIGS. 16A-16E contain a table showing upregulated pathways in healthy-like communities at day 2 post-*C. difficile* challenge.

FIGS. 17A-17B contain a table showing upregulated pathways in dysbiotic communities at day 2 post-*C. difficile* challenge.

FIGS. 18A-18B contain a table showing metabolites found in higher concentrations in healthy-like communities at 4-weeks post-humanization (pre-*C. difficile* challenge).

FIGS. 19A-19E contain a table showing metabolites found in higher concentrations in dysbiotic communities at 4 weeks post-humanization (pre-*C. difficile* challenge).

Figure 20:
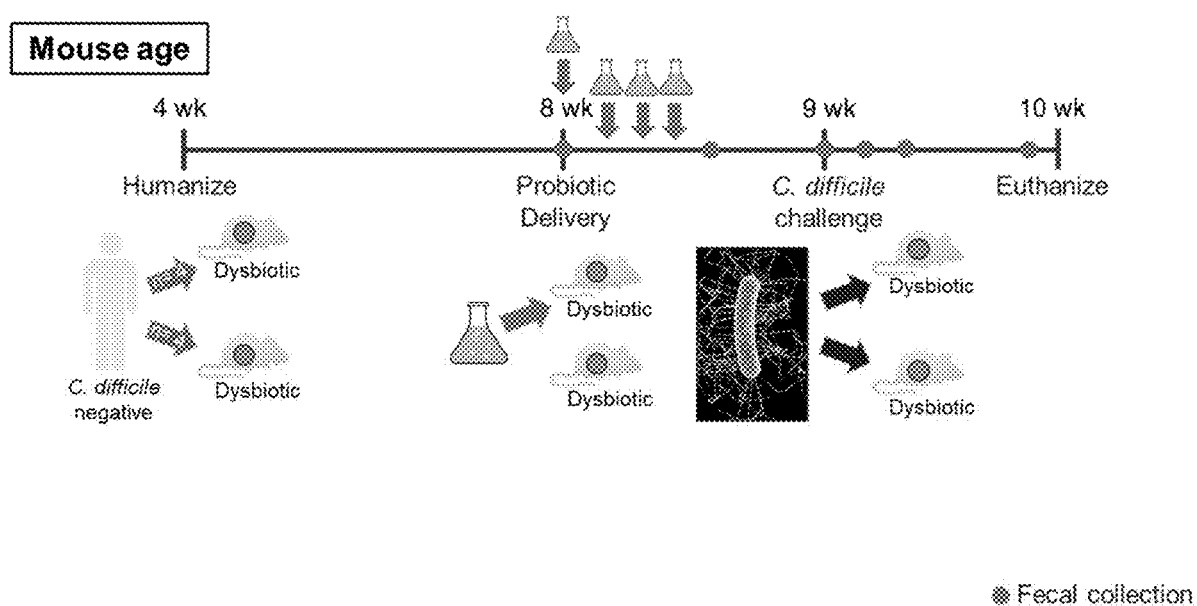

FIG. 20 shows an experimental time line for probiotic delivery to mice of gut microbiota from human patients.

DETAILED DESCRIPTION

This document provides materials and methods related to preventing and/or treating *C. difficile* infection (CDI). In some cases, this document provides methods for predicting dysbiosis in patients with gastrointestinal disorders, to treat gastrointestinal disorders (e.g., diarrhea that is not related to a pathogenic bacteria) and/or to prevent pathogenic infection (e.g., by *C. difficile*) of the gut. For example, dysbiosis associated with susceptibility to CDI can be treated using a bacterial composition described herein.

The ability to determine a clinical risk factor profile can help identify patients with diarrhea and dysbiosis who may be at higher risk of CDI (e.g., patients having irritable bowel disease, patients who are immunosuppressed, and/or hospitalized patients).

Biomarkers

A biological marker, or "biomarker," as used herein refers to a measurable marker that can be used as an indicator of gut microbiota dysbiosis (e.g., in a mammal with diarrhea). The amount or level of a biomarker can be altered (e.g., increased or decreased) in gut microbiota dysbiosis relative to a healthy mammal (e.g., mammal without diarrhea). For example, an altered amount or level of a biomarker described herein can be used to predict susceptibility to *C. difficile* infection in a mammal (e.g., a mammal with diarrhea).

In some cases, a biomarker that can be used indicate gut microbiota dysbiosis (e.g., to predict susceptibility to *C. difficile* infection) in a mammal can be one or more (e.g., at least one, at least two, at least three, at least four, or more) bacteria. In some cases, bacteria can be decreased in gut microbiota dysbiosis. Examples of bacteria that can be decreased in gut microbiota dysbiosis include, without limitation, bacteria belonging to the genera *Roseburia, Faecalibacterium, Akkermansia, Bacteroides, Blautia*, and *Bacteroides*. In some embodiments, biomarkers that are decreased in gut microbiota dysbiosis include bacteria belonging to the genera *Roseburia, Faecalibacterium*, and *Akkermansia*. For example, biomarkers that are decreased in gut microbiota dysbiosis can include *Roseburia feacis, Faecalibacterium prausnitzii*, and *Akkermansia muciniphila*. In some cases, bacteria can be increased in gut microbiota dysbiosis. Examples of biomarkers that can be increased in gut microbiota dysbiosis include, without limitation, bacteria belonging to the genera *Escherichia Shigella, Enterobacter, Enterococcus, Parasutterella*, and *Bacteroides*.

In some cases, a biomarker that can be used indicate gut microbiota dysbiosis (e.g., to predict susceptibility to *C. difficile* infection) in a mammal can be one or more (e.g., at least one, at least two, at least three, at least four, or more) free AAs. A free AA can be any appropriate amino acid. A free AA can be a naturally occurring AA. A free AA can be an L- or a D-AA. A free AA can be increased in gut microbiota dysbiosis. Examples of free AAs include, without limitation, proline, alanine, glycine, histidine, isoleucine, leucine, methionine, phenylalanine, threonine, tryptophan, tyrosine, and valine. In some cases, an increased level of free proline can be used to predict susceptibility to *C. difficile* infection in a mammal.

In some cases, a biomarker that can be used indicate gut microbiota dysbiosis and/or to predict susceptibility to *C. difficile* infection in a mammal can be one or more (e.g., at least one, at least two, at least three, at least four, or more) SCFAs. A SCFA can be any appropriate SCFA. A free SCFA can be increased or decreased in gut microbiota dysbiosis. For example, a SCFA can be decreased in gut microbiota dysbiosis. Examples of additional SCFAs include, without limitation, butyrate, propionate, acetate, valerate, and hexanoate.

In some cases, a biomarker that can be used to indicate gut microbiota dysbiosis and/or to predict susceptibility to *C. difficile* infection in a mammal can be one or more (e.g., at least one, at least two, at least three, at least four, or more) BAs (e.g., a primary BA or a secondary BA). A BA can be increased or decreased in gut microbiota dysbiosis. Examples of primary BAs include, without limitation, taurocholic acid (TA or TCA), cholic acid (CA), and chenodeoxycholic acid (CDCA). Examples of secondary BAs include, without limitation, deoxycholic acid (DCA), lithocholic acid (LCA), ursodeoxycholic acid (UDCA), and taurodeoxycholic acid (TDCA). For example, a decreased level of DCA and/or LCA can be used to predict susceptibility to *C. difficile* infection in a mammal. For example, an increased level of TCA can be used to predict susceptibility to *C. difficile* infection in a mammal. In some cases, a ratio of a primary BA (e.g., CA) to a secondary BA (e.g., CDA) can be used to indicate gut microbiota dysbiosis and/or to predict susceptibility to *C. difficile* infection in a mammal. For example, an increased ratio of CA/CDA can be used to predict susceptibility to *C. difficile* infection in a mammal.

Compositions

Provided herein are bacterial compositions including bacteria that are decreased in gut microbiota dysbiosis. A bacterial composition can include bacteria derived (e.g., obtained) from one or more healthy donors. A bacterial composition can include at least two (e.g., two, three, four, five, or more) bacteria that are decreased in gut microbiota dysbiosis. For example, a bacterial composition provided herein can include at least two bacteria that are decreased in gut microbiota dysbiosis. Examples of bacteria that can be used as described herein include, without limitation, those belonging to the genera *Prevotella, Bacteroides, Clostridium, Faecalibacterium, Eubacterium, Ruminococcus, Peptococcus, Peptostreptococcus, Bifidobacterium, Escherichia, Lactobacillus, Akkermansia*, and *Roseburia*. In some cases, at least two bacteria that are decreased in gut microbiota dysbiosis are selected from the genera *Roseburia, Faecalibacterium, Bacteroides, Blautia*, and *Bacteroides*. In some embodiments, a composition described herein can include *Roseburia feacis* and *Faecalibacterium prausnitzii*. In some cases, at least two bacteria that are decreased in gut microbiota dysbiosis are selected from the genera *Roseburia, Faecalibacterium, Akkermansia, Bacteroides, Blautia*, and *Bacteroides*. In some embodiments, a composition described herein can include *Roseburia feacis, Faecalibacterium prausnitzii*, and *Akkermansia muciniphila*.

A composition containing at least two bacteria that are decreased in gut microbiota dysbiosis can contain one or more additional probiotic microorganisms. Examples of other probiotic microorganisms that can be included within a composition containing at least two bacteria that are decreased in gut microbiota dysbiosis include, without limitation, *Prevotella coprii, Bifidobacterium infantis, Lactobacillus rhamnosis Lactobacillus plantarum, Bifidobacterium breve, Bifidobacterium longum, Lactobacillus acidophilus, Lactobacillus paracasei, Lactobacillus bulgaricus, Streptococcus thermophilus*, and *Faecalibacterium prauznitzii*.

Compositions provided herein can include any amount of bacteria described herein. In some cases, a composition provided herein can contain bacteria (e.g., *Roseburia feacis, Faecalibacterium prausnitzii*, and optionally *Akkermansia muciniphila*) in an amount such that from about 0.001 to about 100 percent (e.g., from about 1 percent to about 95 percent, from about 10 to about 95 percent, from about 25 to about 95 percent, from about 50 to about 95 percent, from about 20 to about 80 percent, from about 50 to about 95 percent, from about 60 to about 95 percent, from about 70 to about 95 percent, from about 80 to about 95 percent, from about 90 to about 95 percent, from about 95 to about 99 percent, from about 50 to about 100 percent, from about 60 to about 100 percent, from about 70 to about 100 percent, from about 80 to about 100 percent, from about 90 to about 100 percent, or from about 95 to about 100 percent), by weight, of the composition can be bacteria. In some cases, a composition provided herein can contain from about $10^3$ to about $10^8$ bacteria.

In some cases, a composition provided herein can contain bacteria (e.g., *Roseburia feacis*, *Faecalibacterium prausnitzii*, and optionally *Akkermansia muciniphila*) in the amounts and dosages as described elsewhere for probiotic bacteria (U.S. Patent Application Publication No. 2008/0241226; see, e.g., paragraphs [0049-0103]). In addition, a composition provided herein containing bacteria (e.g., *Roseburia feacis*, *Faecalibacterium prausnitzii*, and *Akkermansia muciniphila*) can be administered as described elsewhere for probiotic bacteria (U.S. Patent Application Publication No. 2008/0241226; see, e.g., paragraphs [0049-0103]).

Bacteria can be obtained from the digestive system of any appropriate mammal (e.g., a human). For example, bacteria that are decreased in gut microbiota dysbiosis (e.g., *Roseburia feacis*, *Faecalibacterium prausnitzii*, and optionally *Akkermansia muciniphila*) can be isolated from small intestinal mucosa (e.g., a small bowel biopsy or aspirate sample) of a human (e.g., a healthy human patient). Bacterial strains (e.g., *Roseburia feacis*, *Faecalibacterium prausnitzii*, and optionally *Akkermansia muciniphila*) can be identified via 16S rRNA PCR using 16S rRNA primers. In some cases, bacteria can be commercially obtained (e.g., from the American Type Culture Collection).

Any appropriate method can be used to obtain a culture of bacteria. For example, microbial culturing techniques can be used to obtain bacteria. In general, bacteria can be cultured in broth containing milk (e.g., skim milk) to obtain a culture containing greater than $1\times10^8$ bacteria per mL of broth. The bacteria can be removed from the broth via centrifugation. Once obtained, the bacteria can be formulated into a medicament or nutritional supplement composition for administration to a mammal (e.g., a human), can be added to a food product for consumption, or can be frozen for later use.

In some cases, a preparation of bacteria, which can be stored frozen in 2× skim milk, can be thawed and grown on CDC Anaerobe Laked Sheep Blood Agar with kanamycin and vancomycin (KV) (Becton, Dickson and Company, Sparks, MD, product number 221846) in an anaerobe jar with AnaeroPack System (product number 10-01, Mitsubishi Gas Chemical America, Inc., New York, NY). The culture can be incubated at 35-37° C. for at least 48 hours.

A composition containing at least two bacteria that are decreased in gut microbiota dysbiosis can be in the form of a medicament or nutritional supplement. For example, compositions containing at least two bacteria that are decreased in gut microbiota dysbiosis can be in the form of a pill, tablet, powder, liquid, capsule, or enema. A medicament or nutritional supplement can be prepared with pharmaceutically acceptable excipients such as binding agents, fillers, lubricants, disintegrants, or wetting agents. In some cases, medicaments or nutritional supplements (e.g., tablets) can be coated. In some cases, a composition containing at least two bacteria that are decreased in gut microbiota dysbiosis can be formulated such that the bacteria are encapsulated for release within the intestines of a mammal. Liquid preparations for administration can take the form of, for example, solutions, syrups, or suspension, or they can be presented as a dry product for constitution with saline or other suitable liquid vehicle before use. In some cases, a composition provided herein containing at least at least two bacteria that are decreased in gut microbiota dysbiosis (e.g., *Roseburia feacis*, *Faecalibacterium prausnitzii*, and optionally *Akkermansia muciniphila*) can be in a dosage form as described elsewhere (U.S. Patent Application Publication No. 2008/0241226; see, e.g., paragraphs [0129-0135]). For example, a composition provided herein can be in the form of a food product formulated to contain at least two bacteria that are decreased in gut microbiota dysbiosis (e.g., *Roseburia feacis*, *Faecalibacterium prausnitzii*, and optionally *Akkermansia muciniphila*). Examples of such food products include, without limitation, milk (e.g., acidified milk), yogurt, milk powder, tea, juice, beverages, candies, chocolates, chewable bars, cookies, wafers, crackers, cereals, treats, and combinations thereof.

A composition containing at least two bacteria that are decreased in gut microbiota dysbiosis can contain other ingredients such as buffers, radical scavengers, antioxidants, reducing agents, or mixtures thereof. Examples of other additional ingredients that can be formulated into a single composition or a separate composition for delivery to a mammal (e.g., a human) include, without limitation, those ingredients described elsewhere (U.S. Patent Application Publication No. 2008/0241226; see, e.g., paragraphs [0104-0128]).

In some cases, a composition containing at least two bacteria that are decreased in gut microbiota dysbiosis can contain a pharmaceutically acceptable carrier for administration to a mammal, including, without limitation, sterile aqueous or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Pharmaceutically acceptable carriers also can include physiologically acceptable aqueous vehicles (e.g., physiological saline) or other known carriers for oral administration.

Methods

Provided herein are methods for using the biomarkers described herein. The methods include determining the amount of at least one biomarker of gut microbiota dysbiosis. In some embodiments, this disclosure provides methods of predicting dysbiosis in a mammal with diarrhea. In some embodiments, this disclosure provides methods of predicting susceptibility to CDI in a mammal with diarrhea. In some embodiments, this disclosure provides methods of treating and/or preventing CDI in a mammal with dysbiosis.

Methods provided herein can include, for example, determining the amount of at least one biomarker (e.g., determining the amount of 1 or more biomarkers, 2 or more biomarkers, 3 or more biomarkers, 4 or more biomarkers, 5 or more biomarkers, 6 or more biomarkers, 7 or more biomarkers, or 8 or more biomarkers) of gut microbiota dysbiosis in a fecal (i.e., stool) sample obtained from a mammal. In some cases, the methods can include identifying the mammal as having dysbiosis if the amount of the at least one biomarker of gut microbiota is altered relative to a mammal without diarrhea. In some cases, the methods can include identifying the mammal as susceptible to CDI if the amount of the at least one biomarker of gut microbiota is altered relative to a mammal without diarrhea. A mammal (e.g., a mammal with diarrhea) can have increased susceptibility to *C. difficile* infection if the level of the at least one amino acid is altered in a sample from the mammal (e.g., a fecal sample) relative to a mammal without diarrhea. For example, a mammal can have increased susceptibility to *C. difficile* infection if the level of proline in the sample is increased. A mammal (e.g., a mammal with diarrhea) can have increased susceptibility to *C. difficile* infection if the mammal has at least one clinical risk factor. For example, a mammal can have increased susceptibility to *C. difficile* infection if the mammal has one or more of current/recent hospitalization(s), immune suppression, current/recent antibiotic use, and prior *C. difficile* infection(s). A mammal (e.g., a mammal with diarrhea) can have increased susceptibility to *C. difficile* infection if the level of the at least one SCFA or BA is altered in a sample from the mammal (e.g., a fecal sample) relative to a mammal without diarrhea. For example, a mammal can have increased susceptibility to *C. difficile* infection if the level of CA, DCA, LCA, and/or UDCA is decreased in the sample. For example, a mammal can have increased susceptibility to *C. difficile* infection if the ratio of CA/DCA in increased in the sample.

The alteration in the gut microbiota is altered relative to a mammal without diarrhea. In some embodiments, the alteration in gut microbiota can be a decrease in at least one of biomarkers described herein. For example, the alteration in gut microbiota can be a decrease in at least one of *Roseburia, Faecalibacterium, Akkermansia, Bacteroides*, or *Blautia*. In some embodiments, the alteration in gut microbiota is an increase in at least one of biomarkers described herein. For example, the alteration in gut microbiota can be an increase in at least one of *Escherichia, Shigella, Enterobacter, Enterococcus*, or *Parasutterella*. In some embodiments, the alteration in gut microbiota includes both a decrease in at least one of *Roseburia, Faecalibacterium, Akkermansia, Bacteroides*, or *Blautia* and an increase in at least one of *Escherichia, Shigella, Enterobacter, Enterococcus*, or *Parasutterella*.

Also provided herein are methods of using compositions including at least two bacteria that are decreased in gut microbiota dysbiosis (e.g., *Roseburia feacis, Faecalibacterium prausnitzii*, and optionally *Akkermansia muciniphila*). The methods include administering to a mammal a composition described herein. For example, compositions including at least two bacteria that are decreased in gut microbiota dysbiosis can be used to restore heathy gut microbiosis (e.g., by probiotic or by FMT) to treat *C. difficile* infection in a mammal.

In some embodiments, this disclosure provides methods of treating CDI in a mammal (e.g., a mammal having dysbiosis). Treating CDI can include prophylactic treatment (i.e., delivered prior to the development of symptoms to prevent a disease from occurring) or therapeutic treatment (i.e., delivered after development of symptoms). For example, a method of preventing CDI in a mammal having dysbiosis can include administering by FMT a composition described herein (e.g., including *Roseburia feacis, Faecalibacterium prausnitzii*, and optionally *Akkermansia muciniphila*) that was derived from a healthy donor.

A composition as described herein can include at least two bacteria selected from the groups consisting of *Roseburia, Faecalibacterium, Akkermansia, Bacteroides, Blautia*, and *Bacteroides*). In some embodiments, the composition includes *Roseburia feacis, Faecalibacterium prausnitzii*, and optionally *Akkermansia muciniphila*.

A composition can be administered by any suitable means. In some embodiments, a composition can be administered orally (e.g., via a pill, tablet, or capsule). In other embodiments, a composition can be administered by FMT (e.g., via enema, colonoscope, nasogastric tube, or nasoduodenal tube).

In some embodiments, methods provided herein can also include identifying a mammal as being susceptible to *C. difficile* infection or as having said *C. difficile* infection prior to administering to the mammal a composition described herein. In some cases, a mammal (e.g., a mammal with diarrhea) can be identified as having increased susceptibility to *C. difficile* infection using the biomarkers and methods described herein. For example, a mammal can be identified as having increased susceptibility to *C. difficile* infection if the level of at least one amino acid (e.g., proline) is altered (e.g., increased) in a sample from the mammal (e.g., a fecal sample) relative to a mammal without diarrhea. For example, a mammal can be identified as having increased susceptibility to *C. difficile* infection if the mammal has at least one clinical risk factor (e.g., one or more of current/recent hospitalization(s), immune suppression, current/recent antibiotic use, and prior *C. difficile* infection(s)). For example, a mammal can be identified as having increased susceptibility to *C. difficile* infection if the level of at least one BA (e.g., CA, DCA, LCA, and/or UDCA) is altered (e.g., decreased) in a sample from the mammal (e.g., a fecal sample) relative to a mammal without diarrhea. For example, a mammal can be identified as having increased susceptibility to *C. difficile* infection if the ratio of CA/DCA is increased in a sample from the mammal (e.g., a fecal sample) relative to a mammal without diarrhea.

Examples of mammals that can be treated as described herein include, without limitation, humans, monkeys, dogs, cats, cows, horses, pigs, and sheep. In some embodiments, a mammal is a human. In some embodiments, the mammal also exhibits at least one clinical biomarker of dysbiosis. Non-limiting examples of clinical biomarkers of dysbiosis include current/recent hospitalization, immune suppression, recent/current antibiotic use, and prior *C. difficile* infection.

In some embodiments, methods of treating *C. difficile* infection in a mammal described herein can be used in combination with another *C. difficile* treatment. Examples of other *C. difficile* infection treatments include, without limitation, antibiotics (e.g., metronidazole, vancomycin, and fidaxomicin), surgery (e.g., surgery to remove the diseased portion of the colon), and dietary modifications (e.g., low protein diets).

Any amount of a composition containing at least two bacteria can be administered to a mammal. The dosages of the compositions provided herein can depend on many factors including the desired results. Typically, the amount of bacteria contained within a single dose can be an amount that effectively exhibits improved gastrointestinal function within the mammal. For example, a composition containing at least two bacteria can be formulated in a dose such that a mammal receives from about $10^3$ to about $10^9$ bacteria.

The final pH of a composition containing at least two bacteria can be from about 3.5 to about 9.5 (e.g., from about 4.0 to about 9.0; from about 4.5 to about 9.0; from about 4.5 to about 8.5; from about 5.0 to about 8.5; or from about 6.5 to about 8.0). To obtain such a pH, the pH of the composition can be adjusted using a pH-adjusting agent, for example. It will be appreciated that pH adjustment can be accomplished with any of a wide variety of acids should the composition have a pH that is too high (e.g., greater than 10.0 before adjustment). Likewise, pH adjustment can be accomplished with any of a wide variety of bases should the composition have a pH that is too low (e.g., less than 3.0 before adjustment).

The invention will be further described in the following examples, which do not limit the scope of the invention described in the claims.

EXAMPLES

Example 1: *Clostridium difficile* in Microbial Dysbiosis in Patients with Diarrhea The gut microbiome of humans with diarrhea was studied by modeling these microbiomes in ex-germ-free (GF) mice, elucidated mechanisms underlying susceptibility to CDI. Specific risk factors in a subset of patients with diarrhea were identified, and it was demonstrated that alterations in their gut microbiota, when modeled in GF mice were associated with increased free amino acids, decreased short-chain fatty acids and an increased ratio of cholic acid to deoxycholic acid—all of which provide an optimal niche for pathogens such as *C. difficile*. Mice humanized with these dysbiotic communities were more susceptible to CDI, and community structure accommodated *C. difficile* expansion. Prophylactic FMT with a healthy microbial community restructured the metabolic landscape, restoring colonization resistance to *C. difficile*. Results showed that lack of colonization resistance can be an inherent phenotype of the microbiome, dictated by selective forces including those driven by host factors. This phenotype, defined with simple stool metabolic parameters, can be corrected by introducing a diverse microbial community. The ability to identify at-risk individuals using simple noninvasive metrics and restore colonization resistance through FMT represents a novel approach to the prevention of diseases like CDI, especially among hospitalized and immunocompromised patients.

Results

Figure 1:
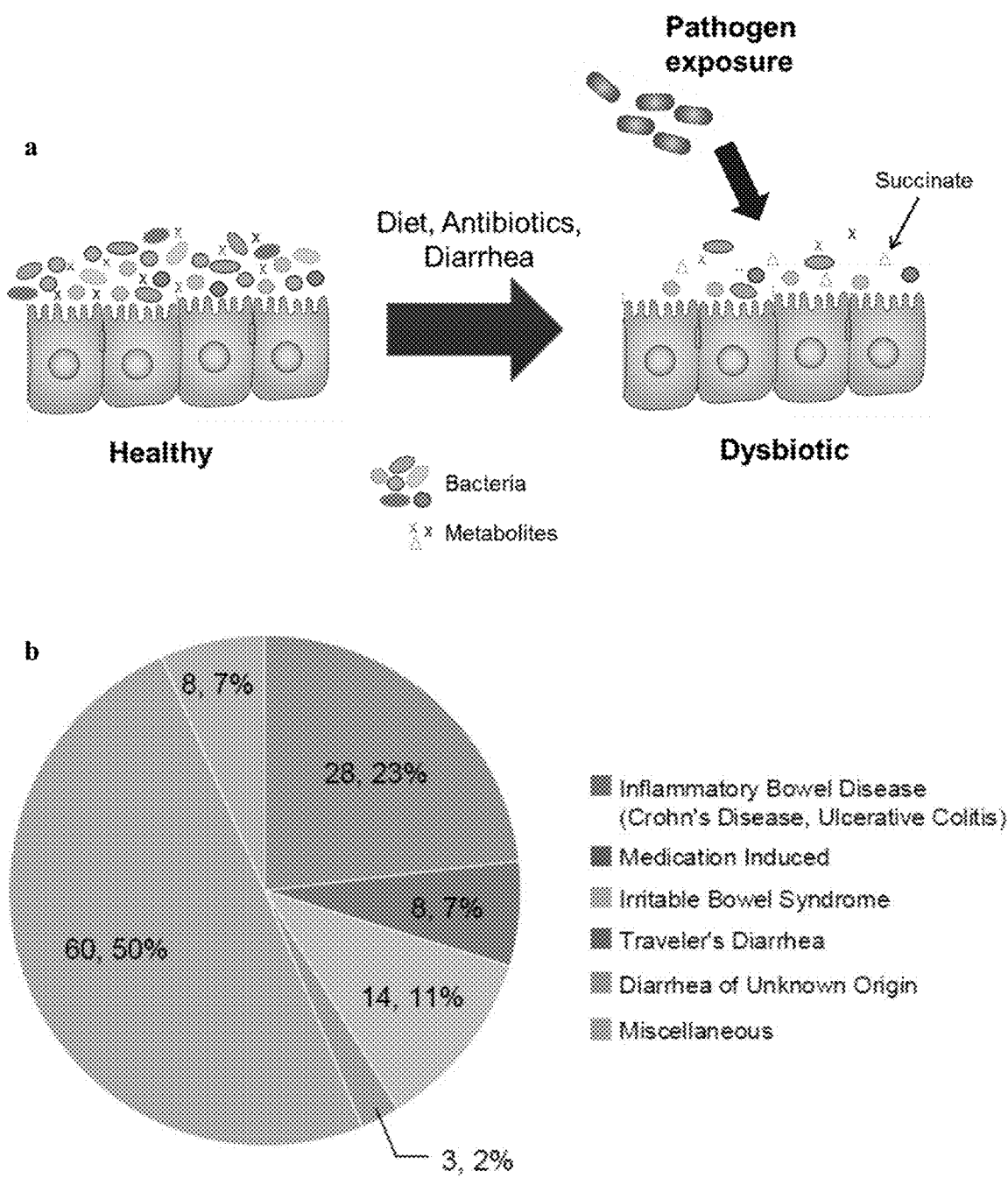
FIG. 1 shows that alterations in gut microbiota can result in diarrhea. (A) A schematic showing that alterations in gut microbiota can increase susceptibility to pathogens (adapted from Rupnik et al. 2009 *Nat Rev Microbiol.* 7:526-36; and Ferreyra et al. 2014 *Cell Host Microbe* 16:770-777). (B) Etiology of diarrhea (n=115; miscellaneous includes lactose/fructose intolerance, dysautonomia, pelvic floor dysfunction, and lymphocytic colitis).
Figure 2:
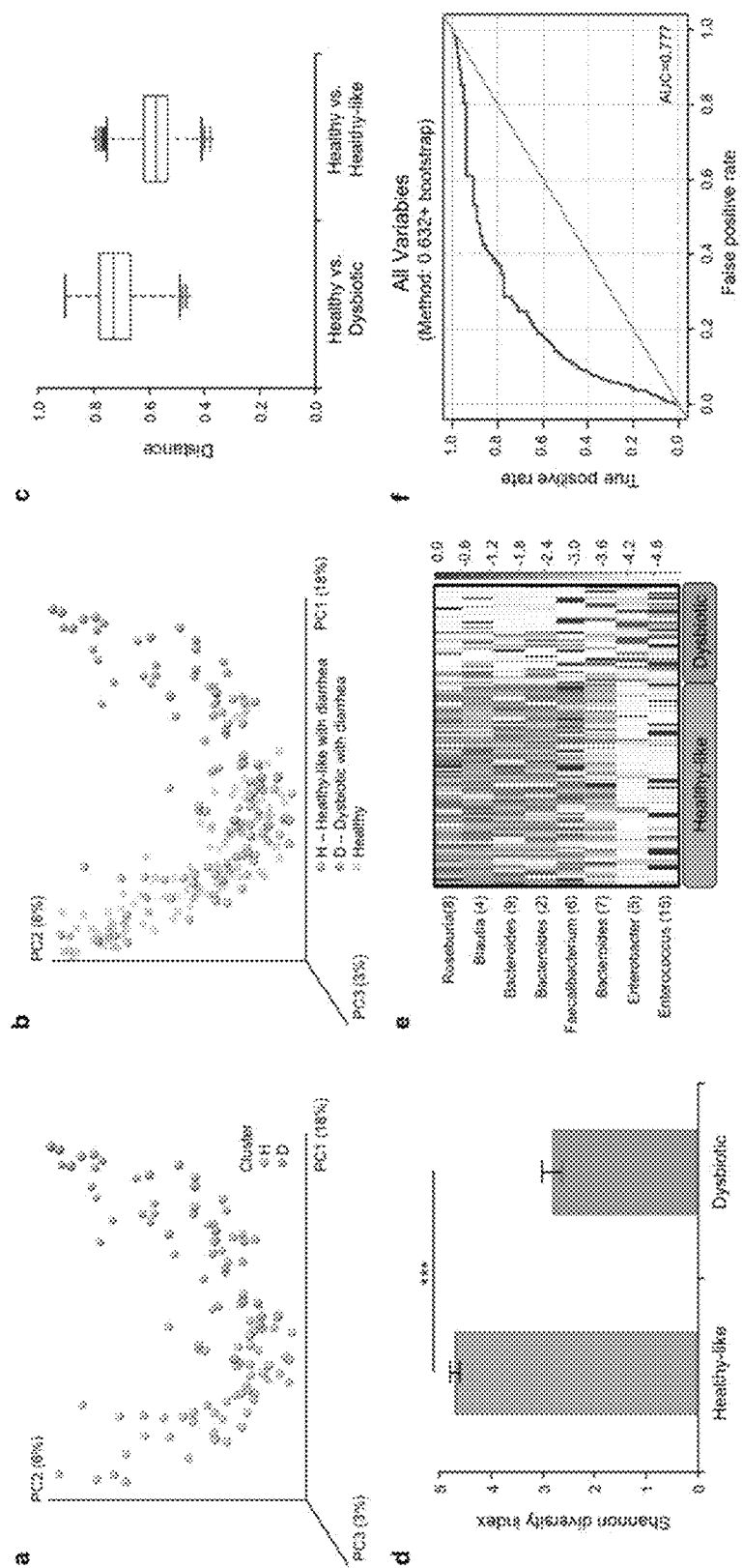
FIG. 2 shows that clinical features predict dysbiosis in a subset of patients with diarrhea. Beta-diversity (unweighted UniFrac) of (A) patients with diarrhea clustered based on PAM: Cluster H, n=78, and Cluster D, n=37 (B) patients with diarrhea and healthy controls. (C) Unweighted UniFrac distances between healthy-like and dysbiotic patients with diarrhea, and healthy controls (plotted are median with IQR and SD, Bonferroni-corrected p<0.0001, t-test). (D) Alpha-diversity of patients with dysbiotic and healthy-like microbial communities (plotted averages with SEM; t-test; ***p<0.0005, t-test). (E) Heatmap of significantly different microbial taxa between healthy-like and dysbiotic communities (OTU number is featured after genus; all Bonferroni-corrected p<0.02, Wilcoxon rank-sum test). (F) ROC curve based on 5 clinical risk factors predictive of dysbiosis: antibiotic use (odds ratio; 95% confidence interval: recent antibiotics (5.21; 2.14-12.71; p<0.001), immunosuppression (2.87; 1.27-6.48; p=0.012), current hospitalization (6.17; 2.22-17.15; p<0.001), recent hospitalization (4.87; 1.72-13.74; p=0.003), and prior *C. difficile* infection (CDI) (9.26; 2.37-36.20, p=0.001; AUC=0.777; Table 3).
Figure 3:
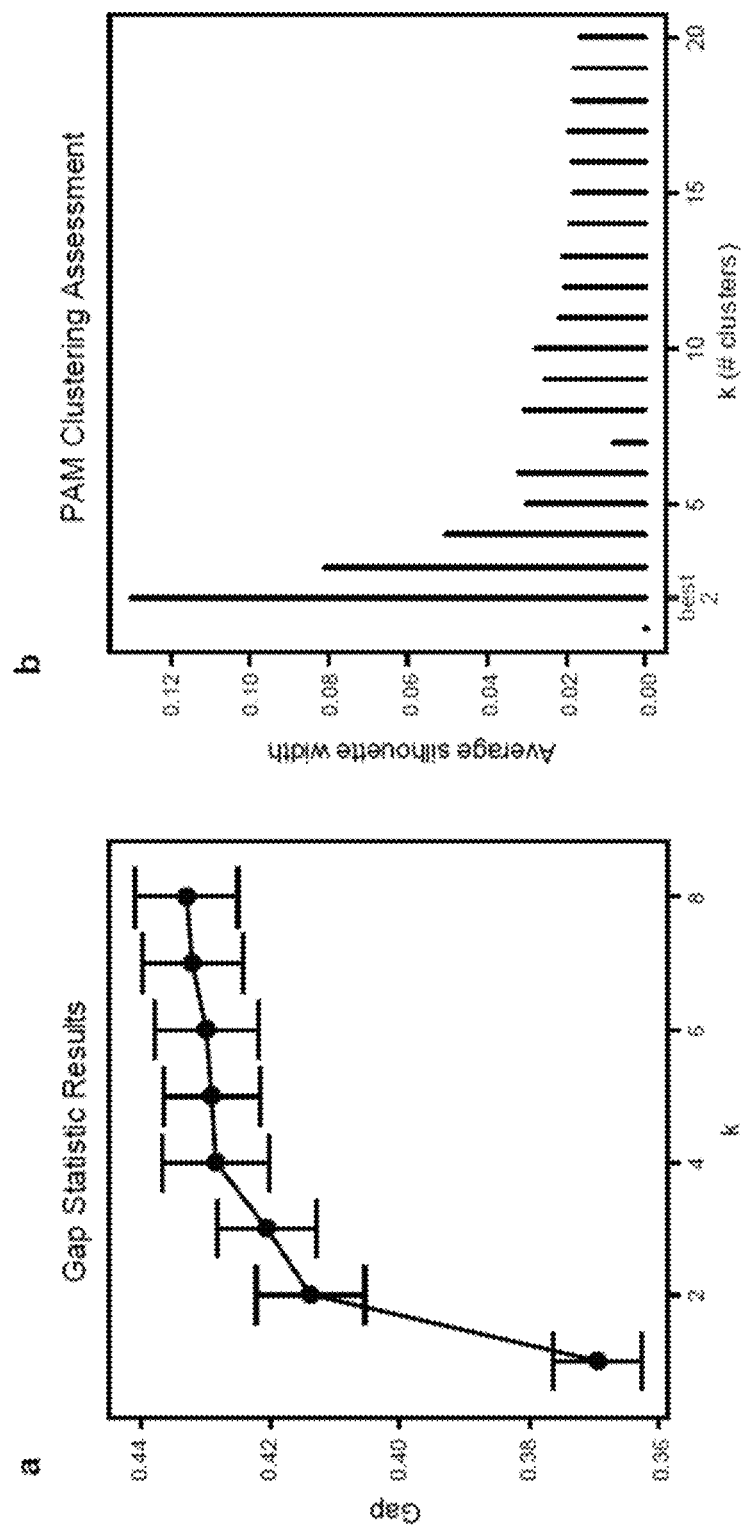
FIG. 3 shows that partitioning around medoids (PAM) identifies two clusters of patients with diarrhea based on the unweighted UniFrac distance metric. (A) The gap statistic and (B) average silhouette width were used to determine the optimal cluster number.
Figure 4:
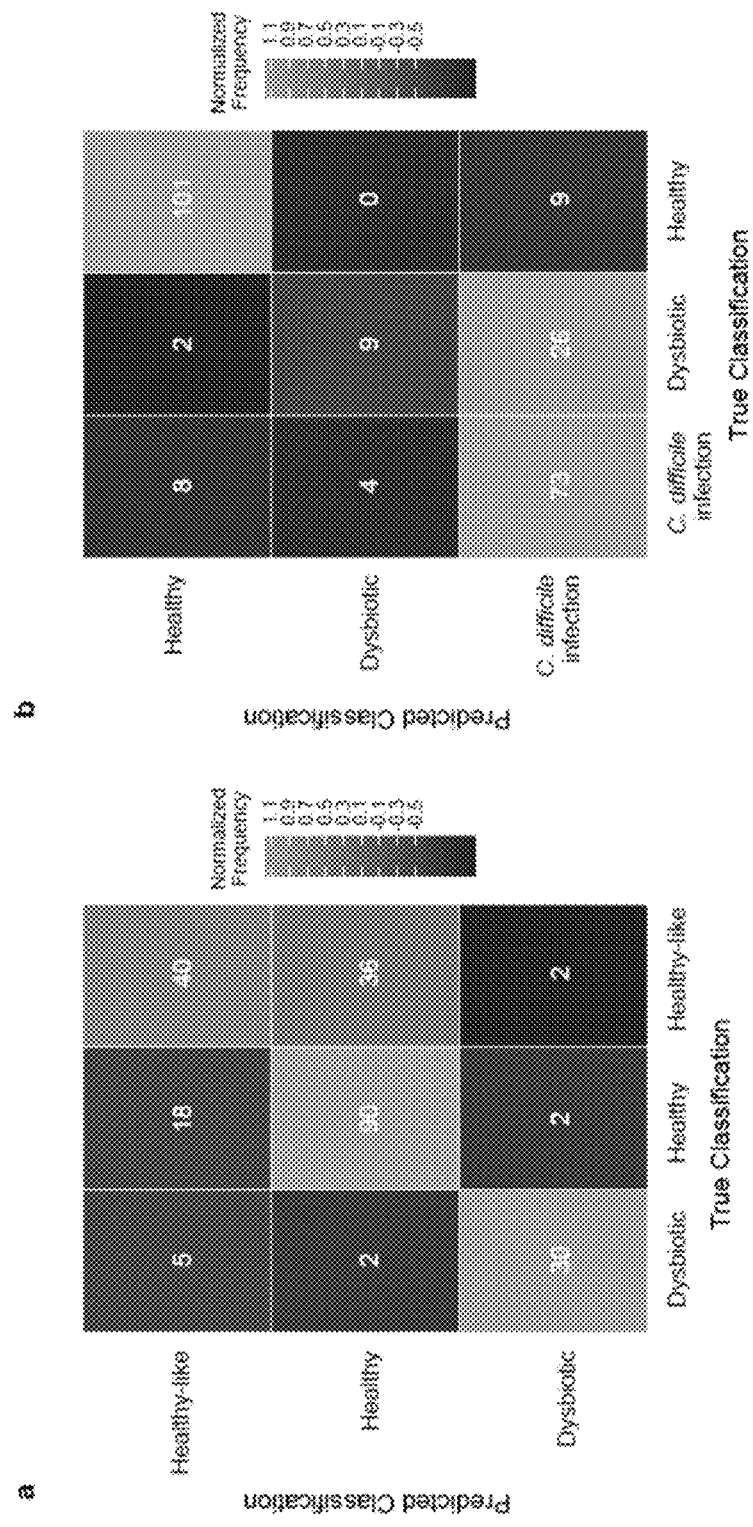
FIG. 4 shows that healthy-like microbial communities are similar to healthy controls, and dysbiotic microbial communities are similar to microbial communities in patients with *C. difficile* infection (CDI). Confusion matrix generated using Random Forests classifier based on OTUs to determine similarity of (A) healthy-like and dysbiotic microbial communities to communities from healthy controls, and (B)

To determine the effect of diarrhea on the gut microbiota, community composition was profiled using the 16S rRNA gene in 115 patients who presented with diarrhea (Table 1). All individuals tested negative for *C. difficile* and had a spectrum of underlying conditions (FIG. 1). Principal Coordinate analysis (PCoA) plots based on beta-diversity showed a wide distribution of microbial communities (FIG. 2A). Partitioning Around Medoids (PAM) clustering analysis with the gap statistic identified 2 distinct clusters as optimal (cluster H; and cluster D; Extended Data FIG. 7A, B) (Tibshirani et al. 2001, *J R Stat Soc: Ser B (Stat Methodol)* 63:411-423). Microbial communities from patients with diarrhea within cluster H grouped with the 118 healthy controls as compared to those within cluster D (FIG. 2B, C). Additionally, patients within cluster H were more likely to be misclassified as healthy controls compared to patients in cluster D based on Random Forests supervised learning algorithm using Operational Taxonomic Unit (OTU)-level abundances (FIG. 4A). Hence, patients within cluster H were referred to as healthy-like. Patients within cluster D were referred to as dysbiotic given the difference in their microbial composition from healthy controls.

TABLE 1

Demographic data of healthy controls, patients with diarrhea, and patients with *C. difficile* infection.

| | Healthy (n = 118) | Diarrhea (n = 115) | *C. difficile* Infection (n = 85) | p-value |
|---|---|---|---|---|
| Sex, n (%) | | | | |
| Male | 58 (49) | 39 (34) | 35 (41) | 0.06 |
| Female | 60 (51) | 76 (66) | 50 (59) | |
| Age (yr) | | | | |
| Mean (SD) | 49.7 (15.8) | 47.4 (12.4) | 49.3 (18.0) | 0.49 |
| Range | 25-79 | 20-64 | 20-96 | |
| BMI (SD) | 28.1 (7.5) | 28.3 (7.0) | 27.2 (6.3) | 0.55 |

The dysbiotic group was characterized by significantly decreased microbial richness and evenness (FIG. 2D), and significantly increased relative abundances of OTUs within *Enterococcus, Enterobacter,* and *Bacteroides*, and decreased *Faecalibacterium, Roseburia, Blautia* and *Bacteroides* (FIG. 2E, Table 2), when compared to the healthy-like group. Alteration in gut microbial community structure was not associated with a defined etiology of diarrhea (Table 3). To identify drivers of dysbiosis, the clinical metadata was examined and 5 discrete clinical factors were identified that predicted dysbiosis in patients with diarrhea: antibiotic use within the previous 3 weeks, immunosuppression, current hospitalization, recent hospitalization—within the previous 4 weeks, and prior *C. difficile* infection (CDI); age, gender and body mass index were not significantly associated with dysbiosis (Table 3). Patients within the dysbiotic group exhibited a significantly greater number of clinical risk factors as compared to healthy-like individuals (dysbiotic: 1.97 (1.19); healthy-like: 0.64 (0.93) risk factors per person, mean (SD), $p<10^{-8}$, Wilcoxon rank-sum test) and these risk factors were strong predictors of dysbiosis based on receiver operator characteristic (ROC) curve analysis (area under the curve (AUC)=0.777; FIG. 2F).

TABLE 2

Differences in microbial taxa read numbers between healthy-like and dysbiotic microbial communities in patients with diarrhea.

| Taxonomy | Healthy-like Mean Reads per Sample | Dysbiotic Mean Reads per Sample | Banferroni Corrected p-value |
|---|---|---|---|
| Bacteroidetes; Bacteroidia; Bacteroidales; Bacteroidaceae; Bacteroides | 1376 | 42 | p < 0.0001 |
| Firmicutes; Clostridia; Clostridiales; Lachnospiraceae; Roseburia | 1716 | 189 | p < 0.0001 |
| Firmicutes; Clostridia; Clostridiales; Ruminococcaceae; Faecalibacterium | 1417 | 39 | p < 0.0001 |
| Bacteroidetes; Bacteroidia; Bacteroidales; Bacteroidaceae; Bacteroides | 4113 | 2012 | p < 0.0001 |
| Firmicutes; Clostridia; Clostridiales; Lachnospiraceae; Blautia | 1800 | 1187 | p < 0.0001 |
| Proteobacteria; Gammaproteobacteria; Enterobacteriales; Enterobacteriaceae; Enterobacter | 115 | 5993 | 0.001 |

TABLE 2-continued

Differences in microbial taxa read numbers between healthy-like and dysbiotic microbial communities in patients with diarrhea.

| Taxonomy | Healthy-like Mean Reads per Sample | Dysbiotic Mean Reads per Sample | Banferroni Corrected p-value |
|---|---|---|---|
| Bacteroidetes; Bacteroidia; Bacteroidales; Bacteroidaceae; Bacteroides | 817 | 2373 | 0.004 |
| Firmicutes; Bacilli; Lactobacillales; Enterococcaceae; Enterococcus | 29 | 2401 | 0.016 |

TABLE 3

Risk factors that differentiate healthy-like and dysbiotic microbial communities in patients with diarrhea.

| | Risk Factors in Individuals with Diarrhea | | | | |
|---|---|---|---|---|---|
| | Healthy-like (n = 78) | Dysbiotic (n = 37) | Odds Ratio | Lower/Upper Confidence Intervals | p-value |
| Sex, n (%) | | | | | |
| Male | 28 (36) | 26 (30) | 1.32 | 0.57/3.08 | 0.515 |
| Female | 50 (64) | 11 (70) | | | |
| Age (yr) | | | | | |
| Mean (SD) | 50.7 (12.4) | 50.6 (12.8) | 1 | 0.97/1.03 | 0.956 |
| Range | 24-68 | 23-67 | | | |
| Body Mass Index (SD) | 27.4 (6.5) | 30.2 (7.8) | 1.06 | 1.00/1.12 | 0.050 |
| Recent Hospitalization, n (%) (within last 4 weeks) | 7 (9) | 12 (32) | 4.87 | 1.72/13.74 | 0.003 |
| Current Hospitalization, n (%) | 7 (9) | 14 (37) | 6.17 | 2.22/17.15 | <0.001 |
| Prior *C. difficile* infection, n (%) | 3 (4) | 10 (26) | 9.26 | 2.37/36.30 | 0.001 |
| Immune suppressed, n (%) | 21 (27) | 19 (50) | 2.87 | 1.27/6.48 | 0.012 |
| Recent antibiotics, n (%) (within last 3 weeks) | 12 (15) | 18 (47) | 5.21 | 2.14/12.71 | <0.001 |
| Etiology of Diarrhea | NA | NA | NA | NA | 0.120 |

To determine the functional consequence of dysbiosis, susceptibility of microbial communities within these 2 distinct clusters to a pathogen, *C. difficile*, which is commonly associated with microbial dysbiosis was investigated. The microbial communities were modeled in ex-germ-free (GF) mice by humanizing these mice with stool from 2 dysbiotic donors (Dysbiotic A, Dysbiotic B) and 2 healthy-like donors (Healthy-like C, Healthy-like D; FIG. 5A) as previously shown to recapture microbial composition and function (Marcobal et al. 2013 ISMS J. 7:1933-1943; Turnbaugh et al. 2009 *Sci Transl Med.* 1:6ra14). 16S rRNA gene sequencing of the fecal microbial community in ex-GF-humanized mice (4 weeks post-humanization) indicated that microbial communities clustered based on donor type, reproducing the human state (FIG. 6A, B). UniFrac distances within dysbiotic and healthy-like mouse groups were significantly shorter than distances between dysbiotic and healthy-like mice (FIG. 6C), and humanization efficiency was 86% at the family level (FIG. 12), similar to previous studies (Ridaura et al. 2013 *Sci* 341). Gut microbial communities in mice humanized from the dysbiotic donors were significantly less diverse (FIG. 7D). When mice were challenged with an overnight culture of *C. difficile* by oral gavage, the dysbiotic group had significantly higher stool *C. difficile* colony forming units (CFU) at Day 1, 2, and 6 post-challenge. The difference grew over time, differing on average by 13.9-, 262-, and >1000-fold, respectively (FIG. 7A). Additionally, significant inflammation on H&E stained sections of the proximal colon was observed in the dysbiotic group as compared to the healthy-like group (FIG. 7B, C, Table 4, FIG. 13).

TABLE 4

Mouse colon inflammation scoring rubric.

| Measure of Inflammation | Score |
|---|---|
| Inflammation in the lamina propria | 0 = none |
| | 1 = focal, minimal |
| | 2 = focal, marked |
| | 3 = diffuse, marked |
| Maximum polymorphonuclear cells (neutrophils) in high power field | 0 = none |
| | 1 = 5-10 |
| | 2 = 10-20 |
| | 3 = 20-30 |
| | 4 = >30 |
| Depth of inflammation | 0 = lamina propria only |
| | 1 = superficial submucosa |
| | 2 = deep submucosa |
| | 3 = transmural |
| Total | 0-10 |

To investigate if susceptibility to *C. difficile* represented an inherent feature of the community, the gut microbial community structure in humanized mice pre- and 2 days post-*C. difficile* challenge in the dysbiotic and healthy-like humanized mice was compared. UniFrac distances within the microbial communities post-*C. difficile* challenge were not significantly different from the distances between the microbial communities pre- and post-*C. difficile* challenge (FIG. 6E) suggesting that susceptibility is an inherent feature of the community rather than a result of *C. difficile*- related perturbation. To examine whether this could be extrapolated to human subjects, the microbial communities of dysbiotic patients and a cohort of patients with CDI (FIG. 7D) was examined. Interestingly, it was found that microbial communities of patients within the dysbiotic group were significantly closer to communities in patients with CDI as compared to healthy controls (FIG. 7E) and more likely to be misclassified as CDI as opposed to healthy controls based on Random Forests supervised learning algorithm (FIG. 9B).

To determine the microbial community phenotype responsible for susceptibility to CDI, the functional capacity of the humanized mouse communities at the transcriptional and metabolic level was assessed. Whole community gene expression using RNAseq on stool from dysbiotic and healthy-like humanized mice was assessed. Pathway analysis using HUMAnN2 (Abubucker et al. 2012 *PLoS Comput Biol* 8:e1002358) followed by a Jaccard similarity calculation showed that microbial community function within dysbiotic mice was significantly closer to their dysbiotic donor than to the healthy-like humanized mice or healthy-like donor and vice versa (FIG. 8A). Differential expression analysis indicated that there were significant differences in 306 pathways between the 2 groups of humanized mice pre-*C. difficile* challenge (FIG. 8B, FIG. 14, and FIG. 15). The healthy-like communities had increased expression of short chain fatty acid (SCFA) biosynthesis pathways including butyrate, propionate, and acetate generated from L-glutamate as a precursor, and secondary bile acid (BA) biosynthesis systems (FIG. 9A). A significant increase in the expression of carbohydrate utilization systems including arabinose, glucose, sucrose, and fucose was also observed in healthy-like communities (FIG. 15). To determine if there was a shift in community functionality following *C. difficile* challenge, global gene expression profiles 2 days post-*C. difficile* challenge were compared and differences in 281 pathways were found that included a majority of the same pathways seen prior to *C. difficile* challenge, suggesting gene expression, like composition, is a stable community feature conducive to pathogen invasion (FIG. 8C, FIG. 16, and FIG. 17).

The functional relevance of transcriptional differences was assessed using metabolomics in stool samples collected from humanized mice before *C. difficile* challenge. There were significant differences in 269 metabolites detected using UPLC-MS untargeted metabolomics, which included differential levels of BAs, SCFAs, and amino acids (AAs) (FIG. 10A, B, FIG. 18, and FIG. 19). A targeted UPLC-MS panel indicated that dysbiotic communities had significantly reduced secondary BAs, deoxycholic acid (DCA), lithocholic acid (LCA), taurodeoxycholic acid (TDCA), and ursodeoxycholic acid (UDCA), and significantly more primary BA taurocholic acid (TA) (FIG. 9B). Dysbiotic mice also displayed a >500-fold increase in the predominant primary/secondary BA (cholic acid (CA)/DCA ratio), indicating a bias toward primary BAs (FIG. 9C). A GC-MS targeted panel revealed significantly lower levels of SCFAs including propionate, acetate, butyrate, valerate, and hexanoate in the dysbiotic mice (FIG. 9D). $^1$H-NMR of fecal pellet extracts showed higher free AAs in the dysbiotic community (FIG. 8D). The significance of AAs in supporting expansion of *C. difficile* in the dysbiotic community was evident by a concentration-dependent increase in *C. difficile* growth seen with increase in AA concentration in defined medium either lacking or containing low concentrations of DCA (FIG. 8E). Growth was completely inhibited at high concentrations of DCA irrespective of AA concentration, reflective of the metabolic milieu in the healthy-like community (FIG. 8E). In order to determine if specific AAs provided a selective advantage for *C. difficile*, we examined the role of proline, which showed the greatest difference in concentration between the healthy-like and dysbiotic community (4.8 fold; FIG. 9E), and is known to support *C. difficile* growth via Strickland fermentation (Bouillaut et al. 2015 *Res Microbiol.* 166:375-383; Bouillaut et al. 2013 *J Bacteriol.* 195:844-854; Jackson et al. 2006 *J Bacteriol.* 188:8487-8495). Proline reductase expression as a marker for proline utilization in whole community RNAseq data was assessed. Humanized mice with a dysbiotic community had lower expression of proline reductase A (prdA) and E (prdE) compared to humanized mice with a healthy-like community (FIG. 9F), corresponding to the increased level of fecal proline seen in these mice (FIG. 9E). Expression of prdA and prdE in dysbiotic mice post-*C. difficile* challenge was attributed entirely to *C. difficile* supporting the role of proline in expansion of *C. difficile*. In contrast, in healthy-like mice, prdA and prdE expression was attributed primarily to *C. hylemonae, Dorea longicatena*, and *Lachnospiraceae bacterium* 5_1_57FAA (FIG. 9G). Further supporting the role of proline, *C. difficile* was unable to grow in the absence of proline (FIG. 9H). Using patient derived microbial communities, we validate previous studies that demonstrate the inhibitory effect of secondary BAs on *C. difficile* growth (Buffie et al. 2015 *Nature* 517:205-208; Sorg et al. 2010 *J Bacteria* 192:4983-4990; Sorg et al. 2008 *J Bacteriol.* 190: 2505-2512; Sorg et al. 2009 *J Bacteriol.* 191:1115-1117) and further suggest a role for AA availability, specifically proline, in facilitating *C. difficile* expansion by providing a favorable nutritional niche. To further evaluate the role of proline availability in vivo, GF mice were administered a custom diet either with or without proline prior to humanization with dysbiotic communities. Animals that received a proline deficient diet showed a 4.99 fold decrease in colonization at Day 1 post infection (FIG. 9I). This suggests proline availability is relevant for early emergence and establishing infection.

FMT was successful in treating recurrent CDI in 80-95% of patients and has been shown to increase SCFA and secondary BA concentrations in the gut (van Nood et al. 2013 *N Engl J Med* 368:407-415; Lawley et al. 2012 *PLoS Pathog.* 8; Weingarden et al. 2014 *Am J Physiol Gastrointest Liver Physiol.* 306:G310-319). It was predicted that the significant metabolic alterations in the dysbiotic community described above could be restored using a prophylactic transfer of a healthy microbial community to re-establish colonization resistance. To test this, a mouse-adapted, healthy human-derived FMT community was delivered to ex-GF mice 4 weeks after being humanized with dysbiotic microbial communities (FIG. 5B). 16S rRNA community analysis revealed a significant shift in the gut microbial communities of dysbiotic mice to resemble the donor microbial community after FMT (FIG. 11A, B). There was also a significant increase in alpha-diversity following transplantation in dysbiotic mice (FIG. 11C).

There was no detectable *C. difficile* in stool on day 1, 2, or 6 following *C. difficile* challenge and no significant inflammation on H&E-stained sections from the proximal colon (FIG. 11D). Metabolically, a significant increase in stool secondary BAs (DCA, LCA and UDCA) and decrease in primary BA (TA) (FIG. 11E) was observed. Concentrations of the SCFAs butyrate, acetate, propionate, and valerate also significantly increased after FMT (FIG. 11F). Proline concentrations decreased significantly after FMT (FIG. 11G) and many free AAs showed a similar trend (FIG. 10C).

These results suggested that preemptive FMT from a healthy individual can restore colonization resistance in mice with dysbiotic communities by restoring the metabolic milieu and eliminating open niches for *C. difficile*.

Methods

Human Study. All human studies were approved by the Mayo Clinic Institutional Review Board. Adults (>18 years old) who presented with diarrhea and tested negative for *Clostridium difficile* (n=115; IRB #12-007176), and those who tested positive for *C. difficile* via PCR (Sloan et al. 2008 *J Clin Microbiol* 46:1996-2001; n=95; IRB #12-000554) were voluntarily enrolled. Upon receiving consent from participants, frozen stool left over from clinical testing was obtained and stored at −80° C. until DNA extraction. Participants were recruited at Mayo Clinic in Rochester, Minnesota. The healthy control group (n=118) was comprised of volunteers who provided stool samples to the Midwest Reference Range Biobank (Chen et al. 2016 *PeerJ* 4:e1514; IRB #13-003694).

Bacterial Strains and Growth Conditions. All strains for this study were maintained inside an anaerobic growth chamber with a gas mixture of 75% $N_2$/20% $CO_2$/5% $H_2$ (Coy Lab Products, Grass Lake, MI). Liquid and solid growth media was allowed to reduce in the anaerobic chamber for a minimum of 24 hours prior to use. For transfer out of the chamber, liquid stocks were sealed in sterile, gas-tight crimp cap glass vials. *C. difficile* strain 630 was maintained at 37° C. on *Clostridium difficile* Moxalactam Norfloxacin (CDMN) blood agar plates (Aspinall et al. 1992 *J Clin Pathol.* 45:812-814), in Reinforced Clostridial Medium (RCM) broth (Difco DF1808173), or in Basal Defined Medium (BDM) (Karasawa et al. 1995 *Microbiology.* 141:371-375) broth. *C. difficile* amino acid (AA) utilization was assessed using modified BDM containing ½ or ¼ of the standard AA content. Proline utilization was assessed in modified BDM lacking glucose and proline. Bacterial growth rates were assessed using a BioTek Eon microplate spectrophotometer (BioTek, Winooski, VT).

Oral Gavage Preparation and Delivery. Fecal suspensions from human or mouse samples were prepared by combining equal volumes of stool (human) with sterile pre-reduced phosphate buffered saline (PBS) or 6 pellets (mouse) with 600 µl of PBS in a 10 mL conical vial inside an anaerobic chamber. The vials were sealed, removed from the chamber, vortexed for 5 minutes at room temperature, allowed to settle at 4° C. for up to 2 hours, and transferred into the gnotobiotic isolators. Mice were gavaged with 300 µl of the fecal suspension as described previously (Reigstad et al. 2015 *FASEB J.* 29:1395-1403).

Mouse Husbandry. Mouse experiments were performed with germ-free (GF) Swiss Webster mice born and maintained in the Mayo Clinic Germ Free Facility as described previously (Reigstad et al. 2015 *FASEB J.* 29:1395-1403). Where appropriate, animals were switched to a defined diet (OpenStandard Diet A11112201, Research Diets, New Brunswick, NJ) with and a variation deficient in proline (Research Diets, New Brunswick, NJ). All mouse experiments complied with Institutional Animal Care and Use Committee guidelines (IACUC protocol #A32015).

Mouse Experiments. Human community *C. difficile* susceptibility was assessed using sex matched, GF mice. Experiment sample sizes were chosen based on similar prior studies (Turnbaugh et al. 2009 *Sci Transl Med.* 1:6ra14; Backhed et al. 2007 *Proc Natl Acad Sci USA* 104:979-984; Ridaura et al. 2013 *Science* 341:1241214) and logistical constraints within gnotobiotic isolators. Littermates were used when possible to minimize contamination risks associated with multiple GF transfers, however formal randomization was not employed. GF animal technicians performed mouse allocation and investigators were blinded to selection. Mice were humanized using fecal suspensions prepared from 2 patients in the human "dysbiotic" group: dysbiotic donor A (2 risk factors—prior *C. difficile* infection (CDI) and immune suppressed) and dysbiotic donor B (3 risk factors— recent antibiotics, recent hospitalization, immune suppressed); and 2 patients in the human "healthy-like" group: healthy-like donor C (no risk factors) and healthy-like donor D (no risk factors). A total of 21 4-week old mice were humanized with either dysbiotic A stool (n=4), dysbiotic B stool (n=6), healthy-like C stool (n=5) or healthy-like D stool (n=6) (FIG. 5A). Mice humanized from the same human sample were co-housed in covered cages (separated by sex), and mice humanized with like communities (dysbiotic or healthy-like) were co-housed in the same isolator.

Human-derived communities were allowed 4 weeks to adapt to the mouse gut; then, the mice were challenged by oral gavage with 300 µl of overnight liquid culture growth of *C. difficile* strain 630. Fecal pellets were collected pre- and at day 1, day 2, and day 6 post-challenge for *C. difficile* colony counts, 16S rRNA community analysis, and metabolomics (FIG. 5A). Mice were euthanized on day 7 and proximal colon tissue samples were collected at necropsy. Colon contents were removed and the tissue was rinsed with Krebs Mannitol (115 mM NaCl, 2 mM $KH_2PO_4$, 2.4 mM $MgCl_2*6H_2O$, 25 mM $NaHCO_3$, 8 mM KCl, 1.3 mM $CaCl_2$, 250 mM Mannitol). A 5 mm by 5 mm section of proximal colon tissue was stored in 10% formalin for paraffin embedding and hematoxylin and eosin (H&E) staining.

The ability of dietary intervention to restore colonization resistance was assessed using custom diets as described above. GF animals were switched to the custom chow (proline$^+$ n=5, proline$^-$ n=5) and humanized with dysbiotic stool. After a 4 week adaptation period, animals were challenged with *C. difficile* and pellets collected at Day 1 post infection for *C. difficile* colony counts.

The ability of prophylactic FMT to confer resistance to susceptible communities was also assessed in the GF Mouse model (FIG. 5B). Fecal suspensions were generated by suspending frozen mouse pellets collected 4 weeks after humanization from mice humanized with dysbiotic A or dysbiotic B stool from the *C. difficile* susceptibility experiment described above. A total of 6 4-week old mice received fecal suspensions via oral gavage from dysbiotic A (n=3) or dysbiotic B (n=3) and were housed as described above.

Four weeks after colonization, mice were given 2 FMTs 4 days apart. FMTs were prepared by combining 6 freshly collected mouse pellets from mice previously humanized with stool from a healthy human donor mixed with pre-reduced 1×PBS. 300 µl of the suspension was administered to each mouse via oral gavage. One week after the FMTs, the mice were challenged with *C. difficile* as described above. Fecal pellets were collected from the mice pre-FMT, post-FMT, and on day 1, day 2, and day 6 post-*C. difficile* challenge for *C. difficile* colony counts, 16S community analysis, and metabolomics. Mice were euthanized on day 7 post-*C. difficile* challenge and colon tissue samples were collected at necropsy as described above.

*C. difficile* stool quantification. One pellet was used to quantify *C difficile* stool burden at day 1, 2, and 6 post-*C. difficile* challenge. A 1 µL aliquot of each fecal pellet was serially diluted in duplicate, spotted onto pre-reduced CDMN agar media and incubated anaerobically at 37° C. for 24 hours. Identifiable *C. difficile* colonies were counted and CFU/mL of stool calculated. 2-way ANOVA in SAS 9.3 was used to compare *C. difficile* concentrations across treatment groups and days.

Colon pathology and analyses. Formalin-preserved paraffin-embedded colon tissue was submitted for sectioning, slide preparation, and H&E staining (Mayo Clinic, Phoenix, Arizona). A pathologist who was blinded to mouse IDs and treatment groups reviewed slides and colon inflammation was graded on number of polymorphonuclear cells (PMN) per high power field (HPF) (score of 0-4), presence of inflammatory cells in the lamina propria (score of 0-3), and tissue layer depth of inflammatory cells (score of 0-3) (Table 2, Table 3). To compare inflammation scores between the dysbiotic and healthy-like groups, a linear mixed effects model (LME) was fit to the data using R-3.1.2 with a random intercept for the donor type to account for within-donor correlation.

16S Extraction, sequencing, and analysis. DNA was extracted from human stool samples (0.25 g stool per extraction) and mouse pellets (1 pellet per extraction) using a MoBio PowerSoil Kit (MoBio Laboratories, Carlsbad, CA, USA). The V4 region (515F, 806R) of the 16S rRNA gene was amplified and sequenced using an Illumina MiSeq (Illumina, San Diego, CA) at the Mayo Clinic Medical Genome Facility (Mayo Clinic, Rochester, MN). Demultiplexing and quality filtering was performed in QIIME 1.9.1. Operational taxonomic unit (OTU) clustering at 97% sequence similarity and taxonomic assignment was performed with UCLUST, RDP classifier, and Greengenes (DeSantis et al. 2006). OTUs were picked closed-reference and de novo. A total of 10 human subjects (8 healthy, 2 diarrhea) were excluded from 16S rRNA analyses due to low reads or failing to pass quality thresholds during sequencing. Human samples were rarified at 8,000 reads. Mouse samples from the first experiment testing *C. difficile* susceptibility were rarefied at 15,000 reads. Mouse samples from the second experiment testing prophylactic FMT were rarefied at 15,000 reads.

Data analyses were performed in QIIME 1.9.1, R-3.1.2, and SAS 9.3. Partitioning around medoids (PAM) clustering performed in R-3.1.2 was used to define clusters in human patient samples. Optimal cluster number was determined by gap statistic and confirmed by ASW (average silhouette width) statistic based on unweighted UniFrac distances (Tibshirani et al. 2001 *J Roy Stat Soc* B 63:411-423; Rousseeuw et al. 1987 *J Comput Appl Math* 20:53-65). A univariable logistic regression model was used to calculate the odds ratio and the significance of individual clinical risk factors. ROC curve was constructed using 0.632+ bootstrap method based (Efron et al. 1997 *J Am Stat Assoc* 92:548-560) on a multivariable logistic regression model. Cluster analysis, logistic regression, and ROC analysis were performed in R-3.1.2. Shannon diversity indices (assessing microbial abundance and evenness) were calculated in QIIME and compared using t-tests in Microsoft Excel. Relative abundances of microbial taxa were compared between groups using Kruskal-Wallis (group_significance.py in QIIME), LEfSe (Segata et al. 2011 *Genome Biol* 12:R60-R60; which incorporates the Wilcoxon rank-sum test), and the Boruta algorithm (Kursa et al. 2010 *J Stat Softw* 36:1-13). Random Forests (supervised_learning.py) and distance analyses (make_distance_boxplots.py) were also run in QIIME to classify and determine similarities between groups.

RNA isolation. Fecal pellets collected for RNA extraction were transferred into tubes containing 6041 of pre-chilled (−20° C.) RNAlater-ice (Life Technologies, Carlsbad, CA) and incubated at −20° C. for 24 hours. Samples were then centrifuged at 14,000 g at 4° C. in an Eppendorf 5810R centrifuge (Eppendorf, Germany) for 5 minutes, the RNAlater-ice containing supernatant removed, and 500 µl of Buffer A (200 mM NaCl, 20 mM EDTA), 210 µl of 20% SDS, 500 µl of acidified phenol:chloroform (125:24:1, pH 4.5) and sterile glass beads (MoBio 13118-50, Carlsbad, CA) were added to each tube. The samples were homogenized by bead beating using a MP Bio Fast Prep 24 (MP Biomedicals, Santa Ana, CA) using 6.0 m/s pulses for 60 seconds, and then centrifuged at 14,000 g at 4° C. for 5 minutes. The aqueous phase was removed to a clean tube and extracted a second time with 500 µl of phenol:chloroform (125:25:1, pH 4.5). The samples were centrifuged at 14,000 g at 4° C. for 5 minutes, the aqueous phase removed into a clean 1.5 mL microcentrifuge tube and combined with 60 µl of 3M sodium acetate and 600 µl of −20° C. 100% ethanol. Samples were mixed by inversion and allowed to incubate on dry ice for 10 minutes, wet ice for 10 minutes, and centrifuged at 14,000 g at 4° C. for 5 minutes. The supernatant was removed and the nucleic acid containing pellet washed with −20° C. 100% ethanol and centrifuged at 14,000 g at 4° C. for 5 minutes. The ethanol wash was removed, the pellet allowed to air dry for 10 minutes, and resuspended in 100 µL of nuclease free water. After complete resuspension, 350 µL of Buffer RLT+10 µl/mL BME was added and the sample processed with a RNeasy Mini Kit (Qiagen, Valencia, CA) and contaminating DNA was removed using 2 on-column DNase treatment steps. Samples were eluted in 50 µL of nuclease free water. Total RNA yield and quality were assessed using RNA Screen Tape (Agilent, Santa Clara, CA) and an Agilent 2200 TapeStation (Agilent, Santa Clara, CA). Contaminating ribosomal RNA (rRNA) was removed using a RiboZero rRNA Removal Kit (Epicentre, Madison, WI). Depletion was confirmed using RNA Screen Tape and 2200 Tape Station before submitting samples for library preparation.

RNAseq. mRNA enriched samples were submitted to the Mayo Clinic Next Generation Sequencing Core for Library Preparation and sequencing. Library Preparation was completed using the NEB directional Library Preparation Kit (New England Biolabs, Ipswich, MA) and the samples were sequenced with an Illumina HiSeq 2500 Rapid Run with paired 101 bp reads (Illumina, San Diego, CA). The resulting sequence data was stripped of adapters and quality filtered using Trimmomatic v. 0.32 (Bolger et al. 2014 *Bioinformatics* 30:2114-2120) with parameters "ILLUMINACLIP:Adapters.fasta:2:30:10 LEADING:3 TRAILING:3 MAXINFO:75:0.1 MINLEN:75". Gene and pathway expression profiles with taxonomic identifiers when appropriate were obtained using HUMAnN2 v. 0.5.0 (Abubucker et al. 2012 *PLoS Comput Biol* 8:e1002358) and Jaccard Similarity analysis. Differential expression analysis was performed using DESeq2 v. 1.8.2 (Love et al. 2014 *Genome Biol* 15:550), with a p-value cutoff of $p<0.05$.

Untargeted Metabolomics. Metabolomics samples were extracted by bead beating with acid-washed 0.1 µm Zirconia beads in acidified water (0.01% formic acid) and acetonitrile, centrifuged at 9,000 rcf, filtered (0.22 µm) and resuspended in 5% formic acid/5% acetonitrile in water. Samples were maintained at 4° C. while extracting and stored at −80° C. The samples were analyzed by reverse-phase chromatography on a Dionex Ultimate 3000 HPLC (Dionex, Sunnyvale, CA) using a 150 µm ID nanospray column that was packed with 3 µm 2A C18 beads (ProntoSIL, MAC-MOD, Chadds Ford, PA) to ~150 mm. Injection volumes were 2 µL and samples were maintained at 7° C. while in the autosampler awaiting injection. The mobile phase buffer A was 0.2% FA, 5% DMSO in water. The mobile phase buffer B was 0.2% FA, 5% DMSO in acetonitrile. A constant flow rate of 0.4 mL/minute was delivered throughout the following 35 minute gradient (percentages indicate buffer B concentration): 0-3 minutes, 3%; 3-21 minutes, 3-95%; 24-25 minutes, 95-3%%; 25-35 minutes, 3%; 50-51 minutes, 97-3%; 51-55 minutes, 3%. A coupled Thermo Orbitrap Velos mass spectrometer (Thermo Fisher, Waltham, MA) was used to collect MS data in positive ion mode (MS1 parameters: mass range: 95-1000 m/z, 60,000 R; MS2 parameters: Top 5, data-dependent mode, no charge-state exclusion, exclusion duration 15 seconds). Peak data were processed by first applying non-linear alignment using XCMS (Smith et al. 2006 *Anal Chem* 78:779-787) and log 2 normalization. PCoA analyses were performed on these aligned and normalized data and a volcano plot was constructed by using log 2 peak fold-change and p-values calculated with Kruskal-Wallis H-tests.

Stool SCFA Quantification. Stool samples (~1.8-20 mg) were extracted for SCFAs by mixing frozen feces with acidified water (pH 2.3 with HCl) containing 6 μg/mL of an internal standard, sodium butyrate-($^{13}C$)$_4$, in a ratio of 50 μL water per mg fecal mass. Samples were vortexed for 10 minutes, sonicated for 10 minutes, and vortexed for an additional 10 minutes, and then centrifuged at 17,200 g for 10 minutes at 4° C. Supernatant from extracted samples were stored at −80° C. prior to analysis by GC-MS.

The samples were analyzed using a Trace GC 1310 coupled to a Thermo ISQ-LT (Thermo Fisher, Waltham, MA) scanning from m/z 30-300 at a rate of 5 scans/second in electron impact mode. Samples were injected at a 5:1 split ratio, and the inlet was held at 250° C. and transfer line was held at 230° C. Separation was achieved on a 30 m TG-WAXMS column (Thermo Scientific, 0.25 mm ID, 0.25 μm film thickness) using a temperature program of 100° C. for 1 minute, ramped at 20° C. per minute to 240° C. and held at 240° C. for 2 minutes. Helium carrier flow was held at 1.2 mL per minute. Amounts of acetate, proprionate, butyrate, isobutyrate, isovalerate, valerate, caproate, and heptanoate in stool samples were determined. A mix of all analytes across a range of concentrations, also containing the labeled internal standards present in the extracts, was examined during fecal extract analysis to create a calibration curve and absolute quantitation. Analyte peak areas were normalized to the internal standard peak areas using the following equation: normalized analyte response=analyte peak area* (internal standard concentration/internal standard peak area).

Stool BA Quantification. LC-MS was performed on a Waters Acquity UPLC coupled to a Waters Xevo TQ-S triple quadrupole mass spectrometer (Waters, Milford, MA). Chromatographic separations were carried out on a Waters HSS T3 stationary phase (1×100 mm, 1.8 μM). Mobile phases were methanol (B) and water with 0.1% formic acid and 2 mM ammonium hydroxide (A). The analytical gradient was as follows: time=0 minute, 0.1% B; time=0.5 minute, 0.1% B; time=2 minutes, 30% B; time=15 minutes, 97% B; time=16 minutes, 97% B; time 16.5 minutes, 0.1% B; time 21 minutes, 0.1% B. Flow rate was 210 μL/min and injection volume was 5 μL. Samples were held at 4° C. in the autosampler, and the column was operated at 70° C.

The MS was operated in selected reaction monitoring (SRM) mode, where a parent ion is selected by the first quadrupole, fragmented in the collision cell, then a fragment ion selected for by the third quadrupole. Product ions, collision energies, and cone voltages were optimized for each analyte by direct injection of individual synthetic standards. Inter-channel delay was set to 3 ms. The MS was operated in both negative and positive ionization modes with the capillary voltage set to 2.1 and 3.2 kV respectively. Source temperature was 150° C. and desolvation temperature 500° C. Desolvation gas flow was 1000 L/hour, cone gas flow was 150 L/h, and collision gas flow was 0.2 mL/min. Nebuliser pressure was set to 7 Bar. Argon was used as the collision gas, otherwise nitrogen was used.

Fecal samples were extracted as described previously (Humbert et al. 2012 *J Chromatogr B Analyt Technol Biomed Life Sci* 899:135-145) with minor modifications. In short, 70 μL of 0.1 M NaOH containing internal standards at 4 μg/mL was added for every 2 mg of feces (the range of sample weights was 2-3 mg). Samples were vortexed to mix, sonicated 10 minutes, then incubated at 60° C. for 1 hour. Samples were diluted 3-fold into water, then sonicated for 10 minutes, then vortexed for 10 minutes, then frozen at −80° C. overnight. After thawing, samples were centrifuged for 20 minutes at 4° C. at 16,000×g, then the supernatant analyzed by LC-MS. A 9-point calibration curve was prepared in similar fashion.

Peak integration was performed using Waters TargetLynx software (Waters, Milford, MA). Absolute concentration calculations were performed in Excel, and based on a 5-point minimum calibration curve. For quantitation, a signal to noise greater than 10 was required. For detection, a signal to noise greater than 3 was required.

Stool AA Quantification. $H^1$-NMR analysis was performed on aqueous stool extracts to quantitate free AA concentrations. Pellets mass was determined before resuspending in 1 mL of molecular grade water, and subjected to 3 rounds of freeze-thaw cycles using dry ice. Glass beads (MoBio 13118-50, Carlsbad, CA) were added to the tubes and the samples bead beaten using a MP Bio Fast Prep 24 (MP Biomedicals, Santa Ana, CA) for 60 seconds with 6.0 m/second pulses. Large particulate matter and the glass beads were pelleted by centrifugation at 14,000 g for 10 minutes at 4° C. The resulting supernatant was removed and stored at −80° C. prior to analysis.

Stool extract samples were thawed at room temperature for 10-15 minutes. Then 300 μl of 0.1 M phosphate buffer ($K_2HPO_4$/$KH_2PO_4$, pH 7.4) and 50 μl of 1 mM TSP-$d_4$ solution (Sigma 269913, St. Louis, MO) in $D_2O$ (Sigma 613444, St. Louis, MO) are added. Samples are shaken by vortex for 20 seconds and spun down at 13,300 rpm for 5 min. Supernatants are transferred to 5 mm NMR tubes stored at 4° C. prior to NMR measurements. The NMR analysis was performed on a Bruker AVANCE III 600 MHz instrument (Bruker, Billerica, MA) equipped with BBI probe head and SampleJet autosampler. $^1$H-NMR spectra were recorded using 1D NOESY pulse sequence with presaturation (noesygpprld) under following conditions: 90 degree pulse for excitation, acquisition time 3.89 seconds, relaxation delay 5 seconds. All spectra were acquired with 256 scans at room temperature (298K), with 64 k data points and 8417 Hz (14 ppm) spectral width. The recorded $^1$H-NMR spectra were phase corrected using Bruker TopSpin 3.5 (Bruker, Billerica, MA). Then the spectra were processed using Chenomx NMR Suite 8.1 (Chenomx, Edmonton, AB). The compounds were identified by comparing spectra to database Chenomx 600 MHz Version 10 and using available literature data (Saric et al. 2008 *PLoS Negl Trop Dis.* 2:e254; Wu et al. 2010 Analyst. 135:1023-1030; Zhao et al. 2013 *J Proteome Res.* 12:2987-2999). Quantification was based on internal standard peak integration (TSP-$d_4$). For statistical analysis the NMR spectral region from 0.6 to 9 ppm was divided in 0.04 ppm wide bins (solvent region 4.6-5.2 ppm was excluded). The bins were normalized using total peak area normalization, and standardized peak area (TSP-d4) normalization.

These results demonstrate that a subset of patients with diarrhea have gut microbial communities distinct from healthy controls. Dysbiotic gut microbial communities were characterized by decreased microbial richness and evenness, increased relative abundances of OTUs within *Enterococcus, Enterobacter*, and *Bacteroides*, and decreased *Faecalibacterium, Roseburia, Blautia* and *Bacteroides*.

These results also demonstrated that clinical biomarkers (e.g., current/recent hospitalization, immune suppression, recent antibiotics, and prior CDI) can, independent of underlying disease state, predict dysbiosis.

These results showed that humanized mice colonized with dysbiotic microbiota exhibit increased susceptibility to colonization and inflammation following CDI, and that fecal transplant from healthy human donor can decrease susceptibility to CDI in humanized mice with dysbiotic microbiota.

Example 2: Study on Individuals with Diarrhea

Using the 5 clinical risk factors identified in Example 1, the records of 20,687 patients (Table 4) who presented with diarrhea and were tested for *Clostridium difficile* at Mayo Clinic, Rochester, MN between 2011-2016 were examined. All patients were over 18 years of age (IRB 16-003622). Patients who tested negative and then subsequently tested positive were marked as "converters." Patients who tested negative but never tested positive were marked as "non-converters." A single "test negative" date was preserved for each patient and no patients were duplicated in this analysis. Based on the "test negative" date, all 5 risk factors were evaluated for each patient including: prior *C. difficile* infection, recent hospitalization (within the previous 4 weeks), current hospitalization, antibiotic use (within the previous 3 weeks), and immunosuppression.

TABLE 4

Demographic information on converters and non-converters

|  | Converter (n = 662) | Non-Converter (n = 22, 141) |
|---|---|---|
| Sex, n (%) | | |
| Male | 311 (47) | 9,873 (45) |
| Female | 351 (53) | 12,268 (55) |
| Age (yr) | | |
| Mean (SD) | 60.0 (15.2) | 59.9 (17.7) |
| Range | 18-95 | 18-106 |
| BMI (SD) | 29.8 (7.3) | 29.1 (7.3) |

Using univariate logistic regression analysis, each risk factor significantly predicted *C. difficile* susceptibility, or "conversion" to a *C. difficile* positive state from a *C. difficile* negative state (Table 5).

TABLE 5

| Risk Factor | p-value |
|---|---|
| Prior *C. difficile* infection | <2e−16 |
| Current Hospitalization | <2e−16 |
| Recent Hospitalization (within previous 4 weeks) | <2e−16 |
| Antibiotics (within previous 3 weeks) | <2e−16 |
| Immunosuppression | <2e−16 |

Relative risk was calculated for each risk factor (Table 6) and for the number of risk factors each converter exhibited (Table 7). Individuals with 2 or more risk factors were between 1.22-6.8 times more likely to convert to a *C. difficile* positive state.

TABLE 6

Relative risk of converting by risk factor.

| Risk Factor | Relative Risk |
|---|---|
| Antibiotics | 3.38 |
| Immunosuppression | 2.50 |
| Recent Hospitalization | 2.95 |
| Current Hospitalization | 3.20 |
| Prior CDI | 5.17 |

TABLE 7

Risk of converting based on number of risk factors.

| Number of risk factors | Relative Risk | Odds Ratio |
|---|---|---|
| 0 | 0.33 | 1 |
| 1 | 0.43 | 1.16 |
| 2 | 1.22 | 2.86 |
| 3 | 1.81 | 3.83 |
| 4 | 3.33 | 6.50 |
| 5 | 6.8 | 16.06 |

Example 3: Treating Mice at Risk of *C. difficile* Infection with Probiotic Cocktail Germ free mice were given to probiotic delivery of gut microbiota from patients who had diarrhea with either healthy-like or dysbiotic microbiota as shown in FIG. 20.

The probiotic cocktail included 3 microbial biomarkers associated with healthy-like humans: *Roseburia feacis, Faecalibacterium prausnitzii, Akkermansia muciniphila*.

TABLE 8

Probiotic Cocktail.

| Bacterial Genera | Test-Statistic | p-value | Bonferroni p-value | Dysbiotic Mean | Healthy-like Mean | Feature Importance Score | Boruta Algorithm |
|---|---|---|---|---|---|---|---|
| Roseburia | 33.14 | <0.0001 | <0.0001 | 523.80 | 1845.95 | 8 | Confirmed |
| Faecalibacterium | 32.05 | <0.0001 | <0.0001 | 510.43 | 1383.51 | 6 | Confirmed |
| Akkermansia | 2.54 | 0.11 | 1.00 | 1263.02 | 2102.48 | 1421 | Confirmed |
| Bacteroides | 27.08 | <0.0001 | <0.0001 | 387.24 | 1442.80 | 2 | Confirmed |
| Blautia | 16.13 | <0.0001 | 0.001 | 1209.83 | 1950.36 | 4 | Confirmed |
| Bacteroides | 14.27 | <0.0001 | 0.003 | 2614.15 | 4165.36 | 9 | Confirmed |

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The invention claimed is:

1. A method for treating *Clostridium difficile* infection in a mammal, the method comprising:
   administering a composition comprising at least three bacteria selected from the group consisting of *Roseburia, Faecalibacterium, Akkermansia, Blautia,* and *Bacteroides* to a mammal identified as having an increased level of at least one free amino acid, wherein the at least one free amino acid is selected from the group consisting of proline, alanine, glycine, histidine, isoleucine, leucine, methionine, phenylalanine, threonine, tryptophan, tyrosine, and valine,
   wherein said composition restores a heathy gut microbiota in said mammal.

2. The method of claim 1, wherein the at least one free amino acid comprises proline.

3. The method of claim 1, wherein the at least three bacteria comprise *Roseburia faecis, Faecalibacterium prausnitzii,* and *Akkermansia muciniphila*.

4. The method of claim 1, wherein said mammal is a human.

5. The method of claim 1, wherein the composition is a pill, tablet, capsule, or enema.

6. The method of claim 1, wherein the composition is administered by fecal microbiota transplant (FMT).

7. The method of claim 1, wherein the composition is configured to deliver said at least three bacteria to the intestines of said mammal.

8. The method of claim 1, further comprising, prior to said administration, identifying the mammal as having at least one clinical risk factor of *C. difficile* infection.

9. The method of claim 8, wherein the at least one clinical risk factor is selected from the group consisting of hospitalization, immune suppression, antibiotic use, and prior *C. difficile* infection.

10. A method for preventing *Clostridium difficile* infection in a mammal, the method comprising:
    administering a composition comprising at least three bacteria selected from the group consisting of *Roseburia, Faecalibacterium, Akkermansia, Blautia,* and *Bacteroides* to a mammal identified as having an increased level of at least one free amino acid, wherein the at least one free amino acid is selected from the group consisting of proline, alanine, glycine, histidine, isoleucine, leucine, methionine, phenylalanine, threonine, tryptophan, tyrosine, and valine,
    wherein said composition restores colonization resistance to *C. difficile* in said mammal.

11. The method of claim 10, wherein the at least one free amino acid comprises proline.

12. The method of claim 10, wherein the at least three bacteria comprise *Roseburia faecis, Faecalibacterium prausnitzii,* and *Akkermansia muciniphila*.

13. The method of claim 10, wherein said mammal is a human.

14. The composition of claim 10, wherein the composition is a pill, tablet, capsule, or enema.

15. The method of claim 10, wherein the composition is administered by fecal microbiota transplant (FMT).

16. The method of claim 10, wherein the composition is configured to deliver said at least three bacteria to the intestines of said mammal.

17. The method of claim 10, further comprising, prior to said administration, identifying the mammal as having at least one clinical risk factor of *C. difficile* infection.

18. The method of claim 17, wherein the at least one clinical risk factor is selected from the group consisting of hospitalization, immune suppression, antibiotic use, and prior *C. difficile* infection.

\* \* \* \* \*

UNITED STATES PATENT AND TRADEMARK OFFICE
CERTIFICATE OF CORRECTION

PATENT NO. : 11,865,146 B2
APPLICATION NO. : 17/093154
DATED : January 9, 2024
INVENTOR(S) : Purna C. Kashyap, Eric J. Battaglioli and Vanessa L. Hale Page 1 of 1

It is certified that error appears in the above-identified patent and that said Letters Patent is hereby corrected as shown below:

On the Title Page

Column 2 (Item (57) Abstract), Line 8, delete "heathy" and insert -- healthy --.

In the Claims

Column 27, Line 22, In Claim 1, delete "heathy" and insert -- healthy --.

Signed and Sealed this
Twelfth Day of November, 2024

Katherine Kelly Vidal
*Director of the United States Patent and Trademark Office*